United States Patent [19]

Fischer et al.

[11] Patent Number: 5,945,444
[45] Date of Patent: Aug. 31, 1999

[54] 3-ARYL-4-HYDROXY-$\Delta^3$-DIHYDROTHIOPHENONE DERIVATIVES

[75] Inventors: Reiner Fischer, Monheim; Jacques Dumas, Köln; Thomas Bretschneider, Lohmar; Christoph Erdelen, Leichlingen; Ulrike Wachendorff-Neumann, Neuwied, all of Germany

[73] Assignee: Bayer Aktiengesellschaft, Leverkusen, Germany

[21] Appl. No.: 08/716,361

[22] PCT Filed: Mar. 14, 1995

[86] PCT No.: PCT/EP95/00953

§ 371 Date: Sep. 18, 1996

§ 102(e) Date: Sep. 18, 1996

[87] PCT Pub. No.: WO95/26345

PCT Pub. Date: Oct. 5, 1995

[30] Foreign Application Priority Data

Mar. 25, 1994 [DE] Germany ............... 44 10 420

[51] Int. Cl.⁶ ............... A01N 43/10; C07D 333/32
[52] U.S. Cl. ............... 514/445; 549/62; 549/65; 549/66
[58] Field of Search ............... 549/62, 65, 66; 514/445

[56] References Cited

U.S. PATENT DOCUMENTS 5,262,383 11/1993 Fischer et al. ............... 504/195

FOREIGN PATENT DOCUMENTS 0 528 156 2/1993 European Pat. Off. .

OTHER PUBLICATIONS

J.Chem.Soc., Chemical Communications, No. 16, 1987, Letchworth GB, pp. 1228–1230, Chambers et al. 'An Asymmetric Synthesis . . . Rearrangement.'

J.of Antibiotics, vol. 36, No. 11, 1983, pp. 1589–1591, Tsuzuki et al. 'Biological Activities of thiotetromycin Analogs'.

*Primary Examiner*—Patricia L. Morris
*Attorney, Agent, or Firm*—Sprung Kramer Schaefer & Briscoe

[57] ABSTRACT

The present invention relates to novel 3-aryl-4-hydroxy-$\Delta^3$-dihydrothiophenone derivatives of the formula (I)

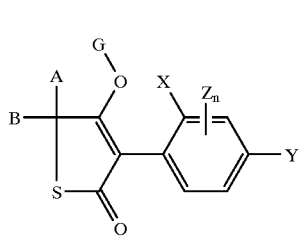

in which

A, B, G, S, X, Y, Z and n have the meaning given in the description, to processes for their preparation, to novel intermediates and to the use of the compounds of the formula (I) as agents for controlling pests.

11 Claims, No Drawings

3-ARYL-4-HYDROXY-Δ³-DIHYDROTHIOPHENONE DERIVATIVES

This application is a 371 of PCT/EP95/00953 filed Mar. 14, 1995.

The present invention relates to novel 3-aryl-4-hydroxy-Δ³-dihydrothiophenone derivatives, to processes for their preparation and to their use as agents for controlling pests.

It is known that certain substituted Δ³-dihydrofuran-2-one derivatives possess herbicidal properties (cf. DE-A 4 014 420). The synthesis of the tetronic acid derivatives (such as, for example, 3-(3-methylphenyl)-4-hydroxy-5-(4-fluorophenyl)-Δ³-dihydrofuran-2-one) used as starting compounds is also described in DE-A 4 014 420. The publication Campbell et al. J. Chem. Soc., Perkin Trans. 1 1985, (8) 1567–8 also discloses similarly structured compounds without indicating any insecticidal and/or acaridical activity. In addition to this, EP 528 156 discloses 3-aryl-Δ³-dihydrofuranone derivatives having herbicidal, acaridical and insecticidal properties; however, the effects described in this publication are not always adequate.

Novel 3-aryl-4-hydroxy-Δ³-dihydrothiophenone derivatives of the formula (I)

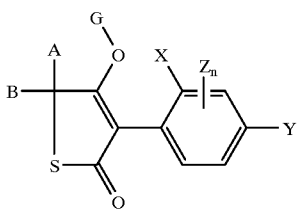

(I)

have now been found in which
X represents alkyl, halogen, alkoxy or halogenoalkyl,
Y represents hydrogen, alkyl, halogen, alkoxy or halogenoalkyl,
Z represents alkyl, halogen or alkoxy,
n represents a number from 0–3, or where the radicals X and Z, together with the phenyl radical to which they are bonded, form the naphthalene radical of the formula

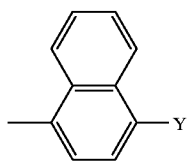

in which Y has the meaning given above,
A and B can be identical or different and represent alkyl, alkenyl, alkinyl, alkoxyalkyl, polyalkoxyalkyl or alkylthioalkyl which are in each case optionally substituted identically or differently once or more than once by halogen, cycloalkyl which is optionally substituted and is optionally interrupted by at least one heteroatom, or aryl, arylkyl or hetaryl which are in each case optionally substituted identically or differently once or more than once by halogen, alkyl, halogenoalkyl, alkoxy, halogenoalkoxy or nitro,
or in which
A and B, together with the carbon atom to which they are bonded, form a saturated or unsaturated ring which is optionally interrupted by at least one heteroatom and which is optionally substituted, or in which A and B, together with the carbon atom to which they are bonded, represent a ring in which two substituents, together with the carbon atoms to which they are bonded, represent a saturated or unsaturated ring which is optionally substituted identically or differently once or more than once by alkyl, alkoxy or halogen and which can be interrupted by oxygen or sulfur,
G represents hydrogen (a) or represents one of the groups (b)

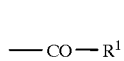

(c)

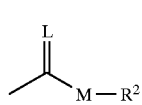

(d)

(e)

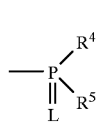

(f)

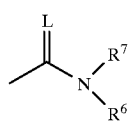

or (g)

$E^+$ $E^\oplus$ represents a metal ion equivalent or an ammonium ion,
L represents oxygen or sulfur,
M represents oxygen or sulfur,
$R^1$ represents alkyl, alkenyl, alkoxyalkyl, alkylthioalkyl or polyalkoxyalkyl which are in each case optionally substituted identically or differently once or more than once by halogen, or cycloalkyl which is optonally substituted by halogen or alkyl and can be interrupted by at least one heteroatom, or represents in each case optionally substituted phenyl, phenylalkyl, hetaryl, phenoxyalkyl or hetaryloxyalkyl, and
$R^2$ represents alkyl, alkenyl, alkoxyalkyl or polyalkoxyalkyl which are in each case optionally substituted identically or differently once or more than once by halogen, or in each case optionally substituted cycloalkyl, phenyl or benzyl.
$R^3$, $R^4$ and $R^5$, independently of each other, represent alkyl, alkoxy, alkylamino, dialkylamino, alkylthio, alkenylthio, alkinylthio or cycloalkylthio which are in each case optionally substituted identically or differently once or more than once by halogen or represent in each case optionally substituted phenyl, benzyl, phenoxy or phenylthio,
$R^6$ and $R^7$, independently of each other, represent hydrogen, or alkyl, alkenyl, alkoxy or alkoxyalkyl which are in each case optionally substituted identically or differently once or more than once by halogen, represent in each case optionally substituted phenyl, or benzyl,
or $R^6$ and $R^7$, together represent an alkylene radical which is optionally interrupted by oxygen or sulfur.

When the different meanings (a), (b), (c), (d), (e), (f) and (g) of the Group G are included, the following principle structures (Ia) to (Ig) ensue:

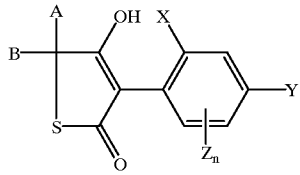
(Ia)

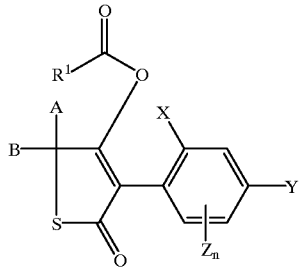
(Ib)

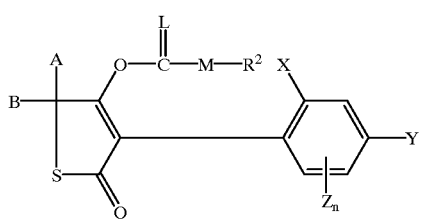
(Ic)

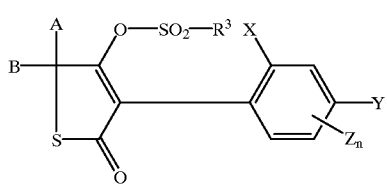
(Id)

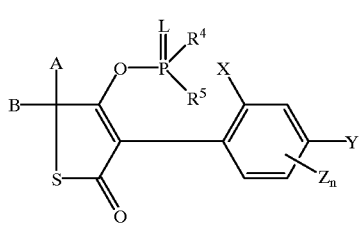
(Ie)

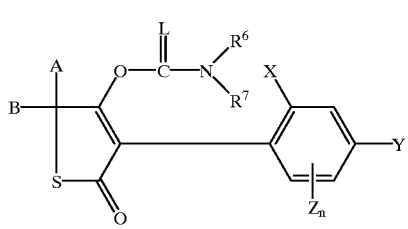
(If)

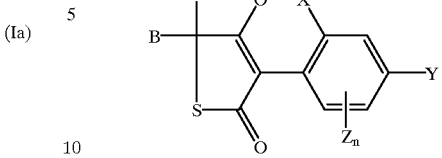
(Ig)

where

A, B, E, L, M, X, Y, Z, $R^1$, $R^2$, $R^3$, $R^4$, $R^5$, $R^6$, $R^7$ and n possess the abovementioned meanings.

In general, due to the presence of one or more centers of chirality, the compounds of the formulae (Ia)–(Ig) result as stereoisomeric mixtures which can, where appropriate, be resolved in a customary manner. The compounds can be used both in the form of their diastereomeric mixtures and as pure diastereomers or enantiomers. For the sake of simplicity, reference will always be made below to compounds of the formulae (Ia) to (Ig) although both the pure compounds and the mixtures containing different proportions of isomeric, enantiomeric and stereomeric compounds are meant.

In addition, it has been found (A) that 3-aryl-4-hydroxy-$\Delta^3$-dihydrothiophenone derivatives of the formula (Ia)

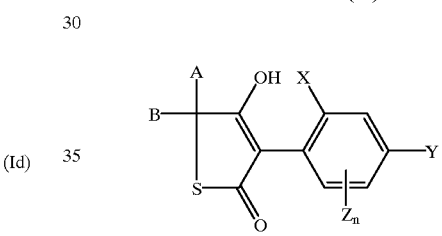
(Ia)

in which

A, B, X, Y, Z and n have the abovementioned meaning, are obtained if

β-ketocarboxylic esters of the formula (II)

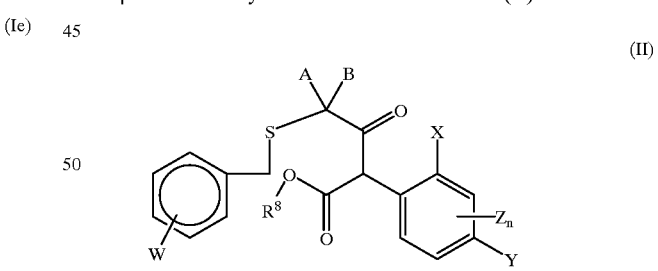
(II)

in which

A, B, X, Y, Z and n have the abovementioned meaning,

W represents hydrogen, halogen, alkyl (in particular $C_1$–$C_8$-alkyl) or alkoxy (in particular $C_1$–$C_8$-alkoxy), and $R^8$ represents alkyl (in particular $C_1$–$C_8$-alkyl), are subjected to intramolecular cyclization, optionally in the presence of a diluent and in the presence of an acid, and (B) that compounds of the formula (Ib)

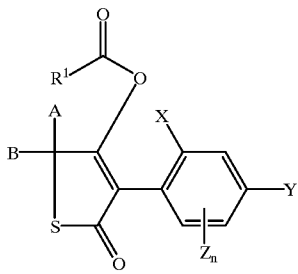
(Ib)

in which

A, B, X, Y, Z, $R^1$ and n have the abovementioned meaning, are obtained if compounds of the formula (Ia)

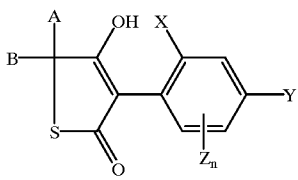
(Ia)

in which

A, B, X, Y, Z and N have the abovementioned meaning,

α) are reacted with acid halides of the formula (III)

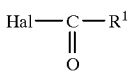
(III)

in which $R^1$ has the abovementioned meaning and

Hal represents halogen, in particular chlorine or bromine, optionally in the presence of a diluent and optionally in the presence of an acid binding agent, or β) are reacted with carboxylic anhydrides of the formula (IV)

  $R^1\text{—CO—O—CO—}R^1$ (IV)

in which $R^1$ has the abovementioned meaning, optionally in the presence of a diluent and optionally in the presence of an acid binding agent, and (C) that compounds of the formula (Ic)

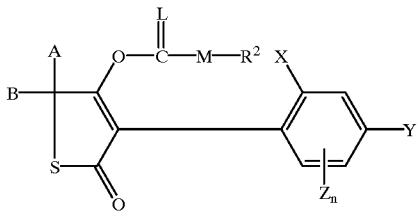
(Ic)

in which

A, B, X, Y, Z, $R^2$ and n have the abovementioned meaning,

L represents oxygen, and

M represents oxygen or sulfur, are obtained if compounds of the formula (Ia)

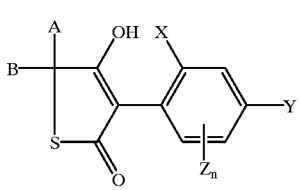
(Ia)

in which

A, B, X, Y, Z and n have the abovementioned meaning, are reacted with chloroformic esters or chloroformic thioesters of the formula (V)

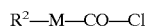   $R^2\text{—M—CO—Cl}$   (V)

in which $R^2$ and M have the abovementioned meaning, optionally in the presence of a diluent and optionally in the presence of an acid binding agent, and (D) that compounds of the formula (Ic)

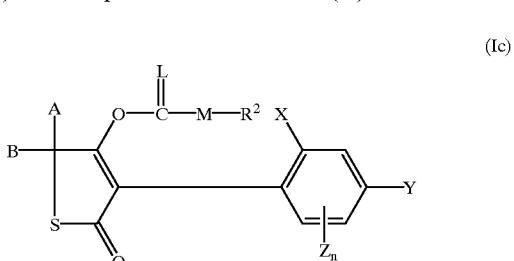
(Ic)

in which

A, B, $R^2$, X, Y, Z and n have the abovementioned meaning,

L represents sulfur, and

M represents oxygen or sulfur, are obtained if compounds of the formula (Ia)

(Ia)

in which
A, B, X, Y, Z and n have the abovementioned meanng,
α) are reacted with chloromonothioformic esters or chlorodithioformic esters of the formula (VI)

(VI)

in which
M and $R^2$ have the abovementioned meaning,
optionally in the presence of a diluent and optionally in the presence of an acid binding agent, or
β) reacted with carbon disulfide and then with alkyl halides of the formula (VI)

$R^2$—Hal      (VII)

in which
$R^2$ has the abovementioned meaning,
and
Hal represents chlorine, brormine or iodine, and
(E) that compounds of the formula (Id)

(Id)

in which
A, B, X, Y, Z, $R^3$ and n have the abovementioned meaning,
are obtained if compounds of the formula (Ia)

(Ia)

in which
A, B, X, Y, Z and n have the abovementioned meaning,
are reacted with sulfonyl chlorides of the formula (VIII)

$R^3$—$SO_2$—Cl      (VIII)

in which
$R^3$ has the abovementioned meaning
optionally in the presence of a diluent and optionally in the presence of an acid binding agent
and
(F) that compounds of the formula (Ie)

(Ie)

in which
A, B, L, X, Y, Z, $R^4$, $R^5$ and n have the abovementioned meaning,
are obtained if
compounds of the formula (Ia)

(Ia)

in which
A, B, X, Y, Z and n have the abovementioned meaning
are reacted with phosphorus compounds of the formula (IX)

(IX)

in which
L, $R^4$ and $R^5$ have the abovementioned meaning, and
Hal represents halogen, in particular chlorine or bromine,
optionally in the presence of a diluent and optionally in the presence of an acid binding agent, and
(G) that compounds of the formula (If)

(If)

in which
A, B, L, X, Y, Z, $R^6$, $R^7$ and n have the abovementioned meaning, are obtained if compounds of the formula (Ia)

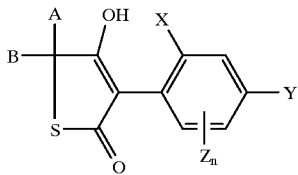
(Ia)

in which

A, B, X, Y, Z and n have the abovementioned meaning

α) are reacted with isocyanates or isothiocyanates of the formula (X)

 (X)

in which

R⁶ and L have the abovementioned meaning optionally in the presence of a diluent and optionally in the presence of a catalyst, or β) are reacted with carbamoyl chlorides or thiocarbamoyl chlorides of the formula (XI)

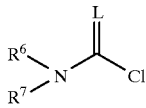
(XI)

in which

L, R⁶ and R⁷ have the abovementioned meaning, optionally in the presence of a diluent and optionally in the presence of an acid binding agent, and (H) that compounds of the formula (Ig)

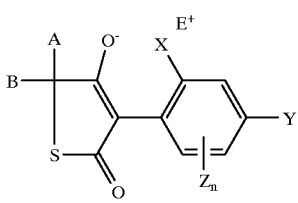
(Ig)

in which

X, Y, Z, A, B and n have the abovementioned meaning, and E⁺ represents a metal ion equivalent or represents an ammonium ion, are obtained if compounds of the formula (Ia)

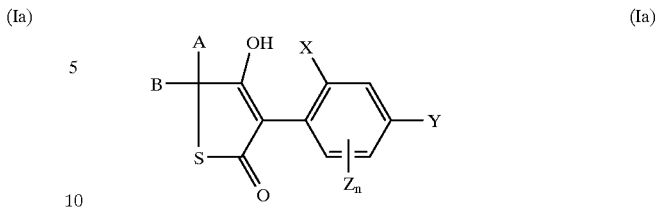
(Ia)

in which

X, Y, Z, A, B and n have the abovementioned meaning, are reacted with metal hydroxides, metal alkoxides or amines of the formulae (XII) and (XIII)

 (XII)

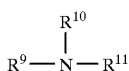 (XIII)

in which

Me represents singly charged or doubly charged metal ions, for example the metals sodium, potassium, magnesium or calcium, and t represents the number 1 or 2, and $R^9$, $R^{10}$ and $R^{11}$, independently of each other, represent hydrogen or alkyl (in particular $C_1$–$C_8$-alkyl), optionally in the presence of a diluent.

In addition to this, it has been found that the novel 3-aryl-4-hydroxy-$\Delta^3$-dihydrothiophenone derivatives of the formula (I) are distinguished by outstanding acaricidal and insecticidal activities.

The novel compounds are defined generally by the formula (I).

X preferably represents $C_1$–$C_6$-alkyl, halogen, $C_1$–$C_6$-alkoxy or $C_1$–$C_3$-halogenoalkyl.

Y preferably represents hydrogen, $C_1$–$C_6$-alkyl, halogen, $C_1$–$C_6$-alkoxy or $C_1$–$C_3$-halogenoakyl.

Z preferably represents $C_1$–$C_6$-alkyl, halogen or $C_1$–$C_6$-alkoxy.

n preferably represents a number from 0 to 3 or the radicals X and Z preferably represent, together with the phenyl radical to which they are bonded, the naphthalene radical of the formula

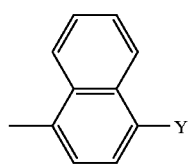

in which

Y has the abovementioned meaning.

A and B preferably represent, independently of each other, $C_1$–$C_{12}$-alkyl, $C_3$–$C_8$-alkenyl, $C_3$–$C_8$-alkinyl, $C_1$–$C_{10}$-alkoxy-$C_1$–$C_8$-alkyl, $C_1$–$C_8$-polyalkoxy-$C_2$–$C_8$-alkyl or $C_1$–$C_{10}$-alkylthio-$C_1$–$C_8$-alkyl which are in each case optionally substituted identically or differently once or more than once by halogen, cycloalkyl having 3 to 8 ring atoms which is optionally substituted by halogen, $C_1$–$C_4$-alkyl or $C_1$–$C_4$-alkoxy and which can be interrupted by oxygen and/or sulfur, or phenyl, 5- or 6-membered hetaryl or phenyl-$C_1$–$C_6$-alkyl which are in each case optionally substituted identically or differently once or more than once by halogen, $C_1$–$C_6$-alkyl, $C_1$–$C_6$-halogenoalkyl, $C_1$–$C_6$-alkoxy, $C_1$–$C_6$-halogenoalkoxy or nitro, or A and B preferably represent, together with the carbon atom to which they are bonded, a saturated or unsaturated 3- to 8-membered ring which is optionally interrupted by oxygen and/or sulfur and optionally substituted identically or differently once or more than once by halogen, $C_1$–$C_6$-alkyl, $C_1$–$C_6$-alkoxy, $C_1$–$C_4$-halogenoalkyl, $C_1$–$C_4$-halogenoalkoxy, $C_1$–$C_4$-alkylthio or phenyl which is optionally substituted identically or differently, once or more than once by halogen, $C_1$–$C_6$-alkyl or $C_1$–$C_6$-alkoxy, or A and B preferably represent, together with the carbon atom to which are bonded a $C_3$–$C_8$-membered ring in which two substituents, together with the carbon atoms to which they are bonded, represent a saturated or mono-unsaturated $C_5$–$C_7$ ring which is optionally substituted identically or differently once or more than once by $C_1$–$C_6$-alkyl, $C_1$–$C_6$-alkoxy or halogen and which can be interrupted by oxygen or sulfur.

G preferably represents hydrogen (a) or represents one of the groups (b)
—CO—R¹

(c)
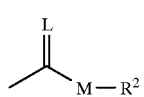

(d)
—SO₂—R³

(e)

(f)

or (g)
E⁺ in which

E⁺ represents a metal ion equivalent or an ammoium ion,

L represents oxygen or sulfur and

M represents oxygen or sulfur.

R¹ preferably represents $C_1$–$C_{20}$-alkyl, $C_2$–$C_{20}$-alkenyl, $C_1$–$C_8$-alkoxy-$C_1$–$C_8$-alkyl, $C_1$–$C_8$-alkylthio-$C_1$–$C_8$-alkyl or $C_2$–$C_8$-polyalkoxy-$C_2$–$C_8$-alkyl which are in each case optionally substituted identically or differently once or more than once by halogen, or cycloalkyl having 3 to 8 ring atoms which is optionally substituted by halogen or $C_1$–$C_6$-alkyl and can be interrupted by at least one oxygen and/or sulfur atom, represents phenyl which is optionally substituted identically or differently once or more than once by halogen, nitro, $C_1$–$C_6$-alkyl, $C_1$–$C_6$-alkoxy, $C_1$–$C_6$-halogenoalkyl or $C_1$–$C_6$-halogenoalkoxy, represents phenyl-$C_1$–$C_6$-alkyl which is optionally substituted identically or differently once or more than once by halogen, $C_1$–$C_6$-alkyl, $C_1$–$C_6$-alkoxy, $C_1$–$C_6$-halogenoalkyl or $C_1$–$C_6$-halogenoalkoxy, represents 5- or 6-membered hetaryl which is optionally substituted identically or differently once or more than once by halogen or $C_1$–$C_6$-alkyl, represents phenoxy-$C_1$–$C_6$-alkyl which is optionally substituted identically or differently once or more than once by halogen or $C_1$–$C_6$-alkyl, or represents 5- or 6-membered hetaryloxy-$C_1$–$C_6$-alkyl which is optionally substituted identically or differently once or more than once by halogen, amino or $C_1$–$C_6$-alkyl.

R² preferably represents $C_1$–$C_{20}$-alkyl, $C_2$–$C_{20}$-alkenyl, $C_1$–$C_8$-alkoxy-$C_2$–$C_8$-alkyl or $C_1$–$C_8$-polyalkoxy-$C_2$–$C_8$-alkyl which are in each case optionally substituted identically or differently once or more than once by halogen, or represents $C_3$–$C_8$-cycloalkyl which is optionally substituted by halogen, $C_1$–$C_4$-alkyl or $C_1$–$C_4$-alkoxy, or represents phenyl or benzyl which are in each case optionally substituted identically or differently once or more than once by halogen, nitro, $C_1$–$C_6$-alkyl, $C_1$–$C_6$-alkoxy or $C_1$–$C_6$-halogenoalkyl.

R³, R⁴ and R⁵ preferably represent, independently of each other, $C_1$–$C_8$-alkyl, $C_1$–$C_8$-alkoxy, $C_1$–$C_8$-alkylamino, di-($C_1$–$C_8$)-alkylamino, $C_1$–$C_8$-alkylthio, $C_2$–$C_5$-alkenylthio, $C_2$–$C_5$-alkinylthio or $C_3$–$C_7$-cycloalkylthio which are in each case optionally substituted identically or differently once or more than once by halogen, or represent phenyl, benzyl, phenoxy or phenylthio which are in each case optionally substituted identically or differently once or more than once by halogen, nitro, cyano, $C_1$–$C_4$-alkoxy, $C_1$–$C_4$-halogenoalkoxy, $C_1$–$C_4$-alkylthio, $C_1$–$C_4$-halogenoalkylthio, $C_1$–$C_4$-alkyl or $C_1$–$C_4$-halogenoalkyl.

R⁶ and R⁷ preferably represent, independently of each other hydrogen or $C_1$–$C_{20}$-alkyl, $C_1$–$C_{20}$-alkoxy, $C_2$–$C_8$-alkenyl or $C_1$–$C_{20}$-alkoxy-$C_1$–$C_{20}$-alkyl which are in each case optionally substituted identically or differently once or more than once by halogen, represent phenyl or benzyl which are in each case optionally substituted identically or differently once or more than once by halogen, $C_1$–$C_{20}$-halogenoalkyl, $C_1$–$C_{20}$-alkyl or $C_1$–$C_{20}$-alkoxy, or together represent a $C_2$–$C_6$-alkylene radical which is optionally interrupted by oxygen.

X particularly preferably represents $C_1$–$C_6$-alkyl, halogen, $C_1$–$C_6$-alkoxy or $C_1$–$C_2$-halogenoalkyl.

Y particularly preferably represents hydrogen, $C_1$–$C_6$-alkyl, halogen, $C_1$–$C_6$-alkoxy or $C_1$–$C_2$-halogenoalkyl.

Z particularly preferably represents $C_1$–$C_4$-alkyl, halogen or $C_1$–$C_4$-alkoxy.

n particularly preferably represents a number from 0 to 2.

or the radicals X and Z particularly preferably represent, together with the phenyl radical to which they are bonded, the naphthalene radical of the formula

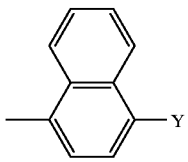

in which

Y has the abovementioned meaning.

A and B particularly preferably represent, independently of each other, $C_1$–$C_{10}$-alkyl, $C_3$–$C_6$-alkenyl, $C_3$–$C_6$-alkinyl, $C_1$–$C_8$-alkoxy-$C_1$–$C_6$-alkyl, $C_1$–$C_6$-polyalkoxy-$C_2$–$C_6$-alkyl or $C_1$–$C_8$-alkylthio-$C_1$–$C_6$-alkyl which are in each case optionally substituted identically or differently once or more than once by fluorine or chlorine, cycloalkyl which has 3 to 7 ring atoms and which is optionally substituted by fluorine, chlorine, $C_1$–$C_3$-alkyl or $C_1$–$C_3$-alkoxy and can be interrupted by 1 to 2 oxygen and/or sulfur atoms, or represent phenyl, pyridyl. imidazolyl, pyrazolyl, triazolyl, indolyl, thiazolyl or phenyl-$C_1$–$C_4$-alkyl which are in each case optionally substituted identically or differently once or more than once by fluorine, chlorine, bromine, $C_1$–$C_4$-alkyl, $C_1$–$C_4$-halogenoalkyl. $C_1$–$C_4$-alkoxy or nitro, or A and B particularly preferably represent, together with the carbon atom to which they are bonded, a saturated or unsaturated 3- to 8-membered ring which is optionally interrupted by oxygen and/or sulfur and which is optionally substituted identically or differently once or more than once by fluorine, chlorine, $C_1$–$C_5$-alkyl, $C_1$–$C_5$-alkoxy, $C_1$–$C_3$-halogenoalkyl, $C_1$–$C_4$-halogenoalkoxy, $C_1$–$C_3$-alkylthio or phenyl which is optionally substituted identically or differently once or more than once by fluorine, chlorine, bromine, $C_1$–$C_4$-alkyl or $C_1$–$C_4$-alkoxy, or A and B particularly preferably represent, together with the carbon atom to which they are bonded, a $C_4$–$C_7$-membered ring in which two substituents, together with the carbon atoms to which they are bonded, represent a saturated or unsaturated $C_5$–$C_6$ ring which is optionally substituted identically or differently once or more than once by $C_1$–$C_3$-alkyl, $C_1$–$C_3$-alkoxy, fluorine or chlorine, and which can be interrupted by oxygen or sulfur.

G particularly preferably represents hydrogen (a) or represents one of the groups

(b)

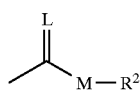

(c)

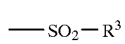

(d)

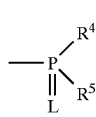

(e)

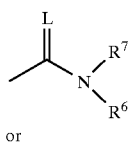

(f)

or (g)

$E^+$ in which $E^+$ represents a metal ion equivalent or an ammonium ion, and

L represents oxygen or sulfur, and

M represents oxygen or sulfur.

$R^1$ particularly preferably represents $C_1$–$C_{16}$-alkyl, $C_2$–$C_{16}$-alkenyl, $C_1$–$C_6$-alkoxy-$C_1$–$C_6$-alkyl, $C_1$–$C_6$-alkylthio-$C_1$–$C_6$-alkyl or $C_1$–$C_6$-alkyl which are in each case optionally substituted identically or differently once or more than once by halogen, or cycloalkyl having 3 to 7 ring atoms which is optionally substituted by fluorine, chlorine or $C_1$–$C_4$-alkyl, and can be interrupted by 1 to 2 oxygen and/or sulfur atoms, p2 represents phenyl which is optionally substituted identically or differently once to five times by halogen, nitro, $C_1$–$C_4$-alkyl, $C_1$–$C_4$-alkoxy, $C_1$–$C_3$-halogenoalkyl or $C_1$–$C_3$-halogenoalkoxy, represents phenyl-$C_1$–$C_4$-alkyl which is optionally substituted identically or differently once to five times by halogen, $C_1$–$C_4$-alkyl, $C_1$–$C_4$-alkoxy, $C_1$–$C_3$-halogenoalkyl or $C_1$–$C_3$-halogenoalkoxy, represents pyridyl, thienyl, furanyl, pyrimidyl, thiazolyl or pyrazolyl which are optionally substituted identically or differently once to four times by halogen or $C_1$–$C_6$-alkyl, represents phenoxy-$C_1$–$C_5$-alkyl which is optionally substituted identically or differently once to five times by halogen or $C_1$–$C_4$-alkyl, represents pyridyloxy-$C_1$–$C_5$-alkyl, pyrimidyloxy-$C_1$–$C_5$-alkyl and thiazolyoxy-$C_1$–$C_5$-alkyl which are optionally substituted identically or differently once to four times by halogen, amino or $C_1$–$C_4$-alkyl.

$R^2$ particularly preferably represents $C_1$–$C_{16}$-alkyl, $C_2$–$C_{16}$-alkenyl, $C_1$–$C_6$-alkoxy-$C_2$–$C_6$-alkyl or $C_1$–$C_6$-polyalkoxy-$C_2$–$C_6$-alkyl which are in each case optionally substituted identically or differently once or more than once by halogen, or represents $C_3$–$C_7$-cycloalkyl which is optionally substituted by fluorine, chlorine, $C_1$–$C_3$-alkyl or $C_1$–$C_3$-alkoxy, or represents phenyl or benzyl which are in each case optionally substituted identically or differently once to five times by halogen, nitro, $C_1$–$C_4$-alkyl, $C_1$–$C_3$-alkoxy or $C_1$–$C_3$-halogenoalkyl.

$R^3$, $R^4$ and $R^5$ particularly preferably represent, independently of each other $C_1$–$C_6$-alkyl, $C_1$–$C_6$-alkoxy, $C_1$14 $C_6$-alkylamino, di-($C_1$–$C_6$)-alkylamino, $C_1$–$C_6$-alkylthio, $C_3$–$C_4$-alkenylthio, $C_2$–$C_4$-alkinylthio or $C_3$–$C_6$-cycloalkylthio which are in each case optionally substituted identically or differently once or more than once by halogen, or represent phenyl, benzyl, phenoxy or phenylthio which are in each case optionally substituted identically or differently once to five times by fluorine, chlorine, bromine, nitro, cyano, $C_1$–$C_3$-alkoxy, $C_1$–$C_3$halogenoalkoxy, $C_1$–$C_3$-alkylthio, $C_1$–$C_3$-halogenoakylthio, $C_1$–$C_3$-alkyl or $C_1$–$C_3$-halogenoalkyl.

R⁶ and R⁷ particularly preferably represent, independently of each other hydrogen, or $C_1-C_{20}$-alkyl, $C_1-C_{20}$-alkoxy, $C_2-C_8$-alkenyl or $C_1-C_{20}$-alkoxy-$C_1-C_{20}$-alkyl which are in each case optionally substituted identically or differently once or more than once by halogen, represent phenyl or benzyl which is optionally substituted identically or differently once to five times by halogen, $C_1-C_5$-halogenoalkyl, $C_1-C_5$-alkyl or $C_1-C_5$-alkoxy, or together represent a $C_4-C_6$-alkylene radical which is optionally interrupted by oxygen or sulfur.

X very particularly preferably represents methyl, ethyl, propyl, i-propyl, fluorine, chlorine, bromine, methoxy, ethoxy or trifluoromethyl.

Y very particularly preferably represents hydrogen, methyl, ethyl, propyl, i-propyl, butyl, i-butyl, tert-butyl, fluorine, chlorine, bromine, methoxy, ethoxy or trifluoromethyl.

Z very particularly preferably represents methyl, ethyl, i-propyl, butyl, i-butyl, tert-butyl, fluorine, chlorine, bromine, methoxy or ethoxy.

n very particularly preferably represents a number 0 or 1 or the radicals X and Z very particularly preferably represent, together with the phenyl radical to which they are bonded, the radical of the formula

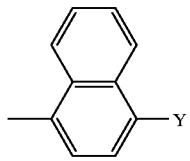

in which Y has the abovementioned meaning.

A and B very particularly preferably represent, independently of each other, $C_1-C_8$-alkyl, $C_3-C_4$-alkenyl, $C_3-C_4$-alkinyl, $C_1-C_6$-alkoxy-$C_1-C_4$-alkyl, $C_1-C_4$-polyalkoxy-$C_2-C_4$-alkyl or $C_1-C_6$-alkylthio-$C_1-C_4$-alkyl which are in each case optionally substituted identically or differently once to nine times by fluorine or chlorine, cycloalkyl which has 3 to 6 ring atoms and which can be interrupted by 1-2 oxygen and/or sulfur atoms, or phenyl or benzyl which are in each case optionally substituted identically or differently once to five times by fluorine, chlorine, methyl, ethyl, propyl, iso-propyl, methoxy, ethoxy, trifluoromethyl or nitro, or A and B very particularly preferably represent, together with the carbon atom to which they are bonded, a saturated or unsaturated 3- to 8-membered ring which is optionally interrupted by oxygen and/or sulfur and is optionally substituted identically or differently once to five times by fluorine, chlorine, $C_1-C_4$-alkyl, $C_1-C_4$-alkoxy, trifluoromethyl, $C_1-C_2$-alkylthio or phenyl which is optionally substituted identically or differently once to three times by fluorine, chlorine, methyl or methoxy, or A and B very particularly preferably represent, together with the carbon atom to which they are bonded, a $C_3-C_6$-membered ring in which two substituents, together with the carbon atoms to which they are bonded, represent a saturated or unsaturated $C_5-C_6$-ring which is optionally substituted identically or differently once to five times by methyl, ethyl, methoxy, ethoxy, fluorine or chlorine, and which can be interrupted by oxygen or sulfur.

G very particularly preferably represents hydrogen (a) or represents one of the groups (b)

(c)
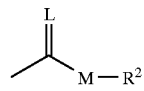

(d)
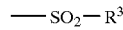

(e)

(f)
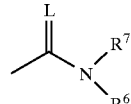

or (g)

in which

E⁺ represents a metal ion equivalent or an ammonium ion,

L represents oxygen or sulfur and

M represents oxygen or sulfur.

R¹ very particularly preferably represents $C_1-C_{14}$-alkyl, $C_2-C_{14}$-alkenyl, $C_1-C_4$-alkoxy-$C_1-C_6$-alkyl, $C_1-C_4$-alkylthio-$C_1-C_6$-alkyl or $C_1-C_4$-polyalkoxy-$C_2-C_4$-alkyl which are in each case optionally substituted identically or differently once to nine times by fluorine or chlorine, or cycloalkyl which has 3 to 6 ring atoms, which is optionally substituted by fluorine, chlorine, methyl or ethyl, and can be interrupted by 1-2 oxygen and/or sulfur atoms, represents phenyl which is optionally substituted identically or differently once to three times by fluorine, chlorine, bromine, methyl, ethyl, propyl, i-propyl, methoxy, ethoxy, trifluoromethyl, trifluoromethoxy or nitro, represents phenyl-$C_1-C_3$-alkyl which is optionally substituted identically or differently once to three times by fluorine, chlorine, bromine, methyl, ethyl, propyl, i-propyl, methoxy, ethoxy, trifluoromethyl or trifluormethoxy, represents pyridyl, thienyl or furanyl which are in ease case optionally substituted identically or differently once to three times by fluorine, chlorine, bromine, methyl or ethyl, represents phenoxy-$C_1-C_4$-alkyl which is optionally substituted identically or differently once to three times by fluorine, chlorine, methyl or ethyl, or represents pyridyloxy-$C_1-C_4$-alkyl, pyrimidyloxy-$C_1-C_4$-alkyl and thiazolyloxy-$C_1-C_4$-alkyl which are in each case optionally substituted identically or differently once to three times by fluorine, chlorine, amino, methyl or ethyl.

R² very particularly preferably represents $C_1-C_{14}$-alkyl, $C_2-C_{14}$-alkenyl, $C_1-C_4$-alkoxy-$C_2-C_6$-alkyl or $C_1-C_4$-polyalkoxy-$C_2-C_6$-alkyl which are in each case optionally substituted identically or differently once to nine times by fluorine or chlorine, or represents $C_3$–$C_6$-cycloalkyl which is optionally substituted by fluorine, chlorine, methyl, ethyl, methoxy or ethoxy, or represents phenyl or benzyl which are in each case optionally substituted identically or differently once to three times by fluorine, chlorine, nitro, methyl, ethyl, propyl, i-propyl, methoxy, ethoxy or trifluoromethyl.

$R^3$, $R^4$ and $R^5$ very particularly preferably represent, independently of each other, $C_1$–$C_4$-alkyl, $C_1$–$C_4$-alkoxy, $C_1$–$C_4$-alkylamino, di-($C_1$–$C_4$-alkyl)-amino or $C_1$–$C_4$-alkylthio which are in each case optionally substituted identically or differently once to five times by fluorine or chlorine, represent phenyl, benzyl, phenoxy or phenylthio which are in each case optionally substituted identically or differently once to three times by fluorine, chlorine, bromine, nitro, cyano, $C_1$–$C_2$-alkoxy, $C_1$–$C_2$-fluoroalkoxy, $C_1$–$C_2$-chloroalkoxy, $C_1$–$C_2$-alkylthio, $C_1$–$C_2$-fluoroalkylthio, $C_1$–$C_2$-chloroalkylthio or $C_1$–$C_3$-alkyl.

$R^6$ and $R^7$ very particularly preferably represent, independently of each other hydrogen, or $C_1$–$C_{10}$-alkyl, $C_1$–$C_{10}$-alkoxy or $C_1$–$C_{10}$-alkoxy-($C_1$–$C_{10}$)alkyl which are in each case optionally substituted identically or differently once to nine times by fluorine, chlorine or bromine, represent phenyl which is optionally substituted identically or differently once to three times by fluorine, chlorine, bromine, $C_1$–$C_2$-halogenoalkyl, $C_1$–$C_2$-alkyl or $C_1$–$C_4$-alkoxy, represent benzyl which is optionally substituted identically or differently once to three times by fluorine, chlorine, bromine, $C_1$–$C_4$-alkyl, $C_1$–$C_4$-halogenoalkyl or $C_1$–$C_4$-alkoxy, or together represent a $C_4$–$C_6$-alkylene radical which is optionally interrupted by oxygen or sulfur.

The stereoisomerically pure forms (diastereomers, enantiomers), and mixtures of the stereoisomers, of compounds of the formula (I) are in each case included as well.

Hydrocarbon radicals may, also in combination with heteroatoms, such as, for example, in alkoxy or alkenylthio, be, in each case as far as possible, straight-chain or branched.

The above-listed general radical definitions and/or clarifications, or those listed in preference ranges, can be combined at will with each other and consequently between the respective ranges and preference ranges as well. They apply to the end products and also to the precursors and intermediates in a corresponding manner.

According to the invention, the compounds of the general formula (I) are preferred in which there is a combination of the meanings listed above as being (preferably) preferred.

According to the invention, the compounds of the general formula (I) are particularly preferred in which there is a combination of the meanings listed above as being particularly preferred.

According to the invention, the compounds of the general formula (I) are very particularly preferred in which there is a combination of the meanings listed above as being very particularly preferred.

In addition to the compounds mentioned in the preparation examples, the following 3-aryl-4-hydroxy-$\Delta^3$-dihydrothiophen-2-one derivatives of the formula (Ia) may be mentioned individually:

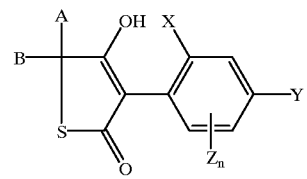

(Ia)

| A | B | X | Y | $Z_n$ |
|---|---|---|---|---|
| —$CH_3$ | —$CH_3$ | —$CH_3$ | —$CH_3$ | 6-$CH_3$ |
| —$C_2H_5$ | —$CH_3$ | —$CH_3$ | —$CH_3$ | 6-$CH_3$ |
| —$CH(CH_3)_2$ | —$CH_3$ | —$CH_3$ | —$CH_3$ | 6-$CH_3$ |
| —$CH_2$—$CH(CH_3)_2$ | —$CH_3$ | —$CH_3$ | —$CH_3$ | 6-$CH_3$ |
| —C₆H₅ (phenyl) | —$CH_3$ | —$CH_3$ | —$CH_3$ | 6-$CH_3$ |
| —$CH_2$—C₆H₅ (benzyl) | —$CH_3$ | —$CH_3$ | —$CH_3$ | 6-$CH_3$ |
| —$CH_2CH_2$—C₆H₅ | —$CH_3$ | —$CH_3$ | —$CH_3$ | 6-$CH_3$ |
| —$C_2H_5$ | —$C_2H_5$ | —$CH_3$ | —$CH_3$ | 6-$CH_3$ |
| —$CH(CH_3)_2$ | —$CH(CH_3)_2$ | —$CH_3$ | —$CH_3$ | 6-$CH_3$ |
| —$CH$=$CH_2$ | —$CH_3$ | —$CH_3$ | —$CH_3$ | 6-$CH_3$ |
| —$CF_3$ | —$CH_3$ | —$CH_3$ | —$CH_3$ | 6-$CH_3$ |
|  | —$(CH_2)_2$— | —$CH_3$ | —$CH_3$ | 6-$CH_3$ |
|  | —$(CH_2)_4$— | —$CH_3$ | —$CH_3$ | 6-$CH_3$ |
|  | —$(CH_2)_5$— | —$CH_3$ | —$CH_3$ | 6-$CH_3$ |
|  | —$(CH_2)_6$— | —$CH_3$ | —$CH_3$ | 6-$CH_3$ |
|  | —$(CH_2)_7$— | —$CH_3$ | —$CH_3$ | 6-$CH_3$ |

-continued

| A | B | X | Y | $Z_n$ |
|---|---|---|---|---|
| | $-CH_2-CHCH_3(CH_2)_2-$ | $-CH_3$ | $-CH_3$ | $6-CH_3$ |
| | $-CH(CH_3)-(CH_2)_4-$ | $-CH_3$ | $-CH_3$ | $6-CH_3$ |
| | $-CH_2-CH(CH_3)-(CH_2)_3-$ | $-CH_3$ | $-CH_3$ | $6-CH_3$ |
| | $-(CH_2)_2-CH(CH_3)-(CH_2)_2-$ | $-CH_3$ | $-CH_3$ | $6-CH_3$ |
| | $-C(CH_2)_2-CH-(CH_2)_2-$ <br> $\quad\quad\quad\;\; |$ <br> $\quad\quad\quad C(CH_3)_3$ | $-CH_3$ | $-CH_3$ | $6-CH_3$ |
| | $-(CH_2)_2-CH-(CH_2)_2-$ <br> $\quad\quad\quad |$ <br> $\quad\quad\quad C_6H_5$ (phenyl) | $-CH_3$ | $-CH_3$ | $6-CH_3$ |
| | $-CH_2-C(CH_3)_2-CH2-CH(CH_3)-CH_2-$ | $-CH_3$ | $-CH_3$ | $6-CH_3$ |
| | o-xylylene-CH$_2$CH$_2$ bridge | $-CH_3$ | $-CH_3$ | $6-CH_3$ |
| | $-(CH_2)_2-CH-(CH_2)_2-$ <br> $\quad\quad\quad |$ <br> $\quad\quad\quad C_2H_5$ | $-CH_3$ | $-CH_3$ | $6-CH_3$ |
| | $-(CH_2)_2-CH-(CH_2)_2-$ <br> $\quad\quad\quad |$ <br> $\quad\quad\quad i-C_3H_7$ | $-CH_3$ | $-CH_3$ | $6-CH_3$ |
| | $-CH_2-CHCH_3-CHCH_3-(CH_2)_2-$ | $-CH_3$ | $-CH_3$ | $6-CH_3$ |
| | $-(CH_2)_2-CHOCH_3(CH_2)_2-$ | $-CH_3$ | $-CH_3$ | $6-CH_3$ |
| | $-(CH_2)_2-CHOC_2H_5-(CH_2)_2-$ | $-CH_3$ | $-CH_3$ | $6-CH_3$ |
| $-CH_3$ | $-CH_3$ | Cl | Cl | H |
| $-C_2H_5$ | $-CH_3$ | Cl | Cl | H |
| $-CH(CH_3)_2$ | $-CH_3$ | Cl | Cl | H |
| $-CF_3$ | $-CH_3$ | Cl | Cl | H |
| | $-(CH_2)_4-$ | Cl | Cl | H |
| | $-(CH_2)_5-$ | Cl | Cl | H |
| | $-(CH_2)_6-$ | Cl | Cl | H |
| | $-CH_2-CH(CH_3)-(CH_2)_3-$ | Cl | Cl | H |
| | $-(CH_2)_2-CH(CH_3)-(CH_2)_2-$ | Cl | Cl | H |
| | $-(CH_2)_2-CH-(CH_2)_2-$ <br> $\quad\quad\quad |$ <br> $\quad\quad\quad C_2H_5$ | Cl | Cl | H |
| | $-(CH_2)_2-CH-(CH_2)_2-$ <br> $\quad\quad\quad |$ <br> $\quad\quad\quad i-C_3H_7$ | Cl | Cl | H |
| | $-CH_2-CHCH_3-CHCH_3-(CH_2)_2-$ | Cl | Cl | H |
| | $-(CH_2)_2-CHOCH_3-(CH_2)_2-$ | Cl | Cl | H |
| | $-(CH_2)-CHOC_2H_5-(CH_2)_2-$ | Cl | Cl | H |
| $-CH_3$ | $-CH_3$ | Cl | H | 6-Cl |
| $-C_2H_5$ | $-CH_3$ | Cl | H | 6-Cl |
| $-CH(CH_3)_2$ | $-CH_3$ | Cl | H | 6-Cl |
| $-CF_3$ | $-CH_3$ | Cl | H | 6-Cl |
| | $-(CH_2)_4-$ | Cl | H | 6-Cl |
| | $-(CH_2)_5-$ | Cl | H | 6-Cl |
| | $-(CH_2)_6-$ | Cl | H | 6-Cl |
| | $-CH_2-CH(CH_3)-(CH_2)_3-$ | Cl | H | 6-Cl |
| | $-(CH_2)_2-CH(CH_3)-(CH_2)_2-$ | Cl | H | 6-Cl |
| | $-(CH_2)_2-CH-(CH_2)_2-$ <br> $\quad\quad\quad |$ <br> $\quad\quad\quad C_2H_5$ | Cl | H | 6-Cl |

-continued

| A | B | X | Y | $Z_n$ |
|---|---|---|---|---|
|  | —(CH₂)₂—CH(i-C₃H₇)—(CH₂)₂— | Cl | H | 6-Cl |
|  | —(CH₂)₂—CHOCH₃—(CH₂)₂— | Cl | H | 6-Cl |
| —CH₃ | —CH₃ | Cl | H | 6-F |
| —C₂H₅ | —CH₃ | Cl | H | 6-F |
| —CH(CH₃)₂ | —CH₃ | Cl | H | 6-F |
| —CF₃ | —CH₃ | Cl | H | 6-F |
|  | —(CH₂)₄— | Cl | H | 6-F |
|  | —(CH₂)₅— | Cl | H | 6-F |
|  | —(CH₂)₆— | Cl | H | 6-F |
|  | —CH₂—CH(CH₃)—(CH₂)₃— | Cl | H | 6-F |
|  | —(CH₂)₂—CH(CH₃)—(CH₂)₂— | Cl | H | 6-F |
|  | —(CH₂)₂—CH(C₂H₅)—(CH₂)₂— | Cl | H | 6-F |
|  | —(CH₂)₂—CH(i-C₃H₇)—(CH₂)₂— | Cl | H | 6-F |
|  | —(CH₂)₂—CHOCH₃—(CH₂)₂— | Cl | H | 6-F |
| —CH₃ | —CH₃ | —CH₃ | —CH₃ | H |
| —C₂H₅ | —CH₃ | —CH₃ | —CH₃ | H |
| —CH(CH₃)₂ | —CH₃ | —CH₃ | —CH₃ | H |
| —CF₃ | —CH₃ | —CH₃ | —CH₃ | H |
|  | —(CH₂)₄— | —CH₃ | —CH₃ | H |
|  | —(CH₂)₅— | —CH₃ | —CH₃ | H |
|  | —(CH₂)₆— | —CH₃ | —CH₃ | H |
|  | —CH₂—CH(CH₃)—(CH₂)₃— | —CH₃ | —CH₃ | H |
|  | —(CH₂)₂—CH(CH₃)—(CH₂)₂— | —CH₃ | —CH₃ | H |
|  | —(CH₂)₂—CH(C₂H₅)—(CH₂)₂— | —CH₃ | —CH₃ | H |
|  | —(CH₂)₂—CH(i-C₃H₇)—(CH₂)₂— | —CH₃ | —CH₃ | H |
|  | —(CH₂)—CHCH₃—CHCH₃—(CH₂)₂— | —CH₃ | —CH₃ | H |
|  | —(CH₂)₂—CHOCH₃(CH₂)₂— | —CH₃ | —CH₃ | H |
|  | —(CH₂)₂—CHOC₂H₅—(CH₂)₂— | —CH₃ | —CH₃ | H |
| —CH₃ | —CH₃ | Cl | F | H |
| —C₂H₅ | —CH₃ | Cl | F | H |
| —CH(CH₃)₂ | —CH₃ | Cl | F | H |
| —CF₃ | —CH₃ | Cl | F | H |
|  | —(CH₂)₄— | Cl | F | H |
|  | —(CH₂)₅— | Cl | F | H |
|  | —(CH₂)₆— | Cl | F | H |
|  | —CH₂—CH(CH₃)—(CH₂)₃— | Cl | F | H |
|  | —(CH₂)₂—CH(CH₃)—(CH₂)₂— | Cl | F | H |
|  | —(CH₂)₂—CH(C₂H₅)—(CH₂)₂— | Cl | F | H |
|  | —(CH₂)₂—CH(i-C₃H₇)—(CH₂)₂— | Cl | F | H |
|  | —(CH₂)₂—CHOCH₃—(CH₂)₂— | Cl | F | H |
| —CH₃ | —CH₃ | —Cl | —CF₃ | 6-Cl |
| —C₂H₅ | —CH₃ | —Cl | —CF₃ | 6-Cl |
| —CH(CH₃)₂ | —CH₃ | —Cl | —CF₃ | 6-Cl |
| —CF₃ | —CH₃ | —Cl | —CF₃ | 6-Cl |
|  | —(CH₂)₄— | —Cl | —CF₃ | 6-Cl |
|  | —(CH₂)₅— | —Cl | —CF₃ | 6-Cl |
|  | —(CH₂)₆— | —Cl | —CF₃ | 6-Cl |
|  | —CH₂—CH(CH₃)—(CH₂)₃— | —Cl | —CF₃ | 6-Cl |
|  | —(CH₂)₂—CH(CH₃)—(CH₂)₂— | —Cl | —CF₃ | 6-Cl |

-continued

| A | B | X | Y | $Z_n$ |
|---|---|---|---|---|
| | —(CH$_2$)$_2$—CH(C$_2$H$_5$)—(CH$_2$)$_2$— | —Cl | —CF$_3$ | 6-Cl |
| | —(CH$_2$)$_2$—CH(i-C$_3$H$_7$)—(CH$_2$)$_2$— | —Cl | —CF$_3$ | 6-Cl |
| | —(CH$_2$)$_2$—CHOCH$_3$—(CH$_2$)$_2$— | —Cl | —CF$_3$ | 6-Cl |

In addition to the compounds mentioned in the preparation examples, the following 3-aryl-4-hydroxy-$\Delta^3$-dihydrothiophen-2-one derivatives of formula (Ib) may be mentioned individually (Table 2):

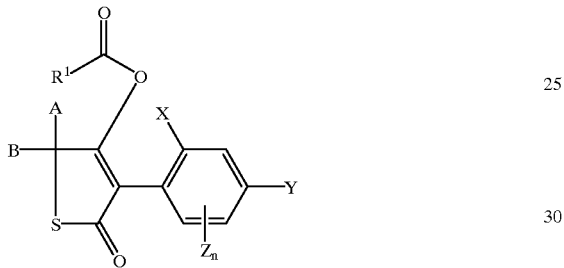

(Ib)

TABLE 2

| A | B | X | Y | $Z_n$ | R$^1$ |
|---|---|---|---|---|---|
| —CH$_3$ | —CH$_3$ | —CH$_3$ | —CH$_3$ | 6-CH$_3$ | —CH$_3$ |
| —CH$_3$ | —CH$_3$ | —CH$_3$ | —CH$_3$ | 6-CH$_3$ | —C$_2$H$_5$ |
| —CH$_3$ | —CH$_3$ | —CH$_3$ | —CH$_3$ | 6-CH$_3$ | —C$_3$H$_7$ |
| —CH$_3$ | —CH$_3$ | —CH$_3$ | —CH$_3$ | 6-CH$_3$ | —C$_4$H$_9$ |
| —CH$_3$ | —CH$_3$ | —CH$_3$ | —CH$_3$ | 6-CH$_3$ | —CH(CH$_3$)$_2$ |
| —CH$_3$ | —CH$_3$ | —CH$_3$ | —CH$_3$ | 6-CH$_3$ | —CH$_2$CH(CH$_3$)$_2$ |
| —CH$_3$ | —CH$_3$ | —CH$_3$ | —CH$_3$ | 6-CH$_3$ | —C(CH$_3$)$_3$ |
| —CH$_3$ | —CH$_3$ | —CH$_3$ | —CH$_3$ | 6-CH$_3$ | —C(CH$_3$)$_2$—C$_2$H$_5$ |
| —CH$_3$ | —CH$_3$ | —CH$_3$ | —CH$_3$ | 6-CH$_3$ | —C(CH$_3$)$_2$—CH(CH$_3$)$_2$ |
| —CH$_3$ | —CH$_3$ | —CH$_3$ | —CH$_3$ | 6-CH$_3$ | —CH$_2$—C(CH$_3$)$_3$ |
| —CH$_3$ | —CH$_3$ | —CH$_3$ | —CH$_3$ | 6-CH$_3$ | —CH(C$_2$H$_5$)—C$_4$H$_9$ |
| —CH$_3$ | —CH$_3$ | —CH$_3$ | —CH$_3$ | 6-CH$_3$ | —C(CH$_3$)$_2$—CH$_2$Cl |
| —CH$_3$ | —CH$_3$ | —CH$_3$ | —CH$_3$ | 6-CH$_3$ | —C(CH$_2$Cl)$_2$CH$_3$ |
| —C$_2$H$_5$ | —CH$_3$ | —CH$_3$ | —CH$_3$ | 6-CH$_3$ | —CH$_3$ |
| —C$_2$H$_5$ | —CH$_3$ | —CH$_3$ | —CH$_3$ | 6-CH$_3$ | —C$_2$H$_5$ |
| —C$_2$H$_5$ | —CH$_3$ | —CH$_3$ | —CH$_3$ | 6-CH$_3$ | —C$_3$H$_7$ |
| —C$_2$H$_5$ | —CH$_3$ | —CH$_3$ | —CH$_3$ | 6-CH$_3$ | —C$_4$H$_9$ |
| —C$_2$H$_5$ | —CH$_3$ | —CH$_3$ | —CH$_3$ | 6-CH$_3$ | —CH(CH$_3$)$_2$ |
| —C$_2$H$_5$ | —CH$_3$ | —CH$_3$ | —CH$_3$ | 6-CH$_3$ | —CH$_2$CH(CH$_3$)$_2$ |
| —C$_2$H$_5$ | —CH$_3$ | —CH$_3$ | —CH$_3$ | 6-CH$_3$ | —C(CH$_3$)$_3$ |
| —C$_2$H$_5$ | —CH$_3$ | —CH$_3$ | —CH$_3$ | 6-CH$_3$ | —C(CH$_3$)$_2$—C$_2$H$_5$ |
| —C$_2$H$_5$ | —CH$_3$ | —CH$_3$ | —CH$_3$ | 6-CH$_3$ | —C(CH$_3$)$_2$—CH(CH$_3$)$_2$ |
| —C$_2$H$_5$ | —CH$_3$ | —CH$_3$ | —CH$_3$ | 6-CH$_3$ | —CH$_2$—C(CH$_3$)$_3$ |

TABLE 2-continued

| A | B | X | Y | $Z_n$ | $R^1$ |
|---|---|---|---|---|---|
| —$C_2H_5$ | —$CH_3$ | —$CH_3$ | —$CH_3$ | 6-$CH_3$ | —CH(—$C_2H_5$)—$C_4H_9$ |
| —$C_2H_5$ | —$CH_3$ | —$CH_3$ | —$CH_3$ | 6-$CH_3$ | —$C(CH_3)_2$—$CH_2Cl$ |
| —$C_2H_5$ | —$CH_3$ | —$CH_3$ | —$CH_3$ | 6-$CH_3$ | —C($CH_3$)($CH_2Cl)_2$ |
| —$C_2H_5$ | —$CH_3$ | —$CH_3$ | —$CH_3$ | 6-$CH_3$ | —$C(CH_3)_2$—$CH_2OCH_3$ |
| —$C_2H_5$ | —$CH_3$ | —$CH_3$ | —$CH_3$ | 6-$CH_3$ | —$C(CH_3)$—$(CH$—$OCH_3)_2$ |
| —$C_2H_5$ | —$CH_3$ | —$CH_3$ | —$CH_3$ | 6-$CH_3$ | —CH=C($CH_3)_2$ |
| —$C_2H_5$ | —$CH_3$ | —$CH_3$ | —$CH_3$ | 6-$CH_3$ |  |
| —$C_2H_5$ | —$CH_3$ | —$CH_3$ | —$CH_3$ | 6-$CH_3$ |  |
| —$C_2H_5$ | —$CH_3$ | —$CH_3$ | —$CH_3$ | 6-$CH_3$ |  |
| —$C_2H_5$ | —$CH_3$ | —$CH_3$ | —$CH_3$ | 6-$CH_3$ | 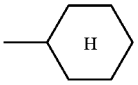 |
| —$C_2H_5$ | —$CH_3$ | —$CH_3$ | —$CH_3$ | 6-$CH_3$ | 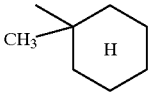 |
| —$C_2H_5$ | —$CH_3$ | —$CH_3$ | —$CH_3$ | 6-$CH_3$ | 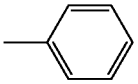 |
| —$C_2H_5$ | —$CH_3$ | —$CH_3$ | —$CH_3$ | 6-$CH_3$ | 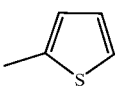 |
| —$C_2H_5$ | —$CH_3$ | —$CH_3$ | —$CH_3$ | 6-$CH_3$ | 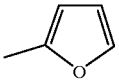 |
| —CH($CH_3)_2$ | —$CH_3$ | —$CH_3$ | —$CH_3$ | 6-$CH_3$ | —$CH_3$ |
| —CH($CH_3)_2$ | —$CH_3$ | —$CH_3$ | —$CH_3$ | 6-$CH_3$ | —$C_2H_5$ |
| —CH($CH_3)_2$ | —$CH_3$ | —$CH_3$ | —$CH_3$ | 6-$CH_3$ | —$C_3H_7$ |
| —CH($CH_3)_2$ | —$CH_3$ | —$CH_3$ | —$CH_3$ | 6-$CH_3$ | —$C_4H_9$ |
| —CH($CH_3)_2$ | —$CH_3$ | —$CH_3$ | —$CH_3$ | 6-$CH_3$ | —CH($CH_3)_2$ |
| —CH($CH_3)_2$ | —$CH_3$ | —$CH_3$ | —$CH_3$ | 6-$CH_3$ | —$CH_2CH(CH_3)_2$ |
| —CH($CH_3)_2$ | —$CH_3$ | —$CH_3$ | —$CH_3$ | 6-$CH_3$ | —$C(CH_3)_3$ |
| —CH($CH_3)_2$ | —$CH_3$ | —$CH_3$ | —$CH_3$ | 6-$CH_3$ | —$C(CH_3)_2$—$C_2H_5$ |

TABLE 2-continued

| A | B | X | Y | $Z_n$ | $R^1$ |
|---|---|---|---|---|---|
| —CH(CH$_3$)$_2$ | —CH$_3$ | —CH$_3$ | —CH$_3$ | 6-CH$_3$ | —C(CH$_3$)$_2$—CH(CH$_3$)$_2$ |
| —CH(CH$_3$)$_2$ | —CH$_3$ | —CH$_3$ | —CH$_3$ | 6-CH$_3$ | —CH$_2$—C(CH$_3$)$_3$ |
| —CH(CH$_3$)$_2$ | —CH$_3$ | —CH$_3$ | —CH$_3$ | 6-CH$_3$ | —CH(C$_4$H$_9$)(C$_2$H$_5$) |
| —CH(CH$_3$)$_2$ | —CH$_3$ | —CH$_3$ | —CH$_3$ | 6-CH$_3$ | —C(CH$_3$)$_2$—CH$_2$Cl |
| —CH(CH$_3$)$_2$ | —CH$_3$ | —CH$_3$ | —CH$_3$ | 6-CH$_3$ | —C(CH$_2$Cl)$_2$(CH$_3$) |
| —CH(CH$_3$)$_2$ | —CH$_3$ | —CH$_3$ | —CH$_3$ | 6-CH$_3$ | —C(CH$_3$)$_2$—CH$_2$OCH$_3$ |
| —CH(CH$_3$)$_2$ | —CH$_3$ | —CH$_3$ | —CH$_3$ | 6-CH$_3$ | —C(CH$_3$)—(CH—OCH$_3$)$_2$ |
| —CH(CH$_3$)$_2$ | —CH$_3$ | —CH$_3$ | —CH$_3$ | 6-CH$_3$ | —CH=C(CH$_3$)$_2$ |
| —CH(CH$_3$)$_2$ | —CH$_3$ | —CH$_3$ | —CH$_3$ | 6-CH$_3$ | 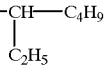 |
| —CH(CH$_3$)$_2$ | —CH$_3$ | —CH$_3$ | —CH$_3$ | 6-CH$_3$ | 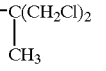 |
| —CH(CH$_3$)$_2$ | —CH$_3$ | —CH$_3$ | —CH$_3$ | 6-CH$_3$ | 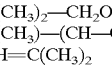 |
| —CH(CH$_3$)$_2$ | —CH$_3$ | —CH$_3$ | —CH$_3$ | 6-CH$_3$ |  |
| —CH(CH$_3$)$_2$ | —CH$_3$ | —CH$_3$ | —CH$_3$ | 6-CH$_3$ | 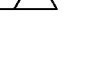 |
| —CH(CH$_3$)$_2$ | —CH$_3$ | —CH$_3$ | —CH$_3$ | 6-CH$_3$ | 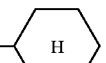 |
| —CH(CH$_3$)$_2$ | —CH$_3$ | —CH$_3$ | —CH$_3$ | 6-CH$_3$ | 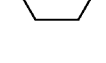 |
| —CH(CH$_3$)$_2$ | —CH$_3$ | —CH$_3$ | —CH$_3$ | 6-CH$_3$ | 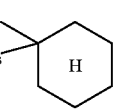 |
| | —(CH$_2$)$_4$— | —CH$_3$ | —CH$_3$ | 6-CH$_3$ | —CH$_3$ |
| | —(CH$_2$)$_4$— | —CH$_3$ | —CH$_3$ | 6-CH$_3$ | —C$_2$H$_5$ |
| | —(CH$_2$)$_4$— | —CH$_3$ | —CH$_3$ | 6-CH$_3$ | —C$_3$H$_7$ |
| | —(CH$_2$)$_4$— | —CH$_3$ | —CH$_3$ | 6-CH$_3$ | —C$_4$H$_9$ |
| | —(CH$_2$)$_4$— | —CH$_3$ | —CH$_3$ | 6-CH$_3$ | —CH(CH$_3$)$_2$ |
| | —(CH$_2$)$_4$— | —CH$_3$ | —CH$_3$ | 6-CH$_3$ | —CH$_2$CH(CH$_3$)$_2$ |

TABLE 2-continued

| A | B | X | Y | $Z_n$ | $R^1$ |
|---|---|---|---|---|---|
|   | —(CH$_2$)$_4$— | —CH$_3$ | —CH$_3$ | 6-CH$_3$ | —C(CH$_3$)$_3$ |
|   | —(CH$_2$)$_4$— | —CH$_3$ | —CH$_3$ | 6-CH$_3$ | —C(CH$_3$)$_2$—C$_2$H$_5$ |
|   | —(CH$_2$)$_4$— | —CH$_3$ | —CH$_3$ | 6-CH$_3$ | —C(CH$_3$)$_2$—CH(CH$_3$)$_2$ |
|   | —(CH$_2$)$_4$— | —CH$_3$ | —CH$_3$ | 6-CH$_3$ | —CH$_2$—C(CH$_3$)$_3$ |
|   | —(CH$_2$)$_4$— | —CH$_3$ | —CH$_3$ | 6-CH$_3$ | —CH(C$_2$H$_5$)—C$_4$H$_9$ |
|   | —(CH$_2$)$_4$— | —CH$_3$ | —CH$_3$ | 6-CH$_3$ | —C(CH$_3$)$_2$—CH$_2$Cl |
|   | —(CH$_2$)$_4$— | —CH$_3$ | —CH$_3$ | 6-CH$_3$ | —C(CH$_3$)(CH$_2$Cl)$_2$ |
|   | —(CH$_2$)$_4$— | —CH$_3$ | —CH$_3$ | 6-CH$_3$ | —C(CH$_3$)$_2$—CH$_2$OCH$_3$ |
|   | —(CH$_2$)$_4$— | —CH$_3$ | —CH$_3$ | 6-CH$_3$ | —C(CH$_3$)—(CH—OCH$_3$)$_2$ |
|   | —(CH$_2$)$_4$— | —CH$_3$ | —CH$_3$ | 6-CH$_3$ | —CH=C(CH$_3$)$_2$ |
|   | —(CH$_2$)$_4$— | —CH$_3$ | —CH$_3$ | 6-CH$_3$ | cyclopropyl |
|   | —(CH$_2$)$_4$— | —CH$_3$ | —CH$_3$ | 6-CH$_3$ | cyclohexyl |
|   | —(CH$_2$)$_4$— | —CH$_3$ | —CH$_3$ | 6-CH$_3$ | 1-methylcyclohexyl |
|   | —(CH$_2$)$_4$— | —CH$_3$ | —CH$_3$ | 6-CH$_3$ | phenyl |
|   | —(CH$_2$)$_4$— | —CH$_3$ | —CH$_3$ | 6-CH$_3$ | 2-thienyl |
|   | —(CH$_2$)$_4$— | —CH$_3$ | —CH$_3$ | 6-CH$_3$ | 2-furyl |
|   | —(CH$_2$)$_4$— | —CH$_3$ | —CH$_3$ | 6-CH$_3$ | —CH$_2$-phenyl |
|   | —(CH$_2$)$_4$— | —CH$_3$ | —CH$_3$ | 6-CH$_3$ | 3-pyridyl |
|   | —(CH$_2$)$_5$— | —CH$_3$ | —CH$_3$ | 6-CH$_3$ | —CH$_3$ |
|   | —(CH$_2$)$_5$— | —CH$_3$ | —CH$_3$ | 6-CH$_3$ | —C$_2$H$_5$ |
|   | —(CH$_2$)$_5$— | —CH$_3$ | —CH$_3$ | 6-CH$_3$ | —C$_3$H$_7$ |
|   | —(CH$_2$)$_5$— | —CH$_3$ | —CH$_3$ | 6-CH$_3$ | —C$_4$H$_9$ |

TABLE 2-continued

| A | B | X | Y | $Z_n$ | $R^1$ |
|---|---|---|---|---|---|
|  | —(CH$_2$)$_5$— | —CH$_3$ | —CH$_3$ | 6-CH$_3$ | —CH(CH$_3$)$_2$ |
|  | —(CH$_2$)$_5$— | —CH$_3$ | —CH$_3$ | 6-CH$_3$ | —CH$_2$CH(CH$_3$)$_2$ |
|  | —(CH$_2$)$_5$— | —CH$_3$ | —CH$_3$ | 6-CH$_3$ | —C(CH$_3$)$_3$ |
|  | —(CH$_2$)$_5$— | —CH$_3$ | —CH$_3$ | 6-CH$_3$ | —C(CH$_3$)$_2$—C$_2$H$_5$ |
|  | —(CH$_2$)$_5$— | —CH$_3$ | —CH$_3$ | 6-CH$_3$ | —C(CH$_3$)$_2$—CH(CH$_3$)$_2$ |
|  | —(CH$_2$)$_5$— | —CH$_3$ | —CH$_3$ | 6-CH$_3$ | —CH$_2$—C(CH$_3$)$_3$ |
|  | —(CH$_2$)$_5$— | —CH$_3$ | —CH$_3$ | 6-CH$_3$ | —CH(C$_2$H$_5$)—C$_4$H$_9$ |
|  | —(CH$_2$)$_5$— | —CH$_3$ | —CH$_3$ | 6-CH$_3$ | —C(CH$_3$)$_2$—CH$_2$Cl |
|  | —(CH$_2$)$_5$— | —CH$_3$ | —CH$_3$ | 6-CH$_3$ | —C(CH$_3$)(CH$_2$Cl)$_2$ |
|  | —(CH$_2$)$_5$— | —CH$_3$ | —CH$_3$ | 6-CH$_3$ | —C(CH$_3$)$_2$—CH$_2$OCH$_3$ |
|  | —(CH$_2$)$_5$— | —CH$_3$ | —CH$_3$ | 6-CH$_3$ | —C(CH$_3$)—(CH—OCH$_3$)$_2$ |
|  | —(CH$_2$)$_5$— | —CH$_3$ | —CH$_3$ | 6-CH$_3$ | —CH═C(CH$_3$)$_2$ |
|  | —(CH$_2$)$_5$— | —CH$_3$ | —CH$_3$ | 6-CH$_3$ | cyclopropyl |
|  | —(CH$_2$)$_5$— | —CH$_3$ | —CH$_3$ | 6-CH$_3$ | cyclohexyl |
|  | —(CH$_2$)$_5$— | —CH$_3$ | —CH$_3$ | 6-CH$_3$ | 1-methylcyclohexyl |
|  | —(CH$_2$)$_5$— | —CH$_3$ | —CH$_3$ | 6-CH$_3$ | phenyl |
|  | —(CH$_2$)$_5$— | —CH$_3$ | —CH$_3$ | 6-CH$_3$ | 2-thienyl |
|  | —(CH$_2$)$_5$— | —CH$_3$ | —CH$_3$ | 6-CH$_3$ | 2-furyl |
|  | —(CH$_2$)$_5$— | —CH$_3$ | —CH$_3$ | 6-CH$_3$ | —CH$_2$-phenyl |
|  | —(CH$_2$)$_5$— | —CH$_3$ | —CH$_3$ | 6-CH$_3$ | 3-pyridyl |
|  | —(CH$_2$)$_6$— | —CH$_3$ | —CH$_3$ | 6-CH$_3$ | —CH$_3$ |
|  | —(CH$_2$)$_6$— | —CH$_3$ | —CH$_3$ | 6-CH$_3$ | —C$_2$H$_5$ |

TABLE 2-continued

| A | B | X | Y | $Z_n$ | $R^1$ |
|---|---|---|---|---|---|
|  | —(CH$_2$)$_6$— | —CH$_3$ | —CH$_3$ | 6-CH$_3$ | —C$_3$H$_7$ |
|  | —(CH$_2$)$_6$— | —CH$_3$ | —CH$_3$ | 6-CH$_3$ | —C$_4$H$_9$ |
|  | —(CH$_2$)$_6$— | —CH$_3$ | —CH$_3$ | 6-CH$_3$ | —CH(CH$_3$)$_2$ |
|  | —(CH$_2$)$_6$— | —CH$_3$ | —CH$_3$ | 6-CH$_3$ | —CH$_2$CH(CH$_3$)$_2$ |
|  | —(CH$_2$)$_6$— | —CH$_3$ | —CH$_3$ | 6-CH$_3$ | —C(CH$_3$)$_3$ |
|  | —(CH$_2$)$_6$— | —CH$_3$ | —CH$_3$ | 6-CH$_3$ | —C(CH$_3$)$_2$—C$_2$H$_5$ |
|  | —(CH$_2$)$_6$— | —CH$_3$ | —CH$_3$ | 6-CH$_3$ | —C(CH$_3$)$_2$—CH(CH$_3$)$_2$ |
|  | —(CH$_2$)$_6$— | —CH$_3$ | —CH$_3$ | 6-CH$_3$ | —CH$_2$—C(CH$_3$)$_3$ |
|  | —(CH$_2$)$_6$— | —CH$_3$ | —CH$_3$ | 6-CH$_3$ | —CH(C$_2$H$_5$)—C$_4$H$_9$ |
|  | —(CH$_2$)$_6$— | —CH$_3$ | —CH$_3$ | 6-CH$_3$ | —C(CH$_3$)$_2$—CH$_2$Cl |
|  | —(CH$_2$)$_6$— | —CH$_3$ | —CH$_3$ | 6-CH$_3$ | —C(CH$_3$)(CH$_2$Cl)$_2$ |
|  | —(CH$_2$)$_6$— | —CH$_3$ | —CH$_3$ | 6-CH$_3$ | —C(CH$_3$)$_2$—CH$_2$OCH$_3$ |
|  | —(CH$_2$)$_6$— | —CH$_3$ | —CH$_3$ | 6-CH$_3$ | —C(CH$_3$)—(CH—OCH$_3$)$_2$ |
|  | —(CH$_2$)$_6$— | —CH$_3$ | —CH$_3$ | 6-CH$_3$ | —CH=C(CH$_3$)$_2$ |
|  | —(CH$_2$)$_6$— | —CH$_3$ | —CH$_3$ | 6-CH$_3$ |  |
|  | —(CH$_2$)$_6$— | —CH$_3$ | —CH$_3$ | 6-CH$_3$ | 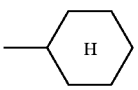 |
|  | —(CH$_2$)$_6$— | —CH$_3$ | —CH$_3$ | 6-CH$_3$ | 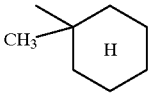 |
|  | —(CH$_2$)$_6$— | —CH$_3$ | —CH$_3$ | 6-CH$_3$ | 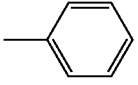 |
|  | —(CH$_2$)$_6$— | —CH$_3$ | —CH$_3$ | 6-CH$_3$ | 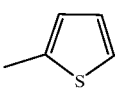 |
|  | —(CH$_2$)$_6$— | —CH$_3$ | —CH$_3$ | 6-CH$_3$ | 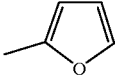 |
|  | —(CH$_2$)$_6$— | —CH$_3$ | —CH$_3$ | 6-CH$_3$ | 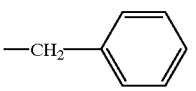 |
|  | —(CH$_2$)$_6$— | —CH$_3$ | —CH$_3$ | 6-CH$_3$ | 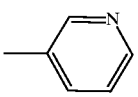 |

TABLE 2-continued

| A | B | X | Y | $Z_n$ | $R^1$ |
|---|---|---|---|---|---|
| | —CH$_2$—CH(CH$_3$)—(CH$_2$)$_3$— | —CH$_3$ | —CH$_3$ | 6-CH$_3$ | —CH$_3$ |
| | —CH$_2$—CH(CH$_3$)—(CH$_2$)$_3$— | —CH$_3$ | —CH$_3$ | 6-CH$_3$ | —C$_2$H$_5$ |
| | —CH$_2$—CH(CH$_3$)—(CH$_2$)$_3$— | —CH$_3$ | —CH$_3$ | 6-CH$_3$ | —C$_3$H$_7$ |
| | —CH$_2$—CH(CH$_3$)—(CH$_2$)$_3$— | —CH$_3$ | —CH$_3$ | 6-CH$_3$ | —C$_4$H$_9$ |
| | —CH$_2$—CH(CH$_3$)—(CH$_2$)$_3$— | —CH$_3$ | —CH$_3$ | 6-CH$_3$ | —CH(CH$_3$)$_2$ |
| | —CH$_2$—CH(CH$_3$)—(CH$_2$)$_3$— | —CH$_3$ | —CH$_3$ | 6-CH$_3$ | —CH$_2$CH(CH$_3$)$_2$ |
| | —CH$_2$—CH(CH$_3$)—(CH$_2$)$_3$— | —CH$_3$ | —CH$_3$ | 6-CH$_3$ | —C(CH$_3$)$_3$ |
| | —CH$_2$—CH(CH$_3$)—(CH$_2$)$_3$— | —CH$_3$ | —CH$_3$ | 6-CH$_3$ | —C(CH$_3$)$_2$—C$_2$H$_5$ |
| | —CH$_2$—CH(CH$_3$)—(CH$_2$)$_3$— | —CH$_3$ | —CH$_3$ | 6-CH$_3$ | —C(CH$_3$)$_2$—CH(CH$_3$)$_2$ |
| | —CH$_2$—CH(CH$_3$)—(CH$_2$)$_3$— | —CH$_3$ | —CH$_3$ | 6-CH$_3$ | —CH$_2$—C(CH$_3$)$_3$ |
| | —CH$_2$—CH(CH$_3$)—(CH$_2$)$_3$— | —CH$_3$ | —CH$_3$ | 6-CH$_3$ | —CH(C$_2$H$_5$)—C$_4$H$_9$ |
| | —CH$_2$—CH(CH$_3$)—(CH$_2$)$_3$— | —CH$_3$ | —CH$_3$ | 6-CH$_3$ | —C(CH$_3$)$_2$—CH$_2$Cl |
| | —CH$_2$—CH(CH$_3$)—(CH$_2$)$_3$— | —CH$_3$ | —CH$_3$ | 6-CH$_3$ | —C(CH$_2$Cl)$_2$(CH$_3$) |
| | —CH$_2$—CH(CH$_3$)—(CH$_2$)$_3$— | —CH$_3$ | —CH$_3$ | 6-CH$_3$ | —C(CH$_3$)$_2$—CH$_2$OCH$_3$ |
| | —CH$_2$—CH(CH$_3$)—(CH$_2$)$_3$— | —CH$_3$ | —CH$_3$ | 6-CH$_3$ | —C(CH$_3$)—(CH—OCH$_3$)$_2$ |
| | —CH$_2$—CH(CH$_3$)—(CH$_2$)$_3$— | —CH$_3$ | —CH$_3$ | 6-CH$_3$ | —CH═C(CH$_3$)$_2$ |
| | —CH$_2$—CH(CH$_3$)—(CH$_2$)$_3$— | —CH$_3$ | —CH$_3$ | 6-CH$_3$ | cyclopropyl |
| | —CH$_2$—CH(CH$_3$)—(CH$_2$)$_3$— | —CH$_3$ | —CH$_3$ | 6-CH$_3$ | cyclohexyl |
| | —CH$_2$—CH(CH$_3$)—(CH$_2$)$_3$— | —CH$_3$ | —CH$_3$ | 6-CH$_3$ | 1-methylcyclohexyl |
| | —CH$_2$—CH(CH$_3$)—(CH$_2$)$_3$— | —CH$_3$ | —CH$_3$ | 6-CH$_3$ | phenyl |
| | —CH$_2$—CH(CH$_3$)—(CH$_2$)$_3$— | —CH$_3$ | —CH$_3$ | 6-CH$_3$ | 2-thienyl |
| | —CH$_2$—CH(CH$_3$)—(CH$_2$)$_3$— | —CH$_3$ | —CH$_3$ | 6-CH$_3$ | 2-furyl |
| | —CH$_2$—CH(CH$_3$)—(CH$_2$)$_3$— | —CH$_3$ | —CH$_3$ | 6-CH$_3$ | —CH$_2$-phenyl |

TABLE 2-continued

| A | B | X | Y | $Z_n$ | $R^1$ |
|---|---|---|---|---|---|
| | —CH₂—CH(CH₃)—(CH₂)₃— | —CH₃ | —CH₃ | 6-CH₃ | 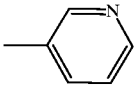 (3-pyridyl) |
| | —(CH₂)₂—CH(CH₃)—(CH₂)₂— | —CH₃ | —CH₃ | 6-CH₃ | —CH₃ |
| | —(CH₂)₂—CH(CH₃)—(CH₂)₂— | —CH₃ | —CH₃ | 6-CH₃ | —C₂H₅ |
| | —(CH₂)₂—CH(CH₃)—(CH₂)₂— | —CH₃ | —CH₃ | 6-CH₃ | —C₃H₇ |
| | —(CH₂)₂—CH(CH₃)—(CH₂)₂— | —CH₃ | —CH₃ | 6-CH₃ | —C₄H₉ |
| | —(CH₂)₂—CH(CH₃)—(CH₂)₂— | —CH₃ | —CH₃ | 6-CH₃ | —CH(CH₃)₂ |
| | —(CH₂)₂—CH(CH₃)—(CH₂)₂— | —CH₃ | —CH₃ | 6-CH₃ | —CH₂CH(CH₃)₂ |
| | —(CH₂)₂—CH(CH₃)—(CH₂)₂— | —CH₃ | —CH₃ | 6-CH₃ | —C(CH₃)₃ |
| | —(CH₂)₂—CH(CH₃)—(CH₂)₂— | —CH₃ | —CH₃ | 6-CH₃ | —C(CH₃)₂—C₂H₅ |
| | —(CH₂)₂—CH(CH₃)—(CH₂)₂— | —CH₃ | —CH₃ | 6-CH₃ | —C(CH₃)₂—CH(CH₃)₂ |
| | —(CH₂)₂—CH(CH₃)—(CH₂)₂— | —CH₃ | —CH₃ | 6-CH₃ | —CH₂—C(CH₃)₃ |
| | —(CH₂)₂—CH(CH₃)—(CH₂)₂— | —CH₃ | —CH₃ | 6-CH₃ | —CH(C₂H₅)—C₄H₉ |
| | —(CH₂)₂—CH(CH₃)—(CH₂)₂— | —CH₃ | —CH₃ | 6-CH₃ | —C(CH₃)₂—CH₂Cl |
| | —(CH₂)₂—CH(CH₃)—(CH₂)₂— | —CH₃ | —CH₃ | 6-CH₃ | —C(CH₃)(CH₂Cl)₂ |
| | —(CH₂)₂—CH(CH₃)—(CH₂)₂— | —CH₃ | —CH₃ | 6-CH₃ | —C(CH₃)₂—CH₂OCH₃ |
| | —(CH₂)₂—CH(CH₃)—(CH₂)₂— | —CH₃ | —CH₃ | 6-CH₃ | —C(CH₃)—(CH—OCH₃)₂ |
| | —(CH₂)₂—CH(CH₃)—(CH₂)₂— | —CH₃ | —CH₃ | 6-CH₃ | —CH=C(CH₃)₂ |
| | —(CH₂)₂—CH(CH₃)—(CH₂)₂— | —CH₃ | —CH₃ | 6-CH₃ |  (cyclopropyl) |
| | —(CH₂)₂—CH(CH₃)—(CH₂)₂— | —CH₃ | —CH₃ | 6-CH₃ |  (cyclohexyl) |
| | —(CH₂)₂—CH(CH₃)—(CH₂)₂— | —CH₃ | —CH₃ | 6-CH₃ |  (1-methylcyclohexyl) |
| | —(CH₂)₂—CH(CH₃)—(CH₂)₂— | —CH₃ | —CH₃ | 6-CH₃ | 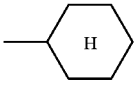 (phenyl) |
| | —(CH₂)₂—CH(CH₃)—(CH₂)₂— | —CH₃ | —CH₃ | 6-CH₃ | 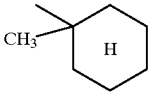 (2-thienyl) |
| | —(CH₂)₂—CH(CH₃)—(CH₂)₂— | —CH₃ | —CH₃ | 6-CH₃ | 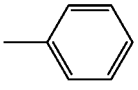 (2-furyl) |

TABLE 2-continued

| A | B | X | Y | $Z_n$ | $R^1$ |
|---|---|---|---|---|---|
| | —(CH$_2$)$_2$—CH(CH$_3$)—(CH$_2$)$_2$— | —CH$_3$ | —CH$_3$ | 6-CH$_3$ | 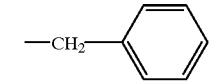 |
| | —(CH$_2$)$_2$—CH(CH$_3$)—(CH$_2$)$_2$— | —CH$_3$ | —CH$_3$ | 6-CH$_3$ | 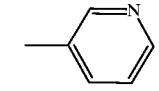 |
| | —(CH$_2$)$_2$—CH(OCH$_3$)—(CH$_2$)$_2$— | —CH$_3$ | —CH$_3$ | 6-CH$_3$ | —CH$_3$ |
| | —(CH$_2$)$_2$—CH(OCH$_3$)—(CH$_2$)$_2$— | —CH$_3$ | —CH$_3$ | 6-CH$_3$ | —C$_2$H$_5$ |
| | —(CH$_2$)$_2$—CH(OCH$_3$)—(CH$_2$)$_2$— | —CH$_3$ | —CH$_3$ | 6-CH$_3$ | —C$_3$H$_7$ |
| | —(CH$_2$)$_2$—CH(OCH$_3$)—(CH$_2$)$_2$— | —CH$_3$ | —CH$_3$ | 6-CH$_3$ | —C$_4$H$_9$ |
| | —(CH$_2$)$_2$—CH(OCH$_3$)—(CH$_2$)$_2$— | —CH$_3$ | —CH$_3$ | 6-CH$_3$ | —CH(CH$_3$)$_2$ |
| | —(CH$_2$)$_2$—CH(OCH$_3$)—(CH$_2$)$_2$— | —CH$_3$ | —CH$_3$ | 6-CH$_3$ | —CH$_2$CH(CH$_3$)$_2$ |
| | —(CH$_2$)$_2$—CH(OCH$_3$)—(CH$_2$)$_2$— | —CH$_3$ | —CH$_3$ | 6-CH$_3$ | —C(CH$_3$)$_3$ |
| | —(CH$_2$)$_2$—CH(OCH$_3$)—(CH$_2$)$_2$— | —CH$_3$ | —CH$_3$ | 6-CH$_3$ | —C(CH$_3$)$_2$—C$_2$H$_5$ |
| | —(CH$_2$)$_2$—CH(OCH$_3$)—(CH$_2$)$_2$— | —CH$_3$ | —CH$_3$ | 6-CH$_3$ | —C(CH$_3$)$_2$—CH(CH$_3$)$_2$ |
| | —(CH$_2$)$_2$—CH(OCH$_3$)—(CH$_2$)$_2$— | —CH$_3$ | —CH$_3$ | 6-CH$_3$ | —CH$_2$—C(CH$_3$)$_3$ |
| | —(CH$_2$)$_2$—CH(OCH$_3$)—(CH$_2$)$_2$— | —CH$_3$ | —CH$_3$ | 6-CH$_3$ | —CH(C$_2$H$_5$)—C$_4$H$_9$ |
| | —(CH$_2$)$_2$—CH(OCH$_3$)—(CH$_2$)$_2$— | —CH$_3$ | —CH$_3$ | 6-CH$_3$ | —C(CH$_3$)$_2$—CH$_2$Cl |
| | —(CH$_2$)$_2$—CH(OCH$_3$)—(CH$_2$)$_2$— | —CH$_3$ | —CH$_3$ | 6-CH$_3$ | —C(CH$_2$Cl)$_2$CH$_3$ |
| | —(CH$_2$)$_2$—CH(OCH$_3$)—(CH$_2$)$_2$— | —CH$_3$ | —CH$_3$ | 6-CH$_3$ | —C(CH$_3$)$_2$—CH$_2$OCH$_3$ |
| | —(CH$_2$)$_2$—CH(OCH$_3$)—(CH$_2$)$_2$— | —CH$_3$ | —CH$_3$ | 6-CH$_3$ | —C(CH$_3$)—(CH—OCH$_3$)$_2$ |
| | —(CH$_2$)$_2$—CH(OCH$_3$)—(CH$_2$)$_2$— | —CH$_3$ | —CH$_3$ | 6-CH$_3$ | —CH=C(CH$_3$)$_2$ |
| | —(CH$_2$)$_2$—CH(OCH$_3$)—(CH$_2$)$_2$— | —CH$_3$ | —CH$_3$ | 6-CH$_3$ | 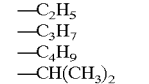 |
| | —(CH$_2$)$_2$—CH(OCH$_3$)—(CH$_2$)$_2$— | —CH$_3$ | —CH$_3$ | 6-CH$_3$ | 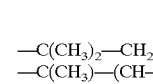 |
| | —(CH$_2$)$_2$—CH(OCH$_3$)—(CH$_2$)$_2$— | —CH$_3$ | —CH$_3$ | 6-CH$_3$ | 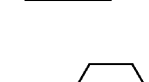 |
| | —(CH$_2$)$_2$—CH(OCH$_3$)—(CH$_2$)$_2$— | —CH$_3$ | —CH$_3$ | 6-CH$_3$ | 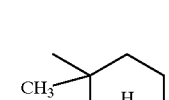 |
| | —(CH$_2$)$_2$—CH(OCH$_3$)—(CH$_2$)$_2$— | —CH$_3$ | —CH$_3$ | 6-CH$_3$ | 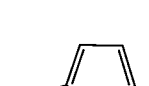 |
| | —(CH$_2$)$_2$—CH(OCH$_3$)—(CH$_2$)$_2$— | —CH$_3$ | —CH$_3$ | 6-CH$_3$ | 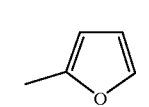 |

TABLE 2-continued

| A | B | X | Y | $Z_n$ | $R^1$ |
|---|---|---|---|---|---|
| | —(CH$_2$)$_2$—CH(OCH$_3$)—(CH$_2$)$_2$— | —CH$_3$ | —CH$_3$ | 6-CH$_3$ | —CH$_2$—C$_6$H$_5$ (benzyl) |
| | —(CH$_2$)$_2$—CH(OCH$_3$)—(CH$_2$)$_2$— | —CH$_3$ | —CH$_3$ | 6-CH$_3$ | 3-pyridylmethyl |
| | —CH$_2$—[CH(CH$_3$)]$_2$—(CH$_2$)$_2$— | —CH$_3$ | —CH$_3$ | 6-CH$_3$ | —CH$_3$ |
| | —CH$_2$—[CH(CH$_3$)]$_2$—(CH$_2$)$_2$— | —CH$_3$ | —CH$_3$ | 6-CH$_3$ | —C$_2$H$_5$ |
| | —CH$_2$—[CH(CH$_3$)]$_2$—(CH$_2$)$_2$— | —CH$_3$ | —CH$_3$ | 6-CH$_3$ | —C$_3$H$_7$ |
| | —CH$_2$—[CH(CH$_3$)]$_2$—(CH$_2$)$_2$— | —CH$_3$ | —CH$_3$ | 6-CH$_3$ | —C$_4$H$_9$ |
| | —CH$_2$—[CH(CH$_3$)]$_2$—(CH$_2$)$_2$— | —CH$_3$ | —CH$_3$ | 6-CH$_3$ | —CH(CH$_3$)$_2$ |
| | —CH$_2$—[CH(CH$_3$)]$_2$—(CH$_2$)$_2$— | —CH$_3$ | —CH$_3$ | 6-CH$_3$ | —CH$_2$CH(CH$_3$)$_2$ |
| | —CH$_2$—[CH(CH$_3$)]$_2$—(CH$_2$)$_2$— | —CH$_3$ | —CH$_3$ | 6-CH$_3$ | —C(CH$_3$)$_3$ |
| | —CH$_2$—[CH(CH$_3$)]$_2$—(CH$_2$)$_2$— | —CH$_3$ | —CH$_3$ | 6-CH$_3$ | —C(CH$_3$)$_2$—C$_2$H$_5$ |
| | —CH$_2$—[CH(CH$_3$)]$_2$—(CH$_2$)$_2$— | —CH$_3$ | —CH$_3$ | 6-CH$_3$ | —C(CH$_3$)$_2$—CH(CH$_3$)$_2$ |
| | —CH$_2$—[CH(CH$_3$)]$_2$—(CH$_2$)$_2$— | —CH$_3$ | —CH$_3$ | 6-CH$_3$ | —CH$_2$—C(CH$_3$)$_3$ |
| | —CH$_2$—[CH(CH$_3$)]$_2$—(CH$_2$)$_2$— | —CH$_3$ | —CH$_3$ | 6-CH$_3$ | —CH(C$_2$H$_5$)—C$_4$H$_9$ |
| | —CH$_2$—[CH(CH$_3$)]$_2$—(CH$_2$)$_2$— | —CH$_3$ | —CH$_3$ | 6-CH$_3$ | —C(CH$_3$)$_2$—CH$_2$Cl |
| | —CH$_2$—[CH(CH$_3$)]$_2$—(CH$_2$)$_2$— | —CH$_3$ | —CH$_3$ | 6-CH$_3$ | —C(CH$_3$)(CH$_2$Cl)$_2$ |
| | —CH$_2$—[CH(CH$_3$)]$_2$—(CH$_2$)$_2$— | —CH$_3$ | —CH$_3$ | 6-CH$_3$ | —C(CH$_3$)$_2$—CH$_2$OCH$_3$ |
| | —CH$_2$—[CH(CH$_3$)]$_2$—(CH$_2$)$_2$— | —CH$_3$ | —CH$_3$ | 6-CH$_3$ | —C(CH$_3$)—(CH—OCH$_3$)$_2$ |
| | —CH$_2$—[CH(CH$_3$)]$_2$—(CH$_2$)$_2$— | —CH$_3$ | —CH$_3$ | 6-CH$_3$ | —CH=C(CH$_3$)$_2$ |
| | —CH$_2$—[CH(CH$_3$)]$_2$—(CH$_2$)$_2$— | —CH$_3$ | —CH$_3$ | 6-CH$_3$ | cyclopropyl |
| | —CH$_2$—[CH(CH$_3$)]$_2$—(CH$_2$)$_2$— | —CH$_3$ | —CH$_3$ | 6-CH$_3$ | cyclohexyl |
| | —CH$_2$—[CH(CH$_3$)]$_2$—(CH$_2$)$_2$— | —CH$_3$ | —CH$_3$ | 6-CH$_3$ | 1-methylcyclohexyl |
| | —CH$_2$—[CH(CH$_3$)]$_2$—(CH$_2$)$_2$— | —CH$_3$ | —CH$_3$ | 6-CH$_3$ | phenyl |
| | —CH$_2$—[CH(CH$_3$)]$_2$—(CH$_2$)$_2$— | —CH$_3$ | —CH$_3$ | 6-CH$_3$ | 2-thienyl |

TABLE 2-continued

| A | B | X | Y | $Z_n$ | $R^1$ |
|---|---|---|---|---|---|
| —CH$_2$—[CH(CH$_3$)]$_2$—(CH$_2$)$_2$— | | —CH$_3$ | —CH$_3$ | 6-CH$_3$ | 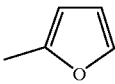 |
| —CH$_2$—[CH(CH$_3$)]$_2$—(CH$_2$)$_2$— | | —CH$_3$ | —CH$_3$ | 6-CH$_3$ | 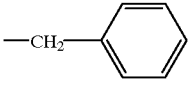 |
| —CH$_2$—[CH(CH$_3$)]$_2$—(CH$_2$)$_2$— | | —CH$_3$ | —CH$_3$ | 6-CH$_3$ | 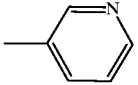 |

Table 3

Table 3 contains the compounds of the formula (Ib) in which A, B and $R^1$ have the meanings mentioned in Table 2 and X and Y in each case represent chlorine and $Z_n$ represents hydrogen.

Table 4

Table 4 contains the compounds of the formula (Ib) in which A, B and $R^1$ have the meanings mentioned in Table 2 and X and Y in each case represent CH$_3$ and $Z_n$ represents hydrogen.

In addition to the compounds mentioned in the preparation examples, the following 3-aryl4-hydroxy-$\Delta^3$-dihydrothiophen-2-one derivatives of the formula (Ic) may be mentioned individually (Table 5):

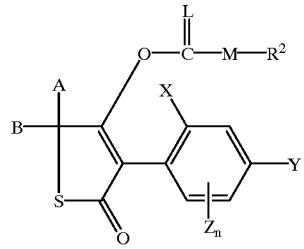

(Ic)

TABLE 5

| A | B | X | Y | $Z_n$ | L | M | $R^2$ |
|---|---|---|---|---|---|---|---|
| —CH$_3$ | —CH$_3$ | —CH$_3$ | —CH$_3$ | 6-CH$_3$ | O | O | —CH$_3$ |
| —C$_2$H$_5$ | —CH$_3$ | —CH$_3$ | —CH$_3$ | 6-CH$_3$ | O | O | —CH$_3$ |
| —CH(CH$_3$)$_2$ | —CH$_3$ | —CH$_3$ | —CH$_3$ | 6-CH$_3$ | O | O | —CH$_3$ |
| —CF$_3$ | —CH$_3$ | —CH$_3$ | —CH$_3$ | 6-CH$_3$ | O | O | —CH$_3$ |
| —(CH$_2$)$_4$— | | —CH$_3$ | —CH$_3$ | 6-CH$_3$ | O | O | —CH$_3$ |
| —(CH$_2$)$_5$— | | —CH$_3$ | —CH$_3$ | 6-CH$_3$ | O | O | —CH$_3$ |
| —(CH$_2$)$_6$— | | —CH$_3$ | —CH$_3$ | 6-CH$_3$ | O | O | —CH$_3$ |
| —CH$_2$—CH(CH$_3$)—(CH$_2$)$_3$— | | —CH$_3$ | —CH$_3$ | 6-CH$_3$ | O | O | —CH$_3$ |
| —(CH$_2$)$_2$—CH(CH$_3$)—(CH$_2$)$_2$— | | —CH$_3$ | —CH$_3$ | 6-CH$_3$ | O | O | —CH$_3$ |
| —(CH$_2$)$_2$—CH(C$_2$H$_5$)—(CH$_2$)$_2$— | | —CH$_3$ | —CH$_3$ | 6-CH$_3$ | O | O | —CH$_3$ |
| —(CH$_2$)$_2$—CH(OCH$_3$)—(CH$_2$)$_2$— | | —CH$_3$ | —CH$_3$ | 6-CH$_3$ | O | O | —CH$_3$ |
| —CH$_3$ | —CH$_3$ | —CH$_3$ | —CH$_3$ | 6-CH$_3$ | O | O | —C$_2$H$_5$ |
| —C$_2$H$_5$ | —CH$_3$ | —CH$_3$ | —CH$_3$ | 6-CH$_3$ | O | O | —C$_2$H$_5$ |
| —CH(CH$_3$)$_2$ | —CH$_3$ | —CH$_3$ | —CH$_3$ | 6-CH$_3$ | O | O | —C$_2$H$_5$ |
| —CF$_3$ | —CH$_3$ | —CH$_3$ | —CH$_3$ | 6-CH$_3$ | O | O | —C$_2$H$_5$ |
| —(CH$_2$)$_4$— | | —CH$_3$ | —CH$_3$ | 6-CH$_3$ | O | O | —C$_2$H$_5$ |
| —(CH$_2$)$_5$— | | —CH$_3$ | —CH$_3$ | 6-CH$_3$ | O | O | —C$_2$H$_5$ |
| —(CH$_2$)$_6$— | | —CH$_3$ | —CH$_3$ | 6-CH$_3$ | O | O | —C$_2$H$_5$ |
| —CH$_2$—CH(CH$_3$)—(CH$_2$)$_3$— | | —CH$_3$ | —CH$_3$ | 6-CH$_3$ | O | O | —C$_2$H$_5$ |
| —(CH$_2$)$_2$—CH(CH$_3$)—(CH$_2$)$_2$— | | —CH$_3$ | —CH$_3$ | 6-CH$_3$ | O | O | —C$_2$H$_5$ |

TABLE 5-continued

| A | B | X | Y | $Z_n$ | L | M | $R^2$ |
|---|---|---|---|---|---|---|---|
| —(CH$_2$)$_2$—CH(C$_2$H$_5$)—(CH$_2$)$_2$— | | —CH$_3$ | —CH$_3$ | 6-CH$_3$ | O | O | —C$_2$H$_5$ |
| —(CH$_2$)$_2$—CH(OCH$_3$)—(CH$_2$)$_2$— | | —CH$_3$ | —CH$_3$ | 6-CH$_3$ | O | O | —C$_2$H$_5$ |
| —CH$_3$ | —CH$_3$ | —CH$_3$ | —CH$_3$ | 6-CH$_3$ | O | O | —CH(CH$_3$)$_2$ |
| —C$_2$H$_5$ | —CH$_3$ | —CH$_3$ | —CH$_3$ | 6-CH$_3$ | O | O | —CH(CH$_3$)$_2$ |
| —CH(CH$_3$)$_2$ | —CH$_3$ | —CH$_3$ | —CH$_3$ | 6-CH$_3$ | O | O | —CH(CH$_3$)$_2$ |
| —CF$_3$ | —CH$_3$ | —CH$_3$ | —CH$_3$ | 6-CH$_3$ | O | O | —CH(CH$_3$)$_2$ |
| —(CH$_2$)$_4$— | | —CH$_3$ | —CH$_3$ | 6-CH$_3$ | O | O | —CH(CH$_3$)$_2$ |
| —(CH$_2$)$_5$— | | —CH$_3$ | —CH$_3$ | 6-CH$_3$ | O | O | —CH(CH$_3$)$_2$ |
| —(CH$_2$)$_6$— | | —CH$_3$ | —CH$_3$ | 6-CH$_3$ | O | O | —CH(CH$_3$)$_2$ |
| —CH$_2$—CH(CH$_3$)—(CH$_2$)$_3$— | | —CH$_3$ | —CH$_3$ | 6-CH$_3$ | O | O | —CH(CH$_3$)$_2$ |
| —(CH$_2$)$_2$—CH(CH$_3$)—(CH$_2$)$_2$— | | —CH$_3$ | —CH$_3$ | 6-CH$_3$ | O | O | —CH(CH$_3$)$_2$ |
| —(CH$_2$)$_2$—CH(C$_2$H$_5$)—(CH$_2$)$_2$— | | —CH$_3$ | —CH$_3$ | 6-CH$_3$ | O | O | —CH(CH$_3$)$_2$ |
| —(CH$_2$)$_2$—CH(OCH$_3$)—(CH$_2$)$_2$— | | —CH$_3$ | —CH$_3$ | 6-CH$_3$ | O | O | —CH(CH$_3$)$_2$ |
| —CH$_3$ | —CH$_3$ | —CH$_3$ | —CH$_3$ | 6-CH$_3$ | O | O | —CH$_2$—CH(CH$_3$)$_2$ |
| —C$_2$H$_5$ | —CH$_3$ | —CH$_3$ | —CH$_3$ | 6-CH$_3$ | O | O | —CH$_2$—CH(CH$_3$)$_2$ |
| —CH(CH$_3$)$_2$ | —CH$_3$ | —CH$_3$ | —CH$_3$ | 6-CH$_3$ | O | O | —CH$_2$—CH(CH$_3$)$_2$ |
| —CF$_3$ | —CH$_3$ | —CH$_3$ | —CH$_3$ | 6-CH$_3$ | O | O | —CH$_2$—CH(CH$_3$)$_2$ |
| —(CH$_2$)$_4$— | | —CH$_3$ | —CH$_3$ | 6-CH$_3$ | O | O | —CH$_2$—CH(CH$_3$)$_2$ |
| —(CH$_2$)$_5$— | | —CH$_3$ | —CH$_3$ | 6-CH$_3$ | O | O | —CH$_2$—CH(CH$_3$)$_2$ |
| —(CH$_2$)$_6$— | | —CH$_3$ | —CH$_3$ | 6-CH$_3$ | O | O | —CH$_2$—CH(CH$_3$)$_2$ |
| —CH$_2$—CH(CH$_3$)—(CH$_2$)$_3$— | | —CH$_3$ | —CH$_3$ | 6-CH$_3$ | O | O | —CH$_2$—CH(CH$_3$)$_2$ |
| —(CH$_2$)$_2$—CH(CH$_3$)—(CH$_2$)$_2$— | | —CH$_3$ | —CH$_3$ | 6-CH$_3$ | O | O | —CH$_2$—CH(CH$_3$)$_2$ |
| —(CH$_2$)$_2$—CH(C$_2$H$_5$)—(CH$_2$)$_2$— | | —CH$_3$ | —CH$_3$ | 6-CH$_3$ | O | O | —CH$_2$—CH(CH$_3$)$_2$ |
| —(CH$_2$)$_2$—CH(OCH$_3$)—(CH$_2$)$_2$— | | —CH$_3$ | —CH$_3$ | 6-CH$_3$ | O | O | —CH$_2$—CH(CH$_3$)$_2$ |
| —CH$_3$ | —CH$_3$ | CH$_3$ | CH$_3$ | 6-CH$_3$ | O | O | —CH(CH$_3$)—C$_2$H$_5$ |
| —C$_2$H$_5$ | —CH$_3$ | CH$_3$ | CH$_3$ | 6-CH$_3$ | O | O | —CH(CH$_3$)—C$_2$H$_5$ |
| —CH(CH$_3$)$_2$ | —CH$_3$ | CH$_3$ | CH$_3$ | 6-CH$_3$ | O | O | —CH(CH$_3$)—C$_2$H$_5$ |
| —CF$_3$ | —CH$_3$ | CH$_3$ | CH$_3$ | 6-CH$_3$ | O | O | —CH(CH$_3$)—C$_2$H$_5$ |
| —(CH$_2$)$_4$— | | CH$_3$ | CH$_3$ | 6-CH$_3$ | O | O | —CH(CH$_3$)—C$_2$H$_5$ |
| —(CH$_2$)$_5$— | | CH$_3$ | CH$_3$ | 6-CH$_3$ | O | O | —CH(CH$_3$)—C$_2$H$_5$ |
| —(CH$_2$)$_6$— | | CH$_3$ | CH$_3$ | 6-CH$_3$ | O | O | —CH(CH$_3$)—C$_2$H$_5$ |
| —CH$_2$—CH(CH$_3$)—(CH$_2$)$_3$— | | CH$_3$ | CH$_3$ | 6-CH$_3$ | O | O | —CH(CH$_3$)—C$_2$H$_5$ |
| —(CH$_2$)$_2$—CH(CH$_3$)—(CH$_2$)$_2$— | | CH$_3$ | CH$_3$ | 6-CH$_3$ | O | O | —CH(CH$_3$)—C$_2$H$_5$ |
| —(CH$_2$)$_2$—CH(C$_2$H$_5$)—(CH$_2$)$_2$— | | CH$_3$ | CH$_3$ | 6-CH$_3$ | O | O | —CH(CH$_3$)—C$_2$H$_5$ |
| —(CH$_2$)$_2$—CH(OCH$_3$)—(CH$_2$)$_2$— | | CH$_3$ | CH$_3$ | 6-CH$_3$ | O | O | —CH(CH$_3$)—C$_2$H$_5$ |
| —CH$_3$ | —CH$_3$ | —CH$_3$ | —CH$_3$ | 6-CH$_3$ | O | O | —CH$_2$—C(CH$_3$)$_3$ |
| —C$_2$H$_5$ | —CH$_3$ | —CH$_3$ | —CH$_3$ | 6-CH$_3$ | O | O | —CH$_2$—C(CH$_3$)$_3$ |
| —CH(CH$_3$)$_2$ | —CH$_3$ | —CH$_3$ | —CH$_3$ | 6-CH$_3$ | O | O | —CH$_2$—C(CH$_3$)$_3$ |
| —CF$_3$ | —CH$_3$ | —CH$_3$ | —CH$_3$ | 6-CH$_3$ | O | O | —CH$_2$—C(CH$_3$)$_3$ |
| —(CH$_2$)$_4$— | | —CH$_3$ | —CH$_3$ | 6-CH$_3$ | O | O | —CH$_2$—C(CH$_3$)$_3$ |
| —(CH$_2$)$_5$— | | —CH$_3$ | —CH$_3$ | 6-CH$_3$ | O | O | —CH$_2$—C(CH$_3$)$_3$ |
| —(CH$_2$)$_6$— | | —CH$_3$ | —CH$_3$ | 6-CH$_3$ | O | O | —CH$_2$—C(CH$_3$)$_3$ |
| —CH$_2$—CH(CH$_3$)—(CH$_2$)$_3$— | | —CH$_3$ | —CH$_3$ | 6-CH$_3$ | O | O | —CH$_2$—C(CH$_3$)$_3$ |
| —(CH$_2$)$_2$—CH(CH$_3$)—(CH$_2$)$_2$— | | —CH$_3$ | —CH$_3$ | 6-CH$_3$ | O | O | —CH$_2$—C(CH$_3$)$_3$ |

TABLE 5-continued

| A | B | X | Y | $Z_n$ | L | M | $R^2$ |
|---|---|---|---|---|---|---|---|
| —(CH$_2$)$_2$—CH(C$_2$H$_5$)—(CH$_2$)$_2$— | | —CH$_3$ | —CH$_3$ | 6-CH$_3$ | O | O | —CH$_2$—C(CH$_3$)$_3$ |
| —(CH$_2$)$_2$—CH(OCH$_3$)—(CH$_2$)$_2$— | | —CH$_3$ | —CH$_3$ | 6-CH$_3$ | O | O | —CH$_2$—C(CH$_3$)$_3$ |
| —CH$_3$ | —CH$_3$ | —CH$_3$ | —CH$_3$ | 6-CH$_3$ | O | O | —CH$_2$—C$_6$H$_5$ |
| —C$_2$H$_5$ | —CH$_3$ | —CH$_3$ | —CH$_3$ | 6-CH$_3$ | O | O | —CH$_2$—C$_6$H$_5$ |
| —CH(CH$_3$)$_2$ | —CH$_3$ | —CH$_3$ | —CH$_3$ | 6-CH$_3$ | O | O | —CH$_2$—C$_6$H$_5$ |
| —CF$_3$ | —CH$_3$ | —CH$_3$ | —CH$_3$ | 6-CH$_3$ | O | O | —CH$_2$—C$_6$H$_5$ |
| —(CH$_2$)$_4$— | | —CH$_3$ | —CH$_3$ | 6-CH$_3$ | O | O | —CH$_2$—C$_6$H$_5$ |
| —(CH$_2$)$_5$— | | —CH$_3$ | —CH$_3$ | 6-CH$_3$ | O | O | —CH$_2$—C$_6$H$_5$ |
| —(CH$_2$)$_6$— | | —CH$_3$ | —CH$_3$ | 6-CH$_3$ | O | O | —CH$_2$—C$_6$H$_5$ |
| —CH$_2$—CH(CH$_3$)—(CH$_2$)$_3$— | | —CH$_3$ | —CH$_3$ | 6-CH$_3$ | O | O | —CH$_2$—C$_6$H$_5$ |
| —(CH$_2$)$_2$—CH(CH$_3$)—(CH$_2$)$_2$— | | —CH$_3$ | —CH$_3$ | 6-CH$_3$ | O | O | —CH$_2$—C$_6$H$_5$ |
| —(CH$_2$)$_2$—CH(C$_2$H$_5$)—(CH$_2$)$_2$— | | —CH$_3$ | —CH$_3$ | 6-CH$_3$ | O | O | —CH$_2$—C$_6$H$_5$ |

TABLE 5-continued

| A | B | X | Y | $Z_n$ | L | M | $R^2$ |
|---|---|---|---|---|---|---|---|
| —(CH$_2$)$_2$—CH(OCH$_3$)—(CH$_2$)$_2$— | | —CH$_3$ | —CH$_3$ | 6-CH$_3$ | O | O | —CH$_2$—C$_6$H$_5$ |
| —CH$_3$ | —CH$_3$ | —CH$_3$ | —CH$_3$ | 6-CH$_3$ | O | O | —CH$_2$—CH(C$_4$H$_9$)(C$_2$H$_5$) |
| —C$_2$H$_5$ | —CH$_3$ | —CH$_3$ | —CH$_3$ | 6-CH$_3$ | O | O | —CH$_2$—CH(C$_4$H$_9$)(C$_2$H$_5$) |
| —CH(CH$_3$)$_2$ | —CH$_3$ | —CH$_3$ | —CH$_3$ | 6-CH$_3$ | O | O | —CH$_2$—CH(C$_4$H$_9$)(C$_2$H$_5$) |
| —CF$_3$ | —CH$_3$ | —CH$_3$ | —CH$_3$ | 6-CH$_3$ | O | O | —CH$_2$—CH(C$_4$H$_9$)(C$_2$H$_5$) |
| —(CH$_2$)$_4$— | | —CH$_3$ | —CH$_3$ | 6-CH$_3$ | O | O | —CH$_2$—CH(C$_4$H$_9$)(C$_2$H$_5$) |
| —(CH$_2$)$_5$— | | —CH$_3$ | —CH$_3$ | 6-CH$_3$ | O | O | —CH$_2$—CH(C$_4$H$_9$)(C$_2$H$_5$) |
| —(CH$_2$)$_6$— | | —CH$_3$ | —CH$_3$ | 6-CH$_3$ | O | O | —CH$_2$—CH(C$_4$H$_9$)(C$_2$H$_5$) |
| —CH$_2$—CH(CH$_3$)—(CH$_2$)$_3$— | | —CH$_3$ | —CH$_3$ | 6-CH$_3$ | O | O | —CH$_2$—CH(C$_4$H$_9$)(C$_2$H$_5$) |
| —(CH$_2$)$_2$—CH(CH$_3$)—(CH$_2$)$_2$— | | —CH$_3$ | —CH$_3$ | 6-CH$_3$ | O | O | —CH$_2$—CH(C$_4$H$_9$)(C$_2$H$_5$) |
| —(CH$_2$)$_2$—CH(C$_2$H$_5$)—(CH$_2$)$_2$— | | —CH$_3$ | —CH$_3$ | 6-CH$_3$ | O | O | —CH$_2$—CH(C$_4$H$_9$)(C$_2$H$_5$) |
| —(CH$_2$)$_2$—CH(OCH$_3$)—(CH$_2$)$_2$— | | —CH$_3$ | —CH$_3$ | 6-CH$_3$ | O | O | —CH$_2$—CH(C$_4$H$_9$)(C$_2$H$_5$) |

TABLE 5-continued

| A | B | X | Y | $Z_n$ | L | M | $R^2$ |
|---|---|---|---|---|---|---|---|
| —CH₃ | —CH₃ | —CH₃ | —CH₃ | 6-CH₃ | O | O | phenyl |
| —C₂H₅ | —CH₃ | —CH₃ | —CH₃ | 6-CH₃ | O | O | phenyl |
| —CH(CH₃)₂ | —CH₃ | —CH₃ | —CH₃ | 6-CH₃ | O | O | phenyl |
| —CF₃ | —CH₃ | —CH₃ | —CH₃ | 6-CH₃ | O | O | phenyl |
| —(CH₂)₄— | | —CH₃ | —CH₃ | 6-CH₃ | O | O | phenyl |
| —(CH₂)₅— | | —CH₃ | —CH₃ | 6-CH₃ | O | O | phenyl |
| —(CH₂)₆— | | —CH₃ | —CH₃ | 6-CH₃ | O | O | phenyl |
| —CH₂—CH(CH₃)—(CH₂)₃— | | —CH₃ | —CH₃ | 6-CH₃ | O | O | phenyl |
| —(CH₂)₂—CH(CH₃)—(CH₂)₂— | | —CH₃ | —CH₃ | 6-CH₃ | O | O | phenyl |
| —(CH₂)₂—CH(C₂H₅)—(CH₂)₂— | | —CH₃ | —CH₃ | 6-CH₃ | O | O | phenyl |
| —(CH₂)₂—CH(OCH₃)—(CH₂)₂— | | —CH₃ | —CH₃ | 6-CH₃ | O | O | phenyl |
| —CH₃ | —CH₃ | —CH₃ | —CH₃ | 6-CH₃ | O | S | —C₂H₅ |
| —C₂H₅ | —CH₃ | —CH₃ | —CH₃ | 6-CH₃ | O | S | —C₂H₅ |
| —CH(CH₃)₂ | —CH₃ | —CH₃ | —CH₃ | 6-CH₃ | O | S | —C₂H₅ |
| —CF₃ | —CH₃ | —CH₃ | —CH₃ | 6-CH₃ | O | S | —C₂H₅ |
| —(CH₂)₄— | | —CH₃ | —CH₃ | 6-CH₃ | O | S | —C₂H₅ |

TABLE 5-continued

| A | B | X | Y | $Z_n$ | L | M | $R^2$ |
|---|---|---|---|---|---|---|---|
| —(CH$_2$)$_5$— | | —CH$_3$ | —CH$_3$ | 6-CH$_3$ | O | S | —C$_2$H$_5$ |
| —(CH$_2$)$_6$— | | —CH$_3$ | —CH$_3$ | 6-CH$_3$ | O | S | —C$_2$H$_5$ |
| —CH$_2$—CH(CH$_3$)—(CH$_2$)$_3$— | | —CH$_3$ | —CH$_3$ | 6-CH$_3$ | O | S | —C$_2$H$_5$ |
| —(CH$_2$)$_2$—CH(CH$_3$)—(CH$_2$)$_2$— | | —CH$_3$ | —CH$_3$ | 6-CH$_3$ | O | S | —C$_2$H$_5$ |
| —(CH$_2$)$_2$—CH(C$_2$H$_5$)—(CH$_2$)$_2$— | | —CH$_3$ | —CH$_3$ | 6-CH$_3$ | O | S | —C$_2$H$_5$ |
| —(CH$_2$)$_2$—CH(OCH$_3$)—(CH$_2$)$_2$— | | —CH$_3$ | —CH$_3$ | 6-CH$_3$ | O | S | —C$_2$H$_5$ |
| —CH$_3$ | —CH$_3$ | —CH$_3$ | —CH$_3$ | 6-CH$_3$ | O | S | —CH(CH$_3$)$_2$ |
| —C$_2$H$_5$ | —CH$_3$ | —CH$_3$ | —CH$_3$ | 6-CH$_3$ | O | S | —CH(CH$_3$)$_2$ |
| —CH(CH$_3$)$_2$ | —CH$_3$ | —CH$_3$ | —CH$_3$ | 6-CH$_3$ | O | S | —CH(CH$_3$)$_2$ |
| —CF$_3$ | —CH$_3$ | —CH$_3$ | —CH$_3$ | 6-CH$_3$ | O | S | —CH(CH$_3$)$_2$ |
| —(CH$_2$)$_4$— | | —CH$_3$ | —CH$_3$ | 6-CH$_3$ | O | S | —CH(CH$_3$)$_2$ |
| —(CH$_2$)$_5$— | | —CH$_3$ | —CH$_3$ | 6-CH$_3$ | O | S | —CH(CH$_3$)$_2$ |
| —(CH$_2$)$_6$— | | —CH$_3$ | —CH$_3$ | 6-CH$_3$ | O | S | —CH(CH$_3$)$_2$ |
| —CH$_2$—CH(CH$_3$)—(CH$_2$)$_3$— | | —CH$_3$ | —CH$_3$ | 6-CH$_3$ | O | S | —CH(CH$_3$)$_2$ |
| —(CH$_2$)$_2$—CH(CH$_3$)—(CH$_2$)$_2$— | | —CH$_3$ | —CH$_3$ | 6-CH$_3$ | O | S | —CH(CH$_3$)$_2$ |
| —(CH$_2$)$_2$—CH(C$_2$H$_5$)—(CH$_2$)$_2$— | | —CH$_3$ | —CH$_3$ | 6-CH$_3$ | O | S | —CH(CH$_3$)$_2$ |
| —(CH$_2$)$_2$—CH(OCH$_3$)—(CH$_2$)$_2$— | | —CH$_3$ | —CH$_3$ | 6-CH$_3$ | O | S | —CH(CH$_3$)$_2$ |
| —CH$_3$ | —CH$_3$ | —CH$_3$ | —CH$_3$ | 6-CH$_3$ | O | S | —CH$_2$—CH(CH$_3$)$_2$ |
| —C$_2$H$_5$ | —CH$_3$ | —CH$_3$ | —CH$_3$ | 6-CH$_3$ | O | S | —CH$_2$—CH(CH$_3$)$_2$ |
| —CH(CH$_3$)$_2$ | —CH$_3$ | —CH$_3$ | —CH$_3$ | 6-CH$_3$ | O | S | —CH$_2$—CH(CH$_3$)$_2$ |
| —CF$_3$ | —CH$_3$ | —CH$_3$ | —CH$_3$ | 6-CH$_3$ | O | S | —CH$_2$—CH(CH$_3$)$_2$ |
| —(CH$_2$)$_4$— | | —CH$_3$ | —CH$_3$ | 6-CH$_3$ | O | S | —CH$_2$—CH(CH$_3$)$_2$ |
| —(CH$_2$)$_5$— | | —CH$_3$ | —CH$_3$ | 6-CH$_3$ | O | S | —CH$_2$—CH(CH$_3$)$_2$ |
| —(CH$_2$)$_6$— | | —CH$_3$ | —CH$_3$ | 6-CH$_3$ | O | S | —CH$_2$—CH(CH$_3$)$_2$ |
| —CH$_2$—CH(CH$_3$)—(CH$_2$)$_3$— | | —CH$_3$ | —CH$_3$ | 6-CH$_3$ | O | S | —CH$_2$—CH(CH$_3$)$_2$ |
| —(CH$_2$)$_2$—CH(CH$_3$)—(CH$_2$)$_2$— | | —CH$_3$ | —CH$_3$ | 6-CH$_3$ | O | S | —CH$_2$—CH(CH$_3$)$_2$ |
| —(CH$_2$)$_2$—CH(C$_2$H$_5$)—(CH$_2$)$_2$— | | —CH$_3$ | —CH$_3$ | 6-CH$_3$ | O | S | —CH$_2$—CH(CH$_3$)$_2$ |
| —(CH$_2$)$_2$—CH(OCH$_3$)—(CH$_2$)$_2$— | | —CH$_3$ | —CH$_3$ | 6-CH$_3$ | O | S | —CH$_2$—CH(CH$_3$)$_2$ |
| —CH$_3$ | —CH$_3$ | —CH$_3$ | —CH$_3$ | 6-CH$_3$ | O | S | —CH$_2$—C(CH$_3$)$_3$ |
| —C$_2$H$_5$ | —CH$_3$ | —CH$_3$ | —CH$_3$ | 6-CH$_3$ | O | S | —CH$_2$—C(CH$_3$)$_3$ |
| —CH(CH$_3$)$_2$ | —CH$_3$ | —CH$_3$ | —CH$_3$ | 6-CH$_3$ | O | S | —CH$_2$—C(CH$_3$)$_3$ |
| —CF$_3$ | —CH$_3$ | —CH$_3$ | —CH$_3$ | 6-CH$_3$ | O | S | —CH$_2$—C(CH$_3$)$_3$ |
| —(CH$_2$)$_4$— | | —CH$_3$ | —CH$_3$ | 6-CH$_3$ | O | S | —CH$_2$—C(CH$_3$)$_3$ |
| —(CH$_2$)$_5$— | | —CH$_3$ | —CH$_3$ | 6-CH$_3$ | O | S | —CH$_2$—C(CH$_3$)$_3$ |
| —(CH$_2$)$_6$— | | —CH$_3$ | —CH$_3$ | 6-CH$_3$ | O | S | —CH$_2$—C(CH$_3$)$_3$ |
| —CH$_2$—CH(CH$_3$)—(CH$_2$)$_3$— | | —CH$_3$ | —CH$_3$ | 6-CH$_3$ | O | S | —CH$_2$—C(CH$_3$)$_3$ |
| —(CH$_2$)$_2$—CH(CH$_3$)—(CH$_2$)$_2$— | | —CH$_3$ | —CH$_3$ | 6-CH$_3$ | O | S | —CH$_2$—C(CH$_3$)$_3$ |
| —(CH$_2$)$_2$—CH(C$_2$H$_5$)—(CH$_2$)$_2$— | | —CH$_3$ | —CH$_3$ | 6-CH$_3$ | O | S | —CH$_2$—C(CH$_3$)$_3$ |
| —(CH$_2$)$_2$—CH(OCH$_3$)—(CH$_2$)$_2$— | | —CH$_3$ | —CH$_3$ | 6-CH$_3$ | O | S | —CH$_2$—C(CH$_3$)$_3$ |

Table 6

Table 6 contains the compounds of the formula (Ic) in which A, B, L, M and $R^2$ have the meanings mentioned in Table 5 and X and Y in each case represent chlorine and $Z_n$ represents hydrogen.

Table 7

Table 7 contains the compounds of the formula (Ic) in which A, B, L, M and $R^2$ have the meanings mentioned in Table 5 and X and Y in each case represent $CH_3$ and $Z_n$ represents hydrogen.

In addition to the compounds mentioned in the preparation examples, the following 3-aryl-4-hydroxy-$\Delta^3$-dihydrothiophen-2-one derivatives of the formula (Id) may be mentioned individually:

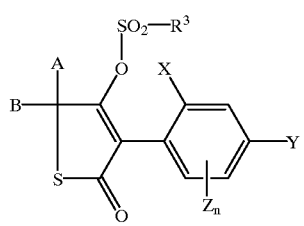

(Id)

TABLE 8

| A | B | X | Y | $Z_n$ | $R^3$ |
|---|---|---|---|---|---|
| —(CH$_2$)$_5$— | CH$_3$ | CH$_3$ | 6-CH$_3$ | 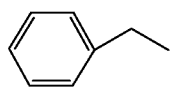 |
| —(CH$_2$)$_5$— | CH$_3$ | CH$_3$ | 6-CH$_3$ |  |

TABLE 8-continued

| A | B | X | Y | $Z_n$ | $R^3$ |
|---|---|---|---|---|---|
| —(CH$_2$)$_5$— | CH$_3$ | CH$_3$ | 6-CH$_3$ | | |
| —(CH$_2$)$_5$— | CH$_3$ | CH$_3$ | 6-CH$_3$ | | |
| —(CH$_2$)$_5$— | CH$_3$ | CH$_3$ | 6-CH$_3$ | CH$_3$ | |

In addition to the compounds mentioned in the preparation examples, the following 3-aryl-4-hydroxy-$\Delta^3$-dihydrothiophen-2one derivatives of the formula (Ie) may be mentioned individually:

(Ie)

TABLE 9

| A | B | X | Y | $Z_n$ | L | $R^4$ | $R^5$ |
|---|---|---|---|---|---|---|---|
| —(CH$_2$)$_5$ | CH$_3$ | CH$_3$ | 6-CH$_3$ | S | CF$_3$CH$_2$O— | CH$_3$ |
| —(CH$_2$)$_5$ | CH$_3$ | CH$_3$ | 6-CH$_3$ | O | CH$_3$—O— | C$_2$H$_5$—S— |
| —(CH$_2$)$_5$ | CH$_3$ | CH$_3$ | 6-CH$_3$ | O | CH$_3$—O— | (CH$_3$)$_2$CH—S— |
| —(CH$_2$)$_5$ | CH$_3$ | CH$_3$ | 6-CH$_3$ | O | CH$_3$—O— | C$_2$H$_5$\\CH—S—/CH$_3$ |
| | | | | | | | — |
| —(CH$_2$)$_5$ | CH$_3$ | CH$_3$ | 6-CH$_3$ | O | C$_2$H$_5$O— | C$_2$H$_5$—S— |
| —(CH$_2$)$_5$ | CH$_3$ | CH$_3$ | 6-CH$_3$ | O | C$_2$H$_5$O— | (CH$_3$)$_2$CH—S— |
| —(CH$_2$)$_5$ | CH$_3$ | CH$_3$ | 6-CH$_3$ | O | C$_2$H$_5$O | C$_2$H$_5$\\CH—S—/CH$_3$ |

In addition to the compounds mentioned in the preparation examples, the following 3-aryl-4-hydroxy-Δ³-dihydrothiophen-2-one derivatives of the formula (If) may be mentioned individually (Table 10):

In addition to the compounds mentioned in the preparation examples, the following 3-aryl-4-hydroxy-Δ³-dihydrothiophen-2-one derivatives of the formula (Ig) may be mentioned individually (Table 11):

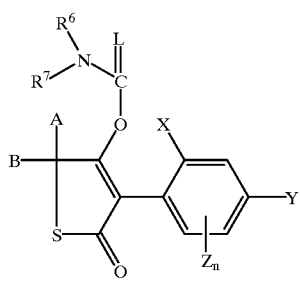
(If)

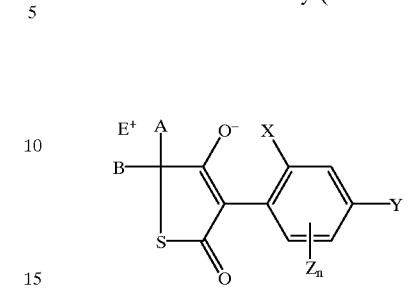
(Ig)

TABLE 10

| A | B | X | Y | $Z_n$ | L | $R^6$ | $R^7$ |
|---|---|---|---|---|---|---|---|
| —(CH$_2$)$_5$— | CH$_3$ | CH$_3$ | 6-CH$_3$ | | O | CH$_3$— | CH$_3$— |
| —(CH$_2$)$_5$— | CH$_3$ | CH$_3$ | 6-CH$_3$ | | S | CH$_3$— | CH$_3$— |
| —(CH$_2$)$_5$— | CH$_3$ | CH$_3$ | 6-CH$_3$ | | O | CH$_2$—CHCH$_2$— | CH$_2$=CH—CH$_2$— |
| —(CH$_2$)$_5$— | CH$_3$ | CH$_3$ | 6-CH$_3$ | | O | —(CH$_2$)$_2$—O—(CH$_2$)$_2$— | |
| —(CH$_2$)$_5$— | CH$_3$ | CH$_3$ | 6-CH$_3$ | | S | | —(CH$_2$)$_5$— |
| —(CH$_2$)$_5$— | CH$_3$ | CH$_3$ | 6-CH$_3$ | | S |  | C$_2$H$_5$— |

TABLE 11

| A | B | X | Y | $Z_n$ | E |
|---|---|---|---|---|---|
| —CH$_3$ | CH$_3$ | —CH$_3$ | —CH$_3$ | 6-CH$_3$ | NH$_4$ |
| —CH$_3$ | —CH$_3$ | —CH$_3$ | —CH$_3$ | 6-CH$_3$ | Na |
| —C$_2$H$_5$ | —CH$_3$ | —CH$_3$ | —CH$_3$ | 6-CH$_3$ | Na |
| —CH(CH$_3$)$_2$ | —CH$_3$ | —CH$_3$ | —CH$_3$ | 6-CH$_3$ | Na |
| —CF$_3$ | —CH$_3$ | —CH$_3$ | —CH$_3$ | 6-CH$_3$ | Na |
| —(CH$_2$)$_4$— | | —CH$_3$ | —CH$_3$ | 6-CH$_3$ | Na |
| —(CH$_2$)$_5$— | | —CH$_3$ | —CH$_3$ | 6-CH$_3$ | Na |
| —(CH$_2$)$_6$— | | —CH$_3$ | —CH$_3$ | 6-CH$_3$ | Na |
| —CH$_2$—CH(CH$_3$)—(CH$_2$)$_3$— | | —CH$_3$ | —CH$_3$ | 6-CH$_3$ | Na |
| —(CH$_2$)$_2$—CH(CH$_3$)—(CH$_2$)$_2$— | | —CH$_3$ | —CH$_3$ | 6-CH$_3$ | Na |
| —(CH$_2$)$_2$—CH(C$_2$H$_5$)—(CH$_2$)$_2$— | | —CH$_3$ | —CH$_3$ | 6-CH$_3$ | Na |
| —(CH$_2$)$_2$—CH(OCH$_3$)—(CH$_2$)$_2$— | | —CH$_3$ | —CH$_3$ | 6-CH$_3$ | Na |
| —CH$_3$ | —CH$_3$ | —CH$_3$ | —CH$_3$ | 6-CH$_3$ | i-C$_3$H$_7$NH$_3$ |
| —C$_2$H$_5$ | —CH$_3$ | —CH$_3$ | —CH$_3$ | 6-CH$_3$ | i-C$_3$H$_7$NH$_3$ |
| —CH(CH$_3$)$_2$ | —CH$_3$ | —CH$_3$ | —CH$_3$ | 6-CH$_3$ | i-C$_3$H$_7$NH$_3$ |

TABLE 11-continued

| A | B | X | Y | $Z_n$ | E |
|---|---|---|---|---|---|
| —CF$_3$ | —CH$_3$ | —CH$_3$ | —CH$_3$ | 6-CH$_3$ | i-C$_3$H$_7$NH$_3$ |
| | —(CH$_2$)$_4$— | —CH$_3$ | —CH$_3$ | 6-CH$_3$ | i-C$_3$H$_7$NH$_3$ |
| | —(CH$_2$)$_5$— | —CH$_3$ | —CH$_3$ | 6-CH$_3$ | i-C$_3$H$_7$NH$_3$ |
| | —(CH$_2$)$_6$— | —CH$_3$ | —CH$_3$ | 6-CH$_3$ | i-C$_3$H$_7$NH$_3$ |
| | —CH$_2$—CH(CH$_3$)—(CH$_2$)$_3$— | —CH$_3$ | —CH$_3$ | 6-CH$_3$ | i-C$_3$H$_7$NH$_3$ |
| | —(CH$_2$)$_2$—CH(CH$_3$)—(CH$_2$)$_2$— | —CH$_3$ | —CH$_3$ | 6-CH$_3$ | i-C$_3$H$_7$NH$_3$ |
| | —(CH$_2$)$_2$—CH(C$_2$H$_5$)—(CH$_2$)$_2$— | —CH$_3$ | —CH$_3$ | 6-CH$_3$ | i-C$_3$H$_7$NH$_3$ |
| | —(CH$_2$)$_2$—CH(OCH$_3$)—(CH$_2$)$_2$— | —CH$_3$ | —CH$_3$ | 6-CH$_3$ | i-C$_3$H$_7$NH$_3$ |

Table 12

Table 12 contains the compounds of the formula (Ig) in which A, B and E have the meanings mentioned in Table 11 and X and Y in each case represent chlorine and $Z_n$ represents hydrogen.

Table 13

Table 13 contains the compounds of the formula (Ig) in which A, B and E have the meanings mentioned in Table 11 and X and Y in each case represent CH$_3$ and $Z_n$ represents hydrogen.

If ethyl 2-(2,6-dichlorophenyl)-4-(4-methoxy) benzylmercapto-4-methyl-3-oxo-valerate is used in accordance with process (A), the course of the process according to the invention can then be represented by the following reaction scheme:

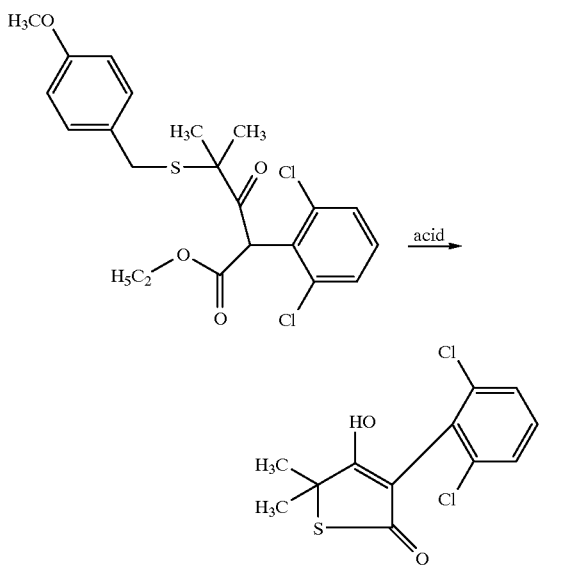

If 3-(2,4,6-trimethylphenyl)-4-hydroxy-5,5-dimethyl-$\Delta^3$-dihydrothiophen-2-one and pivaloyl chloride are used as starting compounds in accordance with process (B) (variant α), the course of the process according to the invention can then be represented by the following reaction scheme:

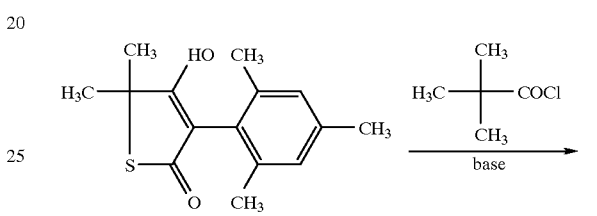

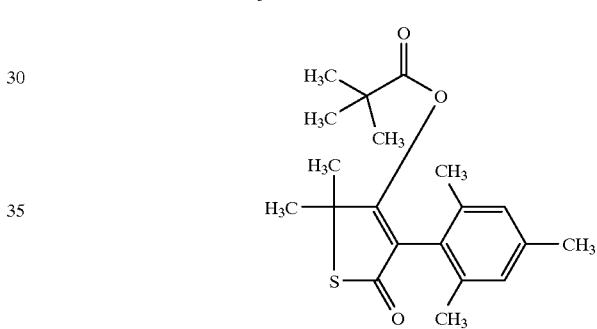

If 3-(2,4,5-trimethylphenyl)-4-hydroxy-5-methyl-5-phenyl-$\Delta^3$-dihydrothiophen-2-one and acetic anhydride are used as starting compounds in accordance with process B (variant β), the course of the process according to the invention can then be represented by the following reaction scheme:

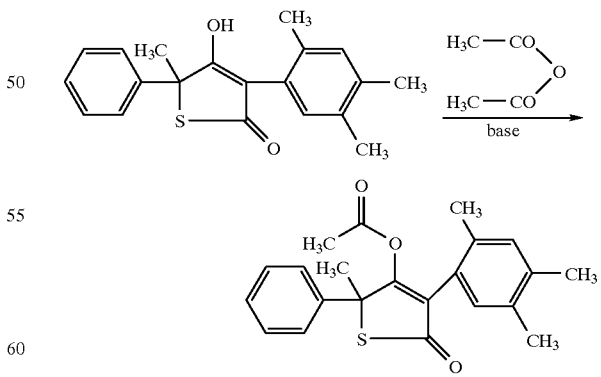

If 3-(2,4-dichlorophenyl)-4-hydroxy-5-isopropyl-5-methyl-$\Delta^3$-dihydrothiophen-2-one and ethoxyethyl chloroformate are used as starting compounds in accordance with process C, the course of the process according to the invention can then be represented by the following reaction scheme:

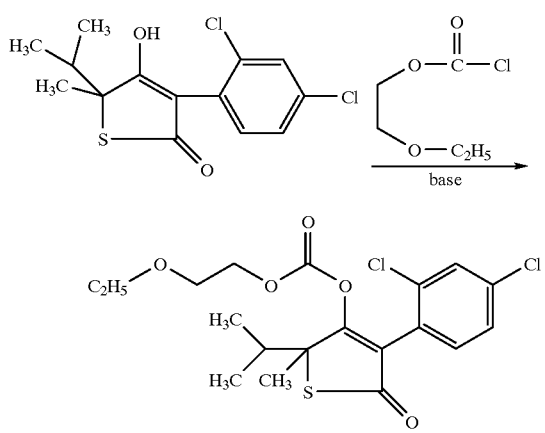

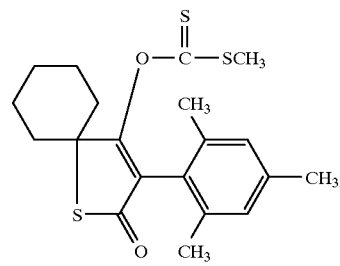

If 3-(2,4,6trimethylphenyl)-4-hydroxy-5-(3-methoxy)-pentamethylene-Δ³-dihydro-thiophen-2-one and methanesulfonyl chloride are used as starting compounds in accordance with process (E), the course of the reaction can then be represented by the following reaction scheme:

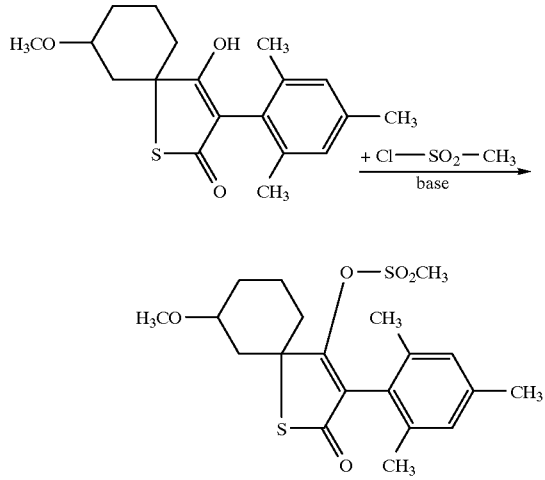

If 3-(2,4,6-trimethylphenyl)-4-hydroxy-5-ethyl-5-methyl-Δ³-dihydro-thiophen-2-one and methyl chloromonothioformate are used as starting compounds in accordance with process (D$_\alpha$), the course of the reaction can then be represented as follows:

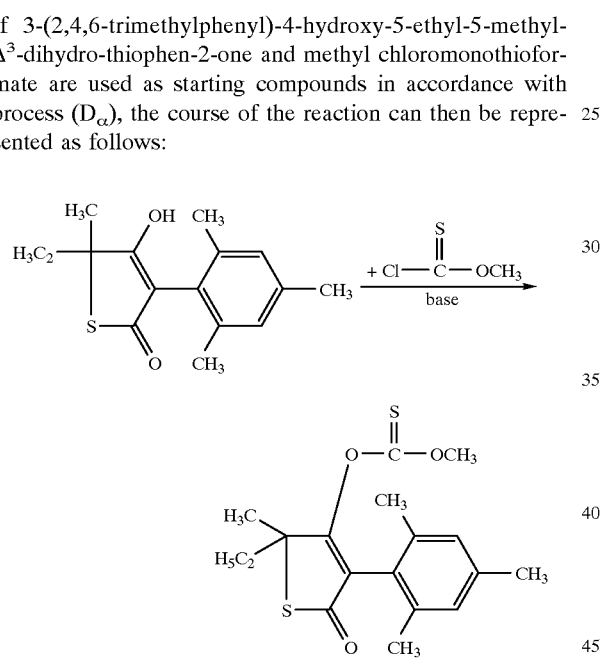

If 3-(2,4,6trimethylphenyl)-4-hydroxy-5,5-dimethyl-Δ³-dihydro-thiophen-2-one and methanethio-phosphonyl chloride 2,2,2-trifluoroethyl ester are used as starting compounds in accordance with process (F), the course of the reaction can then be represented by the following reaction scheme:

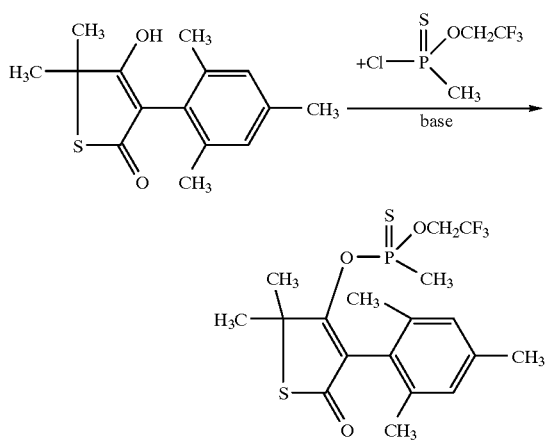

If 3-(2,4,6-trimethylphenyl-4-hydroxy-5,5-pentamethylene-Δ³-dihydrothiophen-2-one, carbon disulfide and methyl iodide are used as starting components in accordance with process (D$_\alpha$), the course of the reaction can then be represented as follows:

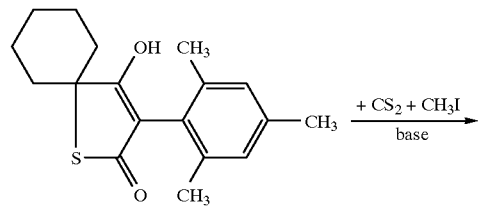

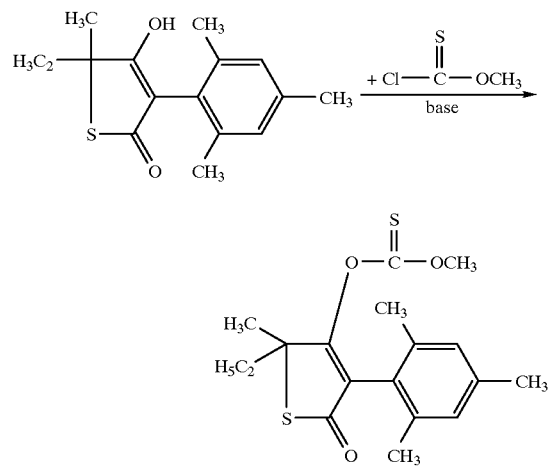

If 3-(2,4,6trimethylphenyl)-4-hydroxy-5-tetramethylene-Δ³-dihydro-thiophen-2-one and ethyl isocyanate are used as starting compounds in accordance with process (G$_\alpha$), the course of the reaction can then be represented by the following reaction scheme:

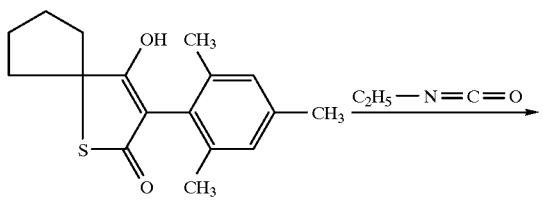

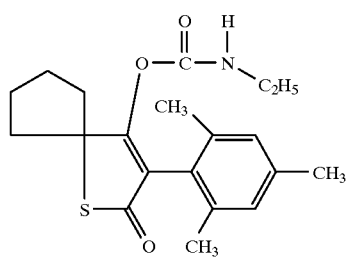

If 3-(2,4,6-trimethylphenyl)-4-hydroxy-5-trifluoromethyl-5-methyl-Δ$^3$-dihydro-thiophen-2-one and dimethylcarbamoyl chloride are used as starting compounds in accordance with process (G$_\beta$), the course of the reaction can then be represented by the following scheme:

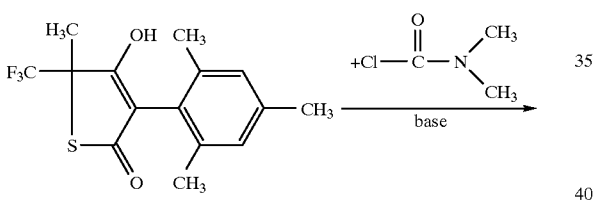

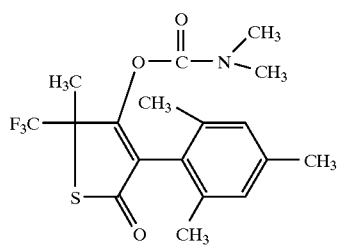

If 3-(2,4,6trimethylphenyl)-4-hydroxy-5,5-dimethyl-Δ$^3$-dihydro-thiophen-2-one and NaOH are used as components in accordance with process (H), the course of the process according to the invention can then be represented by the following reaction scheme:

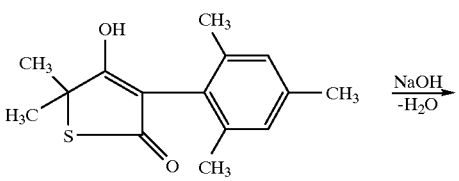

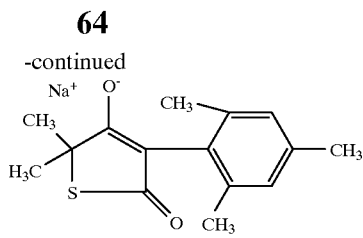

The compounds of the formula (II)

(II)

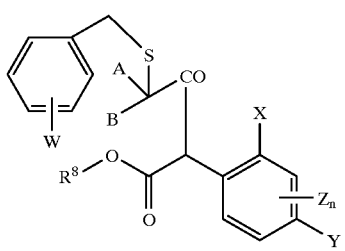

which are required as starting compounds in the above process (A) and in which

A, B, W, X, Y, Z, n and R$^8$ have the abovementioned meaning, are novel. They can be prepared by methods which are known in principle. For example, 2-aryl4S-benzyl-β-ketocarboxylic esters of the formula (II) are obtained if arylacetic esters of the formula (XIV)

(XIV)

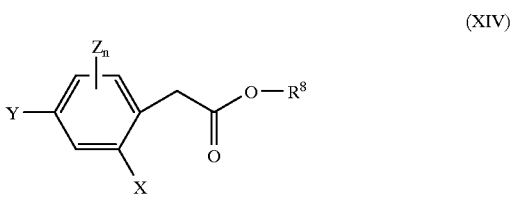

in which

X, Y, Z, R$^8$ and n have the abovementioned meaning,
are acylated with 2-benzylthio-carbonyl halides of the formula (XV)

(XV)

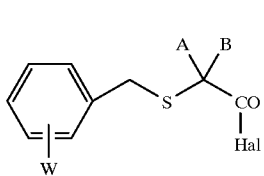

in which

A, B and W have the abovementioned meaning, and

Hal represents halogen, in particular chlorine or bromine, in the presence of strong bases (see, for example, M. S. Chambers, E. J. Thomas, D. J. Williams, J. Chem. Soc. Chem. Commun., (1987), 1228).

The compounds of the formula (XIV) are known from the literature and are readily available compounds, some of which can be obtained commercially.

The benzylthio-carbonyl halides of the formula (XV) are either known and/or can be prepared by known methods.

The benzylthio-carbonyl halides of the formula (XVa)

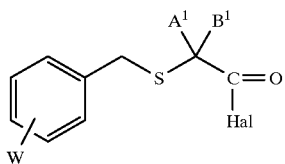
(XVa)

in which
W has the abovementioned meaning
Hal represents halogen, in particular chlorine or bromine, and
$A^1$ and $B^1$, together with the carbon atom to which they are bonded, form a saturated or unsaturated ring which is optionally interrupted by at least one hetero atom and which is optionally substituted, or in which
$A^1$ and $B^1$, together with the carbon atom to which they are bonded, represent a ring in which the substituents, together with the carbon atoms to which they are bonded, represent a saturated or unsaturated ring which is optionally substituted identically or differently once or more than once by alkyl, alkoxy or halogen and which can be interrupted by oxygen or sulfur, are novel.

The compounds of the formula (XVa) are obtained if benzylthiocarboxylic acids of the formula (XVIa)

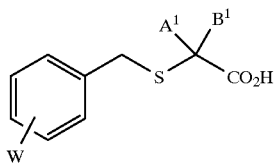
(XVIa)

in which
$A^1$, $B^1$ and W have the abovementioned meanings,
are reacted with halogenating agents, such as, for example, phosgene, phosphorus trichloride, phosphorus pentachloride, phosphorus tribromide, phosphorus pentabromide or thionyl chloride, optionally in the presence of an inert diluent, such as, for example, hydrocarbons or halogenated hydrocarbons, at temperatures of between −30° C. and 150° C., preferably of between −20° C. and 100° C. (see, for example, J. Antibiotics (1983), 26, 1589).

Some of the benzylthiocarboxylic acids of the formula (XVI)

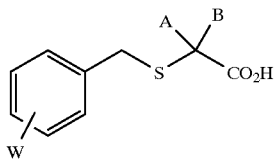
(XVI)

in which
A, B and W have the abovementioned meanings, are known.

The benzylthiocarboxylic acids of the formula (XVI) are obtained, for example, if carboxylic esters of the formula (XVII)

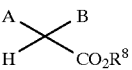
(XVII)

in which
A, B and $R^8$ have the abovementioned meanings,
are reacted with disulfides of the formula (XVIII)

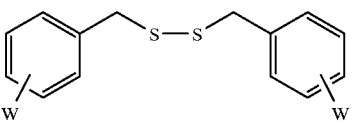
(XVIII)

in which
W has the abovementioned meaning,
optionally in the presence of a diluent such as, for example, tetrahydrofuran and/or n-hexane, and in the presence of bases such as, for example, sodium hydride, lithium diisopropylamide or potassium tert-butoxide.

In this case, the general approach is that the corresponding anion is first formed from the ester of the formula (XVII) by reaction with the base in a suitable diluent, optionally at temperatures of down to −80° C. The disulfide of the formula (XVIII) is then added and the mixture is allowed to react at temperatures of from −20° C. to 50° C. (see, for example, J. Med. Chem. (1988), 31, 2199).

The compounds of the formulae (XVII) and (XVIII) are generally known organochemical compounds.

Process (A) is characterized in that compounds of the formula (II), in which A, B, W, X, Y, Z, n and $R^8$ have the abovementioned meaning, are subjected to an intramolecular cyclization in the presence of acids.

All inert organic solvents may be employed as diluents in process (A) according to the invention. Those which are preferably used are hydrocarbons, such as toluene and xylene, and, in addition, halogenated hydrocarbons, such as dichloromethane, chloroform, ethylene chloride, chlorobenzene and dichlorobenzene, and also polar solvents, such as dimethyl sulfphoxide, sulfolane, dimethylformamide and N-methylpyrrolidone. In addition to this, alcohols, such as methanol, ethanol, propanol, iso-propanol, butanol, isobutanol and tert-butanol, can also be employed.

Where appropriate, the acid which is employed can also serve as diluent.

All customary inorganic and organic acids, such as, for example, hydrohalic acids, sulfuric acid, alkylsulfonic, arylsulfonic and haloalkylsulfonic acids, in particular halogenated alkylcarboxylic acids, such as, for example, trifluoroacetic acid, may be employed as acids in process (A) according to the invention.

In implementing process (A) according to the invention, the reaction temperatures can be varied within a relatively wide range. In general, the process is carried out at temperatures between 0° C. and 250° C., preferably between 50° C. and 150° C.

Process (A) according to the invention is generally carried out under standard pressure.

When carrying out process (A) according to the invention, the reaction components of the formula (II) and the acid are employed, for example, in equimolar quantities. However, it is also possible, where appropriate, to use the acid as solvent or as catalyst.

The process (Bα) is characterized in that compounds of the formula (Ia) are reacted with carbonyl halides of the formula (III).

All solvents which are inert towards these compounds may be employed as diluents in process (Bα) according to the invention. Those which are preferably used are hydrocarbons, such as benzine, benzene, toluene, xylene and tetralin, and, in addition, halogeno hydrocarbons, such as methylene chloride, chloroform, carbon tetrachloride, chlorobenzene and o-dichlorobenzene, and also ketones, such as acetone and methyl isopropyl ketone, also ethers, such as diethyl ether, tetrahydrofuran and dioxane, and, furthermore, carboxylic esters, such as ethyl acetate, and also strongly polar solvents, such as dimethyl sulfoxide and sulfolane. If the stability of the acid halide towards hydrolysis permits it, the reaction can also be carried out in the presence of water.

All customary acid acceptors are suitable for use in the reaction in accordance with process (Bα) according to the invention. Those which are preferably used are tertiary amines, such as triethylamine, pyridine, diazabicyclooctane (DABCO), diazabicycloundecene (DBU), diazabicyclononene (DBN), Hünig base and N,N-dimethyl-aniline, and, in addition, alkaline earth metal oxides, such as magnesium oxide and calcium oxide, and also alkali metal and alkaline earth metal carbonates, such as sodium carbonate, potassium carbonate and calcium carbonate.

The reaction temperatures can be varied within a relatively wide range in process (Bα) according to the invention. In general, temperatures of between −20° C. and +150° C., preferably of between 0° C. and 100° C., are employed.

When carrying out process (Bα) according to the invention, the starting compounds of the formula (Ia) and the carbonyl halide of the formula (III) are generally used in approximately equivalent quantities. However, it is also possible to employ the carbonyl halide in a relatively large excess (up to 5 mol). Working up is carried out in accordance with customary methods.

The process (Bβ) is characterized in that compounds of the formula (Ia) are reacted with carboxylic anhydrides of the formula (IV).

In process (Bβ) according to the invention, those diluents can preferably be used as diluents which also preferably come into consideration when acid halides are used. Otherwise, a carboxylic anhydride employed in excess can also simultaneously function as diluent.

The reaction temperatures can be varied within a relatively wide range in process (Bβ) according to the invention. In general, temperatures of between −20° C. and +150° C., preferably of between 0° C. and 100° C., are employed.

When carrying out process (Bβ) according to the invention, the starting compounds of the formula (Ia) and the carboxylic anhydride of the formula (IV) are generally used in approximately equivalent quantities. However, it is also possible to employ the carboxylic anhydride in a relatively large excess (up to 5 mol). The working up is carried out in accordance with customary methods.

In general, the procedure is to remove diluent and carboxylic anhydride which is present in excess, and also the resulting carboxylic acid, by distillation or by washing with an organic solvent or with water.

The process (C) is characterized in that compounds of the formula (Ia) are reacted with chloroformic esters or chloroformic thioesters of the formula (V).

All customary acid acceptors are suitable for use as acid binding agents in the reaction in accordance with process (C) according to the invention. Those which are preferably used are tertiary amines, such as triethylamine, pyridine, DABCO, DBC, DBA, Hünig base and N,N-dimethyl-aniline, and, in addition, alkaline earth metal oxides, such as magnesium oxide and calcium oxide, and also alkali metal and alkaline earth metal carbonates, such as sodium carbonate, potassium carbonate and calcium carbonate.

All solvents which are inert to the starting compounds may be employed as diluents in process (C) according to the invention. Those which are preferably used are hydrocarbons, such as benzine, benzene, toluene, xylene and tetralin, and, in addition, halogenohydrocarbons, such as methylene chloride, chloroform, carbon tetrachloride, chlorobenzene and o-dichlorobenzene, and also ketones, such as acetone and methyl isopropyl ketone, also ethers, such as diethyl ether, tetrahydrofuran and dioxane, and, in addition to this, carboxylic esters, such as ethyl acetate, and also strongly polar solvents, such as dimethyl sulfoxide and sulfolane.

The reaction temperatures can be varied within a relatively wide range when carrying out process (C) according to the invention. If the process is carried out in the presence of a diluent and of an acid binding agent, the reaction temperatures are then generally between −20° C. and +100° C., preferably between 0° C. and 50° C.

The process (C) according to the invention is generally carried out under standard pressure.

When carrying out process (C) according to the invention, the starting compounds of the formula (Ia) and the corresponding chloroformic ester or chloroformic thioester of the formula (V) are generally used in approximately equivalent quantities. However, it is also possible to employ the one or other component in a relatively large excess (up to 2 mol). Working up is then carried out in accordance with customary methods. In general, the procedure is to remove salts which have precipitated out and to concentrate the remaining reaction mixture by stripping off the diluent.

In preparation process (D$_\alpha$), approximately 1 mol of chloromonothioformic ester or chlorodithioformic ester of the formula (VII) is reacted, at from 0 to 120° C., preferably at from 20 to 60° C., per mol of starting compound of the formula (Ia).

All inert polar organic solvents, such as ethers, amides, alcohols, sulfones and sulfoxides, are suitable for use as diluents which are added where appropriate.

Dimethyl sulfoxide, tetrahydrofuran, dimethylformamide or dimethyl sulfide are preferably employed.

If, in a preferred embodiment, the enolate salt of the compound of the formula (Ia) is prepared by adding strong deprotonating agents such as, for example, sodium hydride or potassium tert-butoxide, there is no need for any further addition of acid binding agents.

If acid binding agents are employed, customary inorganic or organic bases are then suitable for use; sodium hydroxide, sodium carbonate, potassium carbonate, pyridine and triethylamine may be cited by way of example.

The reaction can be carried out under standard pressure or under elevated pressure, with standard pressure being preferred. Working up takes place in accordance with customary methods.

In preparation process (D$_\beta$), the equimolar quantity, or an excess, of carbon disulfide is added per mol of starting compound of the formula (II). In this case, temperatures of from 0 to 50° C. are preferably employed, especially of from 20 to 30° C.

It is often expedient initially to prepare the corresponding salt from the compound of formula (II) by adding a deprotonating agent (such as, for example, potassium tert-butoxide or sodium hydride). The compound (II) is reacted with carbon disulfide until formation of the intermediate compound is complete, e.g. after stirring at room temperature for several hours.

Subsequent reaction with the alkyl halide of the formula (VII) is preferably carried out at from 0 to 70° C., and especially at from 20 to 50° C. At least an equimolar quantity of alkyl halide is employed for this reaction.

The reaction is carried out under standard pressure or under elevated pressure, preferably under standard pressure.

Working up is once again carried out in accordance with customary methods.

In preparation process (E), approximately 1 mol of sulfonyl chloride (VIII) is reacted, at from 0 to 150° C., preferably at from 20 to 70° C., per mol of starting compound of the formula (Ia).

All inert polar organic solvents, such as ethers, amides, nitriles, alcohols, sulfones and sulfoxides, are suitable for use as diluents which are added where appropriate.

Dimethyl sulfoxide, tetrahydrofuran, dimethylformamide or dimethyl sulfide are preferably employed.

If, in a preferred embodiment, the enolate salt of the compound of the formula (Ia) is prepared by adding strong deprotonating agents (such as, for example, sodium hydride or potassium tert-butoxide), there is no need for any further addition of acid binding agents.

If acid binding agents are employed, customary inorganic or organic bases are then suitable for use; sodium hydroxide, sodium carbonate, potassium carbonate and pyridine may be cited by way of example.

The reaction can be carried out under standard pressure or under elevated pressure, with standard pressure being preferred. Working up takes place in accordance with customary methods.

Where appropriate, phase-transfer conditions can be employed in preparation process (E) (W. J. Spillane et al., J. Chem. Soc., Perkin Trans I, (3) 677–9 (1982)). In this case, from 0.3 to 1.5 mol of sulfonyl chloride (VIII), preferably 1.0 mol, are reacted, at from 0° to 150° C., preferably at from 20 to 70° C., per mol of starting compound of the formula (Ia).

All quaternary ammonium salts, preferably tetraoctylammonium bromide and benzyl triethylammonium chloride, may be used as phase-transfer catalysts. In this case, all nonpolar inert solvents may serve as organic solvents; benzene and toluene are preferably employed.

In preparation process (F), from 1 to 2, preferably from 1 to 1.3, mol of the phosphorus compound of the formula (IX) are reacted, at temperatures of between −40° C. and 150° C., preferably of between −10 and 110° C., per 1 mol of the compound of the formula (Ia) in order to obtain compounds of the structure (Ie).

All inert, polar organic solvents, such as ethers, amides, nitriles, alcohols, sulfides, sulfones, sulfoxides, etc., are suitable for use as diluents which are added where appropriate.

Acetonitrile, dimethyl sulfoxide, tetrahydrofuran, dimethylformamide or dimethyl sulfide are preferably employed.

Customary inorganic or organic bases, such as hydroxides or carbonates, are suitable for use as acid binding agents which are added where appropriate. Sodium hydroxide, sodium carbonate, potassium carbonate and pyridine may be cited by way of example.

The reaction can be carried out under standard pressure or under elevated pressure, with standard pressure being preferred. Working up takes place in accordance with customary organochemical methods. The resulting end products are preferably purified by crystallization, by chromatographic purification or by so-called "partial distillation", i.e. removal of the volatile constituents in vacuo.

In preparation process ($G_\alpha$), approximately 1 mol of isocyanate or isothiocyanate of formula (X) is reacted, at from 0 to 100° C., preferably at from 20 to 50° C., per mol of starting compound of the formula (Ia).

All inert organic solvents, such as ethers, amides, nitrites, sulfones or sulfoxides, are suitable for use as diluents which are added where appropriate.

If appropriate, catalysts may be added to accelerate the reaction. Organotin compounds, such as, for example, dibutyltin dilaurate, can very advantageously be employed as catalysts. The reaction is preferably carried out under standard pressure.

In preparation process ($G_\beta$), approximately 1 mol of carbamoyl chloride or thiocarbamoyl chloride of the formula (XI) is reacted, at from 0 to 150° C., preferably at from 20 to 70° C., per mol of starting compound of the formula (Ia).

All inert polar organic solvents, such as ethers, amides, alcohols, sulfones or sulfoxides, are suitable for use as diluents which are added where appropriate.

Dimethyl sulfoxide, tetrahydrofuran, dimethylformamide or dimethyl sulfide are preferably employed.

If, in a preferred embodiment, the enolate salt of the compound of the formula (Ia) is prepared by adding strong deprotonating agents (such as, for example, sodium hydride or potassium tert-butoxide), there is no need for any further addition of acid binding agents.

If acid binding agents are employed, customary inorganic or organic bases are then suitable for use; sodium hydroxide, sodium carbonate, potassium carbonate and pyridine may be cited by way of example.

The reaction can be carried out under standard pressure or under elevated pressure, with standard pressure being preferred. Working up takes place in accordance with customary methods.

Process (H) is characterized in that compounds of the formula (Ia) are reacted with metal compounds of the formula (XII) or amines of the formula (XIII).

In the process according to the invention, ethers, such as tetrahydrofuran, dioxane or diethyl ether, or else alcohols, such as methanol, ethanol or isopropanol, and water as well, can preferably be employed as diluents. Process (H) according to the invention is generally carried out under standard pressure. In general, the reaction temperatures are between −20° C. and 100° C., preferably between 0° C. and 50° C.

When carrying out process (H) according to the invention, the starting compounds of the formula (Ia) and (XII) or (XIII) are generally used in approximately equimolar quantities. However, it is also possible to employ the one or other component in a relatively large excess (up to 2 mol). In general, working up is achieved by concentrating the reaction mixture by stripping off the diluent.

The following compounds of the formula (II) may be mentioned by way of example:

Methyl 2-(2,4-dichlorophenyl)-4-(4-methoxybenzylmercapto)-4-methyl-3-oxo-valerate Methyl 2-(2,4-dichlorophenyl)-4-(4-methoxybenylmercapto)-4methyl-3-oxo-hexanecarboxylate Methyl 2-(2,4-dichlorophenyl)-4,5-(dimethyl)-4-methoxybenzylmercapto)-3-oxo-hexanecarboxylate Methyl 2-(2,4-dichlorophenyl)-4-(4-methoxybenzylmercapto)-3-oxo-4,4-tetramethylenebutyrate Methyl 2-(2,4-dichlorophenyl)-4-(4-methoxybenzylmercapto)-3-oxo-4,4-pentamethylenebutyrate Methyl 2-(2,4-dichlorophenyl)-4,4-hexamethylene-4-(4-methoxybenzylmercapto)-3-oxo-butyrate Methyl 2-(2,4-dichlorophenyl)-4,4-(2-methylpentamethylene)-4-(4-methoxybenzylmercapto)-3-oxo-butyrate Methyl 2-(2,4-dichlorophenyl)-4,4-(3-methylpentamethylene)-4-(4-methoxybenzylmercapto)-3-oxo-butyrate Methyl 2-(2,4-dichlorophenyl)-4,4-(3-ethylpentamethylene)-4-(4-methoxybenzylmercapto)-3-oxo-butyrate Methyl 2-(2,4-dichlorophenyl)-4,4-[3-(1-methyl)ethylpentamethylene]-4-(4-methoxybenzylmercapto)-3-oxo-butyrate Methyl 2-(2,4-dichlorophenyl)-4-(4-methoxybenzylmercapto)-4,4-(3-methoxypentamethylene)-3-oxo-butyrate Methyl 2-(2,4-dimethylphenyl)-4-(4-methoxybenzylmercapto)-4-methyl-3-oxo-valerate Methyl 2-(2,4-dimethylphenyl)-4-(4-methoxybenzylmercapto)-4-methyl-3-oxo-hexanecarboxylate Methyl 2-(2,4-dimethylphenyl-4,5-(dimethyl)-4-(4-methoxybenzylmercapto)-3-oxo-hexanecarboxylate Methyl 2-(2,4-dimethylphenyl)-4-(4-methoxybenzylmercapto)-3-oxo-4,4-tetramethylenebutyrate Methyl 2-(2,4-dimethylphenyl)-4-(4-methoxybenzylmercapto)-3-oxo-4,4-pentamethylenebutyrate Methyl 2-(2,4-dimethylphenyl)-4,4-hexamethylene-4-(4-methoxybenzylmercapto)-3-oxo-butyrate Methyl 2-(2,4dimethylphenyl)-4,4-(2-methylpentamethylene)-4-(4-methoxybenzylmercapto)-3-oxo-butyrate Methyl 2-2,4-dimethylphenyl)-4,4-(3-methylpentamethylene)-4-(4-methoxybenzylmercapto)-3-oxo-butyrate Methyl 2-(2,4-dimethylphenyl)-4,4-(3-ethylpentamethylene)-4-(4-methoxybenzylmercapto)-3-oxo-butyrate Methyl 2-(2,4-dimethylphenyl)-4,4-[3-(1-methyl)ethylpentamethylene]-4-(4-methoxybenzylmercapto)-3-oxo-butyrate Methyl 2-(2,4-dimethylphenyl)-4-(4-methoxybenzylmercapto)-4,4-(3-methoxypentamethylene)-3-oxo-butyrate Methyl 4-(4-methoxybenzylmercapto)-4methyl-3-oxo-2-(2,4,6-trimethylphenyl)-valerate Methyl 4-(4-methoxybenzylmercapto)-4-methyl-3-oxo-2-(2,4,6-trimethylphenyl)-hexanecarboxylate Methyl 4,5-(dimethyl)-4-(4-methoxybenzylmercapto)-3-oxo-2-(2,4,6-trimethylphenyl)-hexanecarboxylate Methyl 4-(4-methoxybenzylmercapto)-3-oxo-4,4-tetramethylene-2-(2,4,6-trimethylphenyl)-butyrate Methyl 4,4-hexamethylene-4-(4-methoxybenzylmercapto)-3-oxo-2-(2,4,6-trimethylphenyl)-butyrate Methyl 4-(4-methoxybenzylmercapto)-3-oxo-4,4-pentamethylene-2-(2,4,6-trimethylphenyl)-butyrate Methyl 4,4-(2-methylpentamethylene)-4-(4-methoxybenzylmercapto)-3-oxo-2-(2,4,6-trimethylphenyl)-butyrate Methyl 4,4-(3-methylpentamethylene)-4-(4-methoxybenzylmercapto)-3-oxo-2-(2,4,6-trimethylphenyl)-butyrate Methyl 4,4-(3-ethylpentamethylene)-4-(4-methoxybenzylmercapto)-3-oxo-2-(2,4,6-trimethylphenyl)-butyrate Methyl 4,4-[3-(1-methyl)ethylpentamethylene]-4-(4-methoxybenzylmercapto)-3-oxo-2-(2,4,6-trimethylphenyl)-butyrate Methyl 4-(4-methoxybenzylmercapto)-4,4-(3-methoxypentamethylene)-3-oxo-2-(2,4,6-trimethylphenyl)-butyrate The active compounds are suitable for controlling animal pests, preferably arthropods and nematodes, in particular insects and arachnida, which are encountered in agriculture, in forestry, in the protection of stored products and of materials, and in the hygiene field. They are active against normally sensitive and resistant species and against all or some stages of development. The abovementioned pests include:

From the order of the Isopoda, for example, *Oniscus asellus, Armadillium vulgare* and *Porcellio scaber.*

From the order of the Diplopoda, for example, *Blaniulus guttulatus.*

From the order of the Chilopoda, for example, *Geophilus carpophagus* and Scutigera spec..

From the order of the Symphyla, for example, *Scutigerella immaculata.*

From the order of the Thysanura, for example, *Lepisma saccharina.*

From the order of the Collembola, for example, *Onychiurus armatus.*

From the order of the Orthoptera, for example, *Blatta orientalis, Periplaneta americana, Leucophaea maderae, Blattella germanica, Acheta domesticus*, Gryllotalpa spp., *Locusta migratoria migratorioides, Melanoplus differentialis* and *Schistocerca gregaria.*

From the order of the Dermaptera, for example, *Forficula auricularia*

From the order of the Isoptera, for example, Reticulitermes spp..

From the order of the Anoplura, for example, *Phylloxera vastatrix*, Pemphigus spp., *Pediculus humanus corporis*, Haematopinus spp. and Linognathus spp..

From the order of the Mallophaga, for example, Trichodectus spp. and Damalinea spp..

From the order of the Thysanoptera, for example, *Hercinothrips femoralis* and *Thrips tabaci.*

From the order of the Heteroptera, for example, Eurygaster spp., *Dysdercus intermedius, Piesma quadrata, Cimex lectularius, Rhodnius prolixus* and Triatoma spp..

From the order of the Homoptera, for example, *Aleurodes brassicae, Bemisia tabaci, Trialeurodes vaporiariorum, Aphis gossypii, Brevicoryne brassicae, Cryptomyzus ribis, Aphis fabae, Doralis pomi, Eriosoma lanigerum, Hyalopterus arundinis, Macrosiphum avenae,* Myzus spp., *Phorodon humuli, Rhopalosiphum padi,* Empoasca spp., *Euscelis bilobatus, Nephotettix cincticeps, Lecanium corni, Saissetia oleae, Laodelphax striatellus, Nilaparvata lugens, Aonidiella aurantii, Aspidiotus hederae,* Pseudococcus spp. and Psylla spp..

From the order of the Lepidoptera, for example, *Pectinophora gossypiella, Bupalus piniarius, Cheimatobia brumata, Lithocolletis blancardella, Hyponomeuta padella, Plutella maculipennis, Malocosoma neustria, Euproctis chrysorrhoea,* Lymantria spp., *Bucculatrix thurberiella, Phyllocnistis citrella,* Agrotis spp., Euxoa spp., Feltia spp., *Earias insulana,* Heliothis spp., *Spodoptera exigua, Mamestra brassicae, Panolis flammea, Prodenia lituria,* Spodoptera spp., Trichoplusiani, *Capocapsa pomonella,* Pieris spp., Chilo spp., *Pyrausta nubilalis, Ephestia kuehniella, Galleria mellonella, Tineola bisselliella, Tinea pellionella, Hofmannophila pseudospretella, Cacoecia*

*podana, Capua reticulana, Choristoneura fumniferana, Clysia ambiguella, Homona magnanima* and *Tortix viridana.*

From the order of the Coleoptera, for example, *Anobium punctatum, Rhizopertha dominica, Acanthoscelides obtectus, Bruchidius obtectus, Hylotrupes bajulus, Agelastica alni, Leptinotarsa decemlineata, Phaedon cochleariae,* Diabrotica spp., *Psylliodes chrysocephala, Epilachna varivestis,* Atomaria spp., *Oryzaephilus surinamensis,* Anthonomus spp., Sitophilus spp., *Otiorrhynchus sulcatus, Cosmopolites sordidus, Ceuthorrhynchus assimilis, Hypera postica,* Dermestes spp., Trogoderma spp., Anthrenus spp., Attagenus spp., Lyctus spp., *Meligethes aeneus,* Ptinus spp.. *Niptus hololeucus, Gibbium psylloides,* Tribolium spp., *Tenebrio molitor,* Agriotes spp., Conoderus spp., *Melolontha melolontha, Amphimallon solstitialis and Costelytra zealandica.*

From the order of the Hymenoptera, for example, Diprion spp., Hoplocampa spp., Lasius spp., *Monomorium pharaonis* and Vespa spp.

From the order of the Diptera, for example, Aedes spp., Anopheles spp., Culex spp., *Drosophila melanogaster,* Musca spp., Fannia spp., *Calliphora erythrocephala,* Lucilia spp., Chrysomyia spp., Cuterebra spp., Gastrophilus spp., Hyppobosca spp., Stomoxys spp., Oestrus spp., Hypoderma spp., Tabanus spp., Tannia spp., *Bibio hortulanus, Oscinella frit,* Phorbia spp., *Pegomyia hyoscyami, Ceratitis capitata, Dacus oleae* and *Tipula paludosa.*

From the order of the Siphonaptera, for example, *Xenopsylla cheopis* and Ceratophyllus spp..

From the order of the Arachnida, for example, *Scorpio maurus* and *Latrodectus mactans.*

From the order of the Acarina, for example, *Acarus siro,* Argas spp., Ornithodoros spp., *Dermanyssus gallinae, Eriophyes ribis, Phyllocoptruta oleivora,* Boophilus spp., Rhipicephalus spp., Amblyomma spp., Hyalomma spp., Ixodes spp., Psoroptes spp., Chorioptes spp., Sarcoptes spp., Tarsonemus spp., *Bryobia praetiosa,* Panonychus spp. and Tetanychus spp.

The novel active compounds are distinguished by having high insecticidal and acaricidal activity.

They can be employed particularly successfully for controlling plant-damaging mites, such as, for example, the common spider mite or the glass house red spider mite (*Tetranychus urticae*) or the fruit tree red spider mite (*Panonychus ulmi*).

The novel active compounds also exhibit a fungicidal activity, for example against *Pyricularia oryzae* on rice.

The active compounds can be converted into the customary formulations, such as solutions, emulsions, wettable powders, suspensions, powders, dustable powders, pastes, soluble powders, granules, suspension/emulsion concentrates, natural and synthetic materials impregnated with active compound, as well as very fine capsules in polymeric substances and in coating compositions for seed, and additionally in formulations used with burning equipment, such as fumigating cartridges, fumigating cans, fumigating coils and the like, as well as ULV cold mist and warm mist formulations.

These formulations are produced in a known manner, for example by mixing the active compounds with extenders, that is, liquid solvents and/or solid carriers, optionally with the use of surface-active agents, that is, emulsifying agents and/or dispersing agents, and/or foarn-forming agents.

In the case of the use of water as an extender, organic solvents can, for example, also be used as auxiliary solvents. As liquid solvents, there are suitable in the main: aromatics, such as xylene, toluene or alkyhaphthalenes, chlorinated aromatics or chlorinated aliphatic hydrocarbons, such as chlorobenzenes, chloroethylenes or methylene chloride, aliphatic hydrocarbons, such as cyclohexane or paraffins, for example petroleum fractions, mineral and vegetable oils, alcohols, such as butanol or glycol as well as their ethers and esters, ketones, such as acetone, methyl ethyl ketone, methyl isobutyl ketone or cyclohexanone, strongly polar solvents, such as dimethylformamide and dimethyl sulfoxide, as well as water; by liquefied gaseous extenders or carriers are meant liquids which are gaseous at ambient temperature and under standard pressure, for example aerosol propellants, such as halogenated hydrocarbons as well as butane, propane, nitrogen and carbon dioxide; as solid carriers there are suitable: for example ammonium salts and ground natural minerals, such as kaolins, clays, talc, chalk, quartz, attapulgite, montmorillonite or diatomaceous earth, and ground synthetic minerals, such as highly disperse silica, montmorillonite or diatomaceous earth, and sground synthetic minerals, such as highly-disperse silica, alumina and silicates; as solid carriers for granules there are suitable: for example crushed and fractionated natural rocks such as calcite, marble, pumice, sepiolite and dolomite, as well as synthetic granules of inorganic and organic meals, and granules of organic material such as sawdust coconut shells, maize cobs and tobacco stalks; as emulsifying and/or foam-forming agents there are suitable: for example nonionic and anionic emulsifiers, such as polyoxyethylene fatty acid esters, polyoxyethylene fatty alcohol ethers, for example alkylaryl polyglycol ethers, alkylsulfonates, alkyl sulfates, arylsulfonates as well as albumen hydrolysis products; as dispersing agents there are suitable: for example ligninsulfite waste liquors and methylcellulose.

Adhesives such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Other additives can be mineral and vegetable oils.

It is possible to use colorants such as inorganic pigments, for example iron oxide, titanium oxide and Prussian Blue, and organic dyestuffs, such as alizarin dyestuffs, azo dyestuff and metal phthalocyanine dyestuffs, and trace nutrients such as salts of iron, manganese, boron, copper, cobalt, molybdenum and zinc.

The formulations in general contain between 0.1 and 95 percent by weight of active compound, preferably between 0.5 and 90%.

In their commercially available formulations, and also in the application forms prepared from the formulations, the novel active compounds may be mixed with other active compounds, such as insecticides, attractants, sterilizing agents, acaricides, nematicides, fungicides, growth-regulating substances or herbicides. The insecticides include, for example, phosphoric esters, carbamates, carboxylic esters, chlorinated hydrocarbons, phenylureas, substances produced by microorganisms, etc.

The following compounds may be mentioned:
acrinathrin, alphamethrin, betacyfluthrin, bifenthrin, brofenprox, cis-resmethrin, clocythrin, cycloprotrin, cyfluthrin, cyhalothrin, cypermethrin, deltamethrin, esfenvalerate, etofenprox, fenpropathrin, fenvalerate, flucythrinate, fluvalinate, lambdacyhalothrin, pyresmethrin, pyresmethrin, silafluofen, tralomethrin,, zetamethrin,
alanycarb, bendiocarb, benfuracarb, bufencarb, butocarboxim, carbaryl, cartap, ethiofencarb, fenobucarb, fenoxycarb, isoprocarb, methiocarb, methomyl, metolcarb, oxamyl, pirimicarb, promecarb, propoxur, terbam, tiodicarb, thiofanox, trirnethacarb, XMC, xylylcarb, acephate, azinophos A, azinophos M bromophos A, cadusafos, carbophenothion, chlorfenvinphos, chlormephos, chlorpyrifos, chlorpyrifos M, cyanophos, demeton M, demeton-S-methyl, demeton S, diazinon, dichlorvos, dicliphos, dichlorfenthion, dicrotophos, dimethoate, dimethylvinphos, dioxathion, disulfoton, edifenphos, ethion, etrimphos, fenitrothion, fenthion, fonophos, formothion, heptenophos, iprobenfos, isazophos, isoxathion, phorate, malathion, mecarbam, mervinphos, mesulfenphos, methacrifos, methamidophos, naled, omethoate, oxydemeton M, oxydeprofos, parathion A, parathion M phenthoate, phorate, phosalone, phosmet, phosphamidon, phoxim, pirimiphos A, picrimiphos M, propaphos, prothiophos, prothoate, pyraclophos, pyridaphenthion, quinalphos, salithion, sebufos, sulfotep, sulprofos, tetrachlorvinphos, temephos, thiomethon, thionazin, trichlorfon, triazophos, vamidothion, buprofezin, chlorfluazuron, diflubenzuron, flucyloxuron, flufenoxuron, hexaflumuron, pyriproxifen, tebufenozide, teflubenzuron, triflumuron, imidacloprid, nitenpyram, N-[(6chloro-3-pyridinyl) methyl]-N'-cyano-N-methylethaneimideamide (NI-25), abamectin, amitrazin, avermectin, azadirachtin, bensultap, Bacillus thuringiensis, cyromazine, diafenthiuron, emamectin, ethofenprox, fenpyrad, fipronil, flufenprox, lufenuron, metaldehyde, milbemectin, pymetrozine, tebufenpyrad, triazuron, aldicarb, bendiocarb, benfuracarb, carbofuran, carbosulfan, chlorethoxyfos, cloethocarb, disulfoton, ethophrophos, etrimphos, fenamiphos, fipronil, fonofos, fosthiazate, furathiocarb, HCH, isazophos, isofenphos, methiocarb, monocrotophos, nitempyran, oxamyl, phorate, phoxim, prothiofos, pyrachlofos, sebufos, silafluofen, tebupirimphos, tefluthrin, terbufos, thiodicarb, thiafenox, azocyclotin, butylpyridaben, clofentezine, cyhexatin, diafenthiuron, diethion, emamectin, fenazaquin, fenbutatin oxide, fenothiocarb, fenpropathrin, fenpyrad, fenpyroximate, fluazinam, fluazuron, flucycloxuron, flufenoxuron, fluvalinate, fubfenprox, hexythiazox, ivermectin, methidathion, monocrotophos, moxidectin, naled, phosalone, profenofos, pyraclofos, pyridaben, pyrimidifen, tebufenpyrad, thuringiensin, triarathene and also 4bromo-2-(4chlorophenyl)-1-(ethoxymethyl)-5-(trifluoromethyl)-1H-pyrrole-3-carbonitrile (AC 303630).

The novel active compounds can also, in their commercially available formulations and also in the application forms prepared from these formulations, be mixed with synergists. Synergists are compounds which augment the effect of the active compounds without the added synergist itself having to be active.

The content of active compound in the application forms prepared from the commercially available formulations can vary in wide ranges. The concentration of active compound in the application forms can be from 0.0000001 up to 95% by weight of active compound, preferably between 0.0001 and 1% by weight.

The use forms are used in a customary manner which is suitable for them.

The active compounds according to the invention are not only active against plant, hygiene and stored-product pests but also, in the veterinary sector, against animal parasites (ectoparasites ) such as ixodid ticks, argasid ticks, mange mites, harvest mites, flies (biting and licking), parasitizing fly larvae, lice, biting lice, bird lice, fleas. For example, they are outstandingly effective against ticks, such as, for example, Boophilus microplus.

The active compounds of the formula I are also suitable for controlling arthropods which infest agricultural productive livestock such as, for example, cattle, sheep, goats, horses, pigs, donkeys, camels, buffalo, rabbits, chickens, turkeys, ducks, geese and bees, other pets, such as, for example, dogs, cats, cage birds and aquarium fish, and also so-called test animals, such as, for example, hamsters, guinea pigs, rats and mice. By combating these arthropods cases of death and reductions in productivity (for meat, milk, wool, hides, eggs, honey etc) should be diminished, so that more economic and simpler animal husbandry is possible by use of the active compounds according to the invention.

The active compounds according to the invention are used in the veterinary sector in a known manner by enteral administration in the formn of, for example, tablets, capsules, potions, drenches, granules, pastes, boli, the feed-through process and suppositories, by parenteral administration, such as, for example, by injections (intramuscular, subcutaneous, intravenous, intraperitoneal etc), implants, by nasal administration, by dermal use in the forn, for example, of dipping or bathing, spraying, pouring on and spotting on, washing and powdering, and also with the aid of moulded articles containing the active compound, such as collars, ear marks, tail marks, limb bands, halters, marking devices, etc.

The preparation and the use of the novel compounds are illustrated by the following examples:

Preparation Examples

Example (Ia-1)

4Hydroxy-1-thia-3-mesityl-spiro[4.5]dec-3-en-2-one

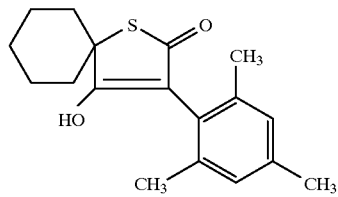

68 g of 4-4-methoxybenzylmercapto-3-oxo4,4-pentamethylene-2-(2,4,6-trimethylphenyl)-butyric acid are dissolved in 200 ml of trifluoroacetic acid and this solution is boiled under reflux for one hour. TIhe solvent is then evaporated off and the residue (black oil) is taken up in ether (200 ml) and water (1 l). NaOH is then added until the pH is 14 and decanting then takes place. The aqueous phase is acidified with conc. HCl and extracted with ether (two times 200 ml). The organic phase is dried ($MgSO_4$) and concentrated by evaporation. The residue crystallizes under high vacuum. The crystals are washed with a little cyclohexane.

White solid, m.p.: 224° C.

Yield: 23.5 g (62%)

$^1$H-NMR (100 MHz, $CDCl_3$): 1.25–2.00 (m, 8H); 2.15 (s, 6H); 2.20 (m, 2H); 2.30 (s, 3H); 6.95 (s, 2H).

$^{13}$C NMR(CDCl$_3$): 19.6, 21.1, 24.7, 24.8, 35.9, 60.7, 114.5, 124.5, 128.7, 138.4, 138.8, 180.0, 193.5.

The following compounds of the formula (Ia) were prepared in anaogy with Example (Ia-1) and in accordance with the general preparation instructions:

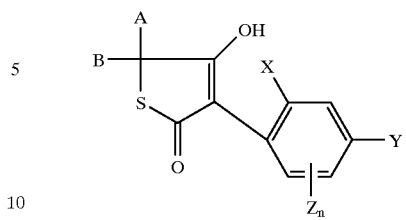

(Ia)

TABLE 14

| Ex. No. | A | B | X | Z$_n$ | Y | M.p. |
|---|---|---|---|---|---|---|
| Ia-2 | (2-ethyl-4-chloro-6-chlorophenyl) | CH$_3$ | CH$_3$ | 6-CH$_3$ | CH$_3$ | 172 |
| Ia-3 | —(CH$_2$)$_5$— | | Cl | H | Cl | 245 |
| Ia-4 | —(CH$_2$)$_2$—CHOCH$_3$(CH$_2$)$_2$— | | CH$_3$ | 6-CH$_3$ | CH$_3$ | 178 |
| Ia-5 | —(CH$_2$)$_2$—CHOCH$_3$—(CH$_2$)$_2$— | | Cl | H | Cl | 249 |
| Ia-6 | —(CH$_2$)$_2$—CHCH$_3$—(CH$_2$)$_2$— | | CH$_3$ | 6-CH$_3$ | CH$_3$ | 224 |
| Ia-7 | —(CH$_2$)$_2$—CHCH$_3$—(CH$_2$)$_2$— | | Cl | H | Cl | 248 |
| Ia-8 | (o-xylylene) | | CH$_3$ | 6-CH$_3$ | CH$_3$ | 225 |
| Ia-9 | (o-xylylene) | | Cl | H | Cl | 268 |
| Ia-10 | (2-ethyl-3,4-dichlorophenyl) | CH$_3$ | Cl | H | Cl | 248 |
| Ia-11 | —(CH$_2$)$_5$— | | CH$_3$ | H | CH$_3$ | 199 |
| Ia-12 | —(CH$_2$)$_6$— | | CH$_3$ | 6-CH$_3$ | CH$_3$ | 220 |
| Ia-13 | —(CH$_2$)$_6$— | | Cl | H | Cl | 236 |
| Ia-14 | —(CH$_2$)$_4$— | | CH$_3$ | 6-CH$_3$ | CH$_3$ | 211 |
| Ia-15 | —(CH$_2$)$_4$— | | CH$_3$ | H | CH$_3$ | 156 |
| Ia-16 | —(CH$_2$)$_4$— | | Cl | H | Cl | 198 |
| Ia-17 | —(CH$_2$)$_2$—CHOCH$_3$—(CH$_2$)$_2$— | | —(CH=CH)$_2$— | | H | 224 |
| Ia-18 | —(CH$_2$)$_2$—CHCH$_3$—(CH$_2$)$_2$— | | —(CH=CH)$_2$— | | H | 224 |
| Ia-19 | —(CH$_2$)$_5$— | | —(CH=CH)$_2$— | | H | 215 |
| Ia-20 | (o-xylylene) | | CH$_3$ | H | CH$_3$ | 222 |
| Ia-21 | —(CH$_2$)$_2$—CHCH$_3$—(CH$_2$)$_2$— | | CH$_3$ | H | CH$_3$ | 208 |

Example (IIb-1)

4-Acetoxy-1-thia-3-mesityl-spiro[4,5]dec-3-en-2-one

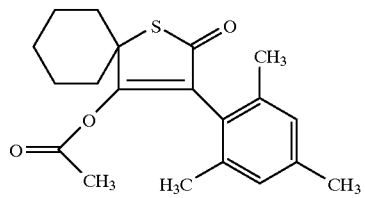
(Ib-1)

A mixture of the compound according to Example (Ia-1) (0.906 g), triethylamine (1 ml) and acetyl chloride (0.5 ml) in toluene (10 ml) is boiled under reflux for 2 hours and is diluted, after having been cooled, with 100 ml of ethyl ether. The resulting suspension is filtered through silica gel and concentrated. 848 mg (82%) are obtained of the compound indicated above, with a m.p. of 150° C.

The following compounds of the formula (Ib) were prepared in anaogy with Example (Ib-1) and in accordance with the general preparation instuctions:

TABLE 15

(Ib)

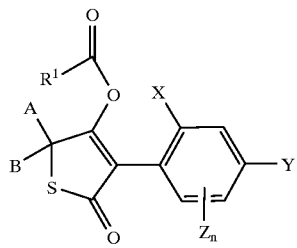

| Ex. No. | A | B | X | Y | $Z_n$ | $R^1$ | M.p. ° C. |
|---|---|---|---|---|---|---|---|
| Ib-2 | —(CH$_2$)$_5$— | | CH$_3$ | CH$_3$ | 6-CH$_3$ | t-C$_4$H$_9$— | 127 |
| Ib-3 | —(CH$_2$)$_5$— | | Cl | Cl | H | t-C$_4$H$_9$— | 144 |
| Ib-4 | —(CH$_2$)$_5$— | | CH$_3$ | CH$_3$ | 6-CH$_3$ | ClCH$_2$(CH$_3$)$_2$C— | 187 |
| Ib-5 | —(CH$_2$)$_5$— | | Cl | Cl | H | ClCH$_2$(CH$_3$)$_2$C— | 153 |
| Ib-6 | —(CH$_2$)$_5$— | | CH$_3$ | CH$_3$ | 6-CH$_3$ | Br—CH$_2$— | 141 |
| Ib-7 | —(CH$_2$)$_5$— | | CH$_3$ | CH$_3$ | 6-CH$_3$ | Cl—CH$_2$— | 144 |
| Ib-8 | —(CH$_2$)$_5$— | | CH$_3$ | CH$_3$ | 6-CH$_3$ | Cl$_3$C— | 163 |
| Ib-9 | —(CH$_2$)$_5$— | | CH$_3$ | CH$_3$ | 6-CH$_3$ | H$_3$CO—CH$_2$— | 110 |
| Ib-10 | —(CH$_2$)$_5$— | | Cl | Cl | H | CH$_3$— | 113 |
| Ib-11 | —(CH$_2$)$_5$— | | Cl | Cl | H | Cl—CH$_2$— | 110 |
| Ib-12 | —(CH$_2$)$_4$— | | CH$_3$ | CH$_3$ | H | Cl—CH$_2$— | 115 |
| Ib-13 | —(CH$_2$)$_4$— | | CH$_3$ | CH$_3$ | 6-CH$_3$ | Cl—CH$_2$— | 134 |
| Ib-14 | —(CH$_2$)$_4$— | | Cl | Cl | H | Cl—CH$_2$— | 113 |
| Ib-15 | —(CH$_2$)$_5$— | | CH$_3$ | CH$_3$ | H | Cl—CH$_2$— | 124 |
| Ib-16 | —(CH$_2$)$_6$— | | Cl | Cl | H | Cl—CH$_2$— | 122 |
| Ib-17 | —(CH$_2$)$_2$—CHCH$_3$—(CH$_2$)$_2$— | | CH$_3$ | CH$_3$ | H | CH$_3$ | 132 |
| Ib-18 | —(CH$_2$)$_2$—CHCH$_3$—(CH$_2$)$_2$— | | CH$_3$ | CH$_3$ | H | Cl—CH$_2$— | 134 |
| Ib-19 | benzo-bis(CH$_2$—) | | CH$_3$ | CH$_3$ | H | CH$_3$ | 112 |
| Ib-20 | benzo-bis(CH$_2$—) | | CH$_3$ | CH$_3$ | H | Cl—CH$_2$— | oil |
| 21 | benzo-bis(CH$_2$—) | | CH$_3$ | CH$_3$ | H | n-C$_4$H$_9$—CH(C$_2$H$_5$)— | oil |

Example (Ic-1)

(IC-1)

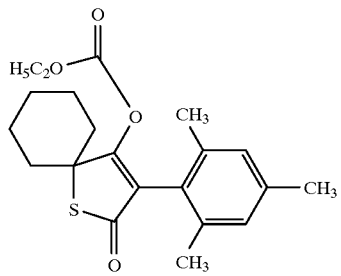

4-Ethoxycarbonyloxy-1-thia-3-mesityl-spiro[4.5]-dec-3-en-2-one

A mixture of the compound according to Example (Ia-1) (0.906 g), triethylamnine (1 ml) chloroformate (0.6 ml) in toluene (10 ml) is boiled under reflux for 2 hours and, after having been cooled down, diluted with 100 ml of ethyl ether. The resulting suspension is filtered through silica gel and concentrated. 830 mg (74%) are obtained of the compound shown above, with a mp. of 143° C.

The following compounds of the formula (Ic) were prepared in analogy with Example (Ic-1) and in accordance with the general preparation instctions:

TABLE 16

(Ic)

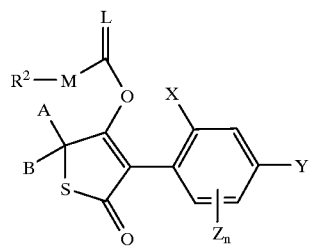

| Ex No. | A | B | L | M | X | Y | $Z_n$ | $R^2$ | M.p. ° C. |
|---|---|---|---|---|---|---|---|---|---|
| Ic-2 | —(CH$_2$)$_5$— | | O | O | CH$_3$ | CH$_3$ | 6-CH$_3$ | CH$_3$— | 130 |
| Ic-3 | —(CH$_2$)$_5$— | | O | O | CH$_3$ | CH$_3$ | 6-CH$_3$ | i-C$_3$H$_7$— | 124 |
| Ic-4 | —(CH$_2$)$_5$— | | O | O | CH$_3$ | CH$_3$ | 6-CH$_3$ | CH$_2$=CH— | 175 |
| Ic-5 | —(CH$_2$)$_6$— | | O | O | CH$_3$ | CH$_3$ | 6-CH$_3$ | CH$_3$— | 87 |
| Ic-6 | —(CH$_2$)$_5$— | | O | O | Cl | Cl | H | CH$_3$— | 103 |
| Ic-7 | —(CH$_2$)$_4$— | | O | O | Cl | Cl | H | CH$_3$— | 116 |
| Ic-8 | —(CH$_2$)$_5$— | | O | O | CH$_3$ | CH$_3$ | H | CH$_3$— | oil |
| Ic-9 | —(CH$_2$)$_6$— | | O | O | Cl | Cl | H | CH$_3$— | 100 |
| Ic-10 | —(CH$_2$)$_4$— | | O | O | CH$_3$ | CH$_3$ | 6-CH$_3$ | CH$_3$— | 83 |
| Ic-11 | —(CH$_2$)$_4$— | | O | O | CH$_3$ | CH$_3$ | H | CH$_3$— | oil |
| Ic-12 | —(CH$_2$)$_4$— | | O | O | Cl | Cl | H | i-C$_3$H$_7$— | 90 |
| Ic-13 | —(CH$_2$)$_5$— | | O | O | Cl | Cl | H | i-C$_3$H$_7$— | 102 |
| Ic-14 | —(CH$_2$)$_5$— | | O | O | CH$_3$ | CH$_3$ | H | i-C$_3$H$_7$— | 123 |
| Ic-15 | o-C$_6$H$_4$(CH$_2$—)$_2$ | | O | O | CH$_3$ | CH$_3$ | H | CH$_3$— | 107 |
| Ic-16 | o-C$_6$H$_4$(CH$_2$—)$_2$ | | O | O | CH$_3$ | CH$_3$ | H | i-C$_3$H$_7$— | Oil |

Example (Id-1)

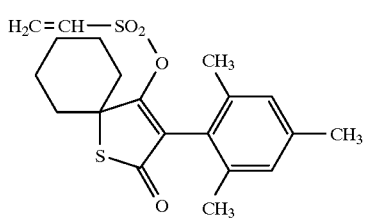

4-Vinylsulfonyloxy-1-thia-3-mesityl-spiro[4.5]-dec-3-en-2-one

A mixture of the compound according to Example (Ia-1) (0.604 g), triethylamine (1 ml) and 2-chloroethylsulfonyl chloride (0.318 ml) in toluene (10 ml) is boiled under reflux for 2 hours and, after it has been cooled down, diluted with 100 ml of ethyl ether. The resulting suspension is filtered through silica gel and concentrted. 421 mg (54%) are obtained of the compound shown above with an m.p. of 122° C.

Preparation of the starting compounds

Example (XVI-1)

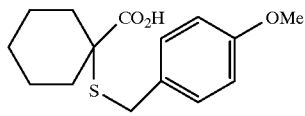

1-(4Methoxybenzylmercapto)cyclohexane-1-carboxylic acid

Butyllithium (1.6 M in hexane, 60 ml) is added, at −78° C., to a solution of diisopropylamine (14.8 ml) in THF (80 ml). After a few minutes, methyl cyclohexane carboxylate (11.4 g) is added dropwise and the solution is stirred at −78° C. for 1 hour. Bis-4-methoxybenzyl disulfide (24.3 g) is then added and the temperature is raised to 20° C. The mixture is then diluted with ether (200 ml), and this diluted mixture is washed with water (100 ml), dried (MgSO$_4$) and then concentrated. The solid residue is washed with cold petroleum ether and dissolved in 200 ml of methanol. 21 g of potassium hydroxide are added. The mixture is heated under reflux for 2 hours and then concentrated. The solid residue is taken up in water and washed with ether (two times 100 ml). This aqueous phase is acidified with concentrated HCl and extracted with ether (two times 300 ml). The resulting organic phase is dried (MgSO$_4$) and concentrated by evaporation. The solid residue is washed with petroleum ether. 14.5 g (86%) are obtained of the compound shown above with a mp. of 98° C.

The following compounds of the formula (XVI) were prepared in analogy with Example XVI-1 and in accordance with the general preparation instructions:

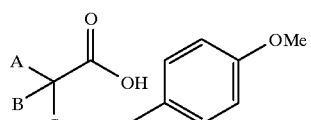

| Ex. No. | A | B | M.p. (° C.) |
|---|---|---|---|
| XVI-2 | —CH$_3$ | —CH$_2$—(2,4-dichlorophenyl) | 111 |
| XVI-3 | —CH$_2$—CH$_2$—CH$_2$—CH$_2$— | | 80 |
| XVI-4 | —CH$_2$—CH$_2$—CH$_2$—CH$_2$—CH$_2$—CH$_2$— | | 80 |
| XVI-5 | —H$_2$C—(o-phenylene)—CH$_2$— | | 169 |
| XVI-6 | —CH$_2$—CH$_2$—CH(CH$_3$)—CH$_2$—CH$_2$— | | oil |
| XVI-7 | —CH$_2$—CH$_2$—CH(OCH$_3$)—CH$_2$—CH$_2$— | | 173–5 |

Example II-1

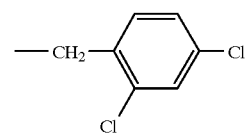

a) 1-(4-Methoxybenzylthio)cyclohexanecarbonyl chloride One drop of DMF and 4.4 ml of thionyl chloride are added to a suspension of 11.2 g of the compound according to Example (XVI-1) in 40 ml of toluene. After a few minutes, the mixtu is heated at 100° C. until the evolution of gas is complete (approximately 10 minutes). After the mixture has been concentrated by evaporation, 12 g are obtained of a yellow oil which is immnediately subjected to fuirther reaction.

b) Butyllithium (1.6 M in hexane; 56 ml) is added, at 0° C., to a mixture of diisopropylamine (14 ml) in THF (100 ml). After a few minutes, methyl mesityl acetate (15.4 g) is added and the mixture is then stirred at 0° C. for 30 minutes. 1-(4Methoxybenzylthio)-cyclohexanecarbonyl chloride from a) is then added slowly and the mixture is warmed to room temperature. After one hour, the reaction mixture is diluted with ether (200 ml) and washed twice with a 10% strength aqueous solution of ammonium chloride; it is then dried (MgSO$_4$) and concentrated by evaporation. The product crystallizes out slowly under high vacuum. The crystals are washed with a little petroleum ether. M.p.=109° C.

Yield 13.4 g (74%)

$^1$H-NMR (100 MHz, CDCl$_3$): 1.20–1.80 (m, 8H); 1.90–2.00 (m, 2H); 2.30 (s, 3H); 2.40 (s, 6H); 3.20 (d, 1H, J=12 Hz); 3.40 (d, 1, J=12 Hz); 3.80 (2s, 6H); 6.00 (s, 1H); 6.80 (d, 2H, J=10 Hz); 6.90 (s, 2H); 7.05 (d, 2H, J=10 Hz).

The other compounds of the formula (II), which were employed inmnediately in process A and not charterized analytically, were prepared in analogy with Example II-1.

Use Examples

Example A

Phaedon larvae test

Solvent: 7 parts by weight of dimethylformamide

Emulsifier: 1 part by weight of alkylaryl polyglycol ether

In order to prepare a suitable preparation of active compound, 1 part by weight of active compound is mixed with the given quantity of solvent and the given quantity of emulsifier, and the concentrate is diluted with water to the desired concentration.

Cabbage leaves (Brassica oleracea) are treated by being dipped into the active compound preparation of the desired concentration and infested with mustard beetle larvae (Phaedon cochleariae) while the leaves are still moist.

After the desired time, the destruction in % is determined. 100% means that all the beetle larvae have been killed, 0% means that none of the beetle larvae was killed.

In this test, the compounds according to Preparation Examples (Ia-6), (Ia-7), (Ia-9), (Ia-11), (Ib-9) and (Ib-10), for example, produced, at an exemplary active compound concention of 0.1%, a destruction of 100% after 7 days.

Example B

Plutella test

Solvent: 7 parts by weight of dimethylfonramide

Emulsifier: 1 part by weight of alkylaryl polyglycol ether

To prepare a suitable preparation of active compound, 1 part by weight of active compound is mixed with the stated quantity of solvent and the stated quantity of emulsifier, and the concentrate is diluted with water to the desired concentration.

Cabbage leaves (Brassica olermcea) are treated by being dipped into the active compound preparation of the desired concentration and infested with caterpillars of the cabbage moth (Plutella maculipennis) while the leaves are still moist.

After the desired time, the destruction is deteriined in %. 100% means that all the caterpillars have been killed; 0% means that none of the caterpillars has been killed.

In this test, the compounds according to Preparation Examples (Ia-6), (Ia-7), (Ia-9), (Ia-11), (Ib-3), (Ib-9) and (Ib-10), for example, produced, at an exemplary active compound concentration of 0.1%, a destruction of 100% after 7 days.

Example C

Nephotettix test

Solvent: 7 parts by weight of dimethylformamide

Emulsifier: 1 part by weight of alkylaryl polyglycol ether

To prepare a suitable preparation of active compound, 1 part by weight of active compound is mixed with the stated quantity of solvent and the stated quantity of emulsifier, and the concentrate is diluted with water to the desired concentration.

Rice seedlings (Oryza sativa) are treated by being dipped into the active compound preparation of the desired concentration and infested with the green rice leaf hopper (Nephotettix cincticeps) while the seedlings are still moist.

After the desired time, the destruction in % is determined. 100% means that all the leaf hoppers have been killed; 0% means that none of the leaf hoppers has been killed.

In this test, the compounds according to Preparation Examples (Ia-6) and (Ia-11), for example, produced, at an exemplary active compound concentration of 0.1%, a destruction of 100% after 6 days.

Example D

Spodoptera test

Solvent: 7 parts by weight of dimethylformamide

Emulsifier: 1 part by weight of alkylaryl polyglycol ether

To prepare a suitable preparation of active compound, 1 part by weight of active compound is mixed with the stated quantity of solvent and the stated quantity of emulsifier, and the concentrate is diluted with water to the desired concentration.

Cabbage leaves (Brassica oleracea) are treated by being dipped into the active compound preparation of the desired concentration and infested with caterpillars of the leafworm (Spodoptera frugiperda) while the leaves are still moist.

After the desired time, the destruction in % is determined. 100% means that all the caterpillars have been killed; 0% means that none of the caterpillars has been killed.

In this test, the compounds according to Preparation Examples (Ia-9), (Ia-11), (Ib-9) and (Ib-10), for example, produced, at an exemplary active compound concentration of 0.1%, a destruction of at least 95% after 7 days.

Example E

Panonychus test

Solvent: 3 parts by weight of dimethylformamide

Emulsifier: 1 part by weight of alkylaryl polyglycol ether

To prepare a suitable preparation of active compound, 1 part by weight of active compound is mixed with the stated quantity of solvent and the stated quantity of emulsifier, and the concentrate is diluted with water containing the emulsifier to the desired concentration.

Young plum trees (Pnmus domestica) of about 30 cm in height, which are heavily infested with all stages of the fruit tree red spider mite Panonychus ulmi, are sprayed with an active compound preparation of the desired concentrtion.

After the desired time, the effect is determined in %. 100% means that all the spider mites have been killed; 0% means that none of the spider mites has been killed.

In this test, the compound according to Preparation Example (Ib-7), for example, produced, at an exemplary active compound concentration of 0.02%, a destruction of 100% afier 14 days.

Example F

Tetranychus test (OP-resistant/spray treatment)

Solvent: 3 parts by weight of dimethylformamide

Emulsifier: 1 part by weight of alkylaryl polyglycol ether

To prepare a suitable preparation of active compound, 1 part by weight of active compound is mixed with the stated quantity of solvent and the stated quantity of emulsifier, and the concentrate is diluted with water containing the emulsifier to the desired concentration.

Bean plants (Phaseolus vulgaris), which are heavily infested with all stages of the common red spider mite (Tetranychus urticae), are sprayed with an active compound preparation of the desired concentration.

After the desired time, the effect is determined in %. 100% means that all the spider mites have been killed; 0% means that none of the spider mites has been killed.

The compounds according to Preparation Examples (Ia-1), (Ia-3), (Ic-2) and (Ic-3) produced, at an exemplary active compound concentration of 0.02%, a destruction of at least 95% after 7 days.

Example G
Blowfly larvae test/Development-inhibiting effect

Experimental animals: Lucilia cuprina larvae

Solvents: 35 parts by weight of ethylene glycol monomethyl ether 35 parts by weight of nonylphenol polyglycol ether To prepare a suitable preparation of active compound, three parts by weight of active compound are mixed with seven parts by weight of the abovementioned mixture, and the concentrate thus obtained is diluted with water to the concentration which is desired in each case.

Approximately 20 Lucilia cuprina res. larvae are placed in a test tube which contains approximately 1 cm³ of horse flesh and 0.5 ml of the preparation of active compound to be tested.

The test tubes are transferred to beakers having a sand-covered base. After 2 days, the test tubes are removed and the pupae are counted. The effect of the preparation of the active compound is assessed in accordance with the number of flies which have hatched after 1.5 times the period taken for an untreated control to develop. In this context, 100% means that no flies hatched; 0% means that all the flies hatched normally.

In this test, the compound according to Preparation Example (Ia-1), for example, had, at an exemplary active compound concentration of 1000 ppm, an effect of 100%.

Example H
Test using resistant *Boophilus microplus* resistant/SP-resistant Parkhurst strain Experimental animals: Adult females which have sucked blood Solvent: Dimethyl sulfoxide 20 mg of active compound are dissolved in 1 ml of dimethyl sulfoxide, with lower concentrations being prepared by diluting with the same solvent.

The test is carried out in quintuplicate. 1 μl volumes of the solution are injected into the abdomen and the animals are transferred to dishes and stored in an air conditioned room. The effect is determined on the basis of inhibition of egg laying. In this context, 100% means that no tick has laid eggs.

In this test, the compounds according to Preparation Examples (Ia-1), (Ib-7) and (Ic-3), for example, had in each case, at an exemplary active compound concentration of 20 μg/animal, an effect of 100%.

We claim:

1. A 3-ary-4-hydroxy-Δ³-dihydrothiophenone derivative of the formula

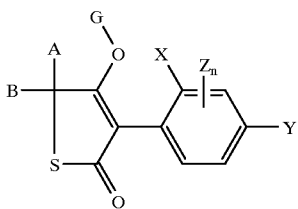

(I)

in which

X represents $C_1$–$C_6$-alkyl, halogen, $C_1$–$C_6$-alkoxy or $C_1$–$C_3$-haogenoalkyl, Y represents hydrogen, $C_1$–$C_6$-alkyl, halogen, $C_1$–$C_6$-alkoxy or $C_1$–$C_3$-halogenoalkyl, Z represents $C_1$–$C_6$-alkyl, halogen or $C_1$–$C_6$-alkoxy, n represents a number 0 or 1 or

A and B represent, together with the carbon atom to which they are bonded, a saturated 3- to 8-membered ring which is optionally substituted identically or differently once or more than once by $C_1$–$C_6$-alkyl, $C_1$–$C_6$-alkoxy, G rempents hydrogen (a) or rprents one of the groups (b)

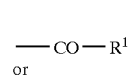

or (c)

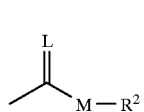

in which

L represents oxygen, and

M represents oxygen or sulfur, $R^1$ represents $C_1$–$C_{20}$-alkyl, $C_2$–$C_{20}$-alkenyl, $C_1$–$C_8$-alkoxy-$C_1$–$C_8$-alkyl, $C_1$–$C_8$-alkylthio-$C_1$–$C_8$-alkyl or $C_1$–$C_8$-polyalkoxy-$C_2$–$C_8$-alkyl which are in each case optionally substituted identically or differently once or more than once by halogen or cycloalkyl having 3 to 8 ring atoms which is optionally substituted by halogen or $C_1$–$C_6$-alkyl represents phenyl wich is optionally substituted identically or diffently once or more than once by halogen, nitro, $C_1$–$C_6$-alkyl, $C_1$–$C_6$-alkoxy, $C_1$–$C_6$-halogenoalkyl or $C_1$–$C_6$-halogeoalkoxy, presents phenyl-$C_1$–$C_6$-alkyl which is optionally substituted identically or differently once or more than once by halogen, $C_1$–$C_6$-alkyl, $C_1$–$C_6$-alkoxy, $C_1$–$C_6$-halogenoalkyl or $C_1$–$C_6$-halogenoalkoxy, represents phenoxy-$C_1$–$C_6$-alkyl which is optionally substituted identically or diffently once or more than once by halogen or $C_1$–$C_6$-alkyl, or $R^2$ represents $C_1$–$C_{20}$-alkyl, $C_2$–$C_{20}$-alkenyl, $C_1$–$C_8$-alkoxy-$C_2$–$C_8$-alkyl or $C_1$–$C_8$-polyalkoxy-$C_2$–$C_8$-alkyl which are in each case optionally substituted identically or diffrently once or more than once by halogen, or represents $C_3$–$C_8$-cycloalkyl which is optionally substituted by halogen, $C_1$–$C_4$-alkyl or $C_1$–$C_4$-alkoxy, or represents phenyl or benzyl which are in each case optionally substiued identically or differently once or more than once by halogen, nitro, $C_1$–$C_6$-alkyl, $C_1$–$C_6$-alkoxy or $C_1$–$C_6$-halogenoalkyl.

2. A 3-aryl-4-hydroxy-Δ³-dihydrothiophenone derivative according to claim 1 in which X represents $C_1$–$C_6$-alkyl, halogen, $C_1$–$C_6$-alkoxy or $C_1$–$C_3$-halogenoalkyl, Y represents hydrogen, $C_1$–$C_6$-alkyl, halogen, $C_1$–$C_6$-alkoxy or $C_1$–$C_3$-halogenoalkyl, Z represents $C_1$–$C_6$-alkyl, halogen or $C_1$–$C_6$-alkoxy, n represents a number 0 or 1

A and B represent, together with the carbon atom to which they are bonded, a saturated 3- to 8-membered ring which is optionally substituted identically or differently once or more than once by $C_1$–$C_6$-alkyl, $C_1$–$C_6$-alkoxy, G presents hydrogen (a) or represents one of the groups

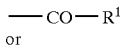

(b)

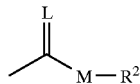

(c)

in which

L represents oxygen, and

M represents oxygen or sulfur,

R$^1$ represents C$_1$–C$_{20}$-alkyl, C$_2$–C$_{20}$-alkenyl, C$_1$–C$_8$-alkoxy-C$_1$–C$_8$-alkyl, C$_1$–C$_8$-alkylthio-C$_1$–C$_8$-alkyl or C$_1$–C$_8$-polyalkoxy-C$_2$–C$_8$-alkyl which are in each case optionally substituted identically or diffently once or more than once by halogen, or cycloalkyl having 3 to 8 ring atoms which is optionally substituted by halogen or C$_1$–C$_6$-alkyl represents phenyl which is optionally substitued identically or differently once or more than once by halogen, nitro C$_1$–C$_6$-alkyl, C$_1$–C$_6$-halogenoalkyl or C$_1$–C$_6$-halogenoalkoxy, represents phenyl-C$_1$–C$_6$-alkyl which is optionally substituted identically or differently once or more than once by halogen, C$_1$–C$_6$-alkyl, C$_1$–C$_6$-alkoxy, C$_1$–C$_6$-halogenalkyl or C$_1$–C$_6$-halogenoalkoxy, represents phenoxy-C$_1$–C$_6$-alkyl which is optionally substituted identically or differently once or more than once by halogen or C$_1$–C$_6$-alkyl, or R$^2$ represents C$_1$–C$_{20}$-alkyl, C$_2$–C$_{20}$-alkenyl, C$_1$–C$_8$-alkoxy-C$_2$–C$_8$-alkyl or C$_1$–C$_8$-polyalkoxy-C$_2$–C$_8$-alkyl which are in each case optionally substituted identically or differently once or more than once by halogen, or represents C$_3$–C$_8$-cycloalkyl which is optionally substituted by halogen, C$_1$–C$_4$-alkyl or C$_1$–C$_4$-alkoxy, or represents phenyl or benzyl which are in each case optionally substituted identically or differently once or more than once by halogen, nitro, C$_1$–C$_6$-alkyl, C$_1$–C$_6$-alkoxy or C$_1$–C$_6$-halogenalkyl.

3. A 3-aryl-4-hydroxy-Δ$^3$-dihydrothiophene derivative according to claim 2, in which X represents C$_1$–C$_6$-alkyl, halogen, C$_1$–C$_6$-alkoxy or C$_1$–C$_2$-halogenoalkyl, Y represents hydrogen, C$_1$–C$_6$-alkyl, halogen, C$_1$–C$_6$-alkoxy or C$_1$–C$_2$-halogenoalkyl, Z represents C$_1$–C$_4$-alkyl, halogen or C$_1$–C$_4$-alkoxy, n represents a number 0 or 1

A and B represent, together with the carbon atom to which they are bonded, a saturated or unsaturated 3 to 8-membered ring which is optionally substituted identically or differently once or more than once by C$_1$–C$_5$-alkyl, C$_1$–C$_5$-alkoxy, G represents hydrogen (a) or represents one of the groups

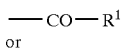

(b)

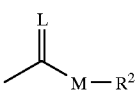

(c)

in which

L represents oxygen,

M represents oxygen or sulfur,

R$^1$ represents C$_1$–C$_{16}$-alkyl, C$_2$–C$_{16}$-alkenyl, C$_1$–C$_6$-alkoxy-C$_1$–C$_6$-alkyl, C$_1$–C$_6$-alkylthio-C$_1$–C$_6$-alkyl or C$_1$–C$_6$-polyalkoxy-C$_2$–C$_6$-alkyl which are in each case optionally substituted identically or differently once or more than once by halogen, or cycloalkyl having 3 to 7 ring atoms which is optionally substituted by fluorine, chlorine or C$_1$–C$_4$-alkyl represents phenyl which is optionally substituted identically or diffently once to five times by halogen, nitro, C$_1$–C$_4$-alkyl, C$_1$–C$_4$alkoxy, C$_1$–C$_3$-halogenoaklyl or C$_1$–C$_3$-halogenoalkoxy, represents phenyl-C$_1$–C$_4$-alkyl which is optionally substituted identically or differently once to five times by halogen, C$_1$–C$_4$-alkyl, C$_1$–C$_4$-alkoxy, C$_1$–C$_3$-halogenoalkyl or C$_1$–C$_3$-halogenoalkoxy, represents phenoxy-C$_1$–C$_3$-alkyl which is optionally substituted identically or differently once to five times by halogen or C$_1$–C$_4$-alkyl, represents C$_1$–C$_{16}$-alkyl, C$_2$–C$_{16}$-alkenyl, C$_1$–C$_6$-alkoxy-C$_2$–c$_6$-alkyl or C$_1$–C$_6$-polyalkoxy-C$_2$–C$_6$-alkyl which are in each case optionally substituted identically or differently once or more than once by halogen, or represents C$_3$–C$_7$-cycloalkyl which is optionally substituted by fluorine, chlorine, C$_1$–C$_3$-alkyl, C$_1$–C$_3$-alkoxy, or represents phenyl or benzyl which are in each case optionally substituted identically or differently once to five times by halogen, nitro, C$_1$–C$_4$-alkyl, C$_1$–C$_3$-alkoxy or C$_1$–C$_3$-halogenoalkyl.

4. A 3-aryl-4-hydroxy-Δ$^3$-dihydrothiophene derivative according to claim 1, in which X represents methyl, ethyl, propyl, i-propyl, fluorine, chlorine, bromine, methoxy, ethoxy, ethoxy or trifluoromethyl, Y represents hydrogen, methyl, ethyl, propyl, i-propyl, butyl, i-butyl, tert-butyl, fluorine, chlorine, bromine, methoxy, ethoxy or trifluoromethyl, Z represents methyl, ethyl, i-propyl, butyl, i-butyl, tert-butyl, fluorine, chlorine, bromine, methoxy or ethoxy, n represents a number 0 or 1

A and B represent, together with the carbon atom to which they are bonded, a saturated 3- to 8-membered ring which is optionally substituted identically or differently once to five times by C$_1$–C$_4$-alkyl, C$_1$–C$_4$-alkoxy, substituted identically or differently once to five times by G represents hydrogen (a) or represents one of the groups

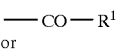

(b)

-continued

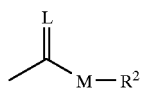
(c)

in which

L represents oxygen,

M represents oxygen or sulfur,

R$^1$ represents $C_1$–$C_{14}$-alkyl, $C_2$–$C_{14}$-alkenyl, $C_1$–$C_4$-alkoxy-$C_1$–$C_6$-alkyl, $C_1$–$C_4$-alkylthio-$C_1$–$C_6$-alkyl or $C_1$–$C_4$-polyalkoxy-$C_2$–$C_4$-alkyl which are in each case optionally substituted identically or differently once to nine times by fluorine or chlorine, or cycloalkyl which has 3 to 6 ring atoms, which is optionally substituted by fluorine, chlorine, methyl or ethyl, represents phenyl which is optionally substituted identically or differently once to three times by fluorine, chlorine, bromine, methyl, ethyl, propyl, i-propyl, methoxy, ethoxy, trifluoromethyl, trifluoromethoxy or nitro, represents phenyl-$C_1$–$C_3$-alkyl which is optionally substituted identically or differently once to three times by fluorine, chlorine, bromine, methyl, ethyl, propyl, i-propyl, methoxy, ethoxy, tifluoromethyl or trifluormethoxy, represents phenoxy-$C_1$–$C_4$-alkyl which is optionally substituted identically or differently once to three times by fluorine; chlorine, methyl or ethyl or R$^2$ represents $C_1$–$C_{14}$-alkyl, $C_2$–$C_{14}$-alkenyl, $C_1$–$C_4$-alkoxy-$C_2$–$C_6$-alkyl or $C_1$–$C_4$-polyalkoxy-$C_2$–$C_6$-alkyl which are in each case optionally substituted identically or differently once to nine times by fluorine or chlorine, or represents $C_3$–$C_6$-cycloalkyl which is optionally substituted by fluorine, chlorine, methyl, ethyl, methoxy or ethoxy, or represents phenyl or benzyl which are in each case optionally substituted identically or differently once to three times by fluorine, chlorine, nitro, methyl, ethyl, propyl, i-propyl, methoxy, ethoxy or trifluoromethyl.

5. A 3-aryl-4-hydroxy-Δ$^3$-dihydrothiophene derivative according to claim 2, in which G is

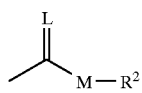

and L and M are oxygen.

6. A 3-aryl-4-hydroxy-Δ$^3$-dihydrothiophene derivative according to claim 2, in which G is hydrogen.

7. A 3-aryl-4-hydroxy-Δ$^3$-dihydrothiophene derivative according to claim 2, in which G is —CO—R$^1$.

8. A 3-aryl-4-hydroxy-Δ$^3$-dihydrothiophene derivative according to claim 1, wherein such compound is of the formula

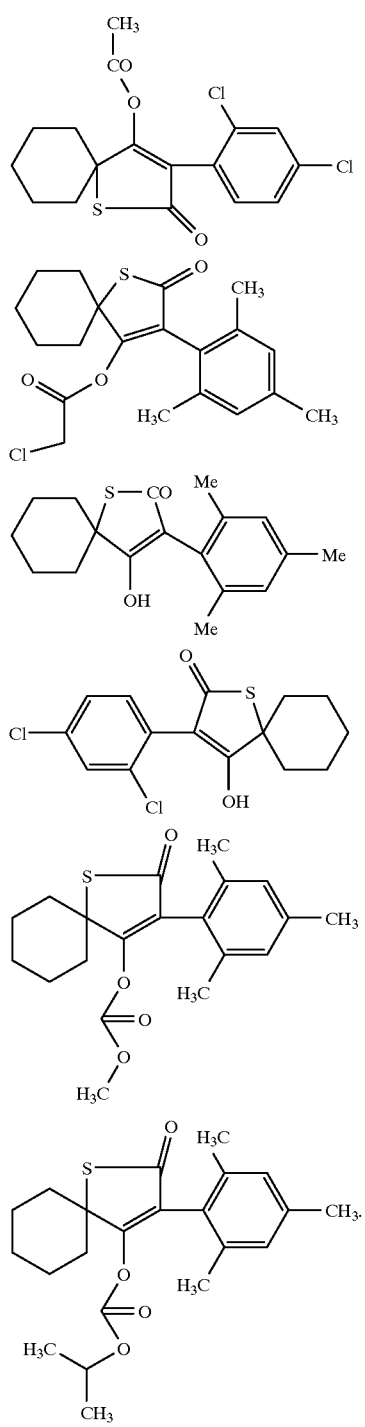

9. A compound according to claim 2, wherein A and B together represent a $C_5$–$C_6$ membered ring.

10. An arthropodicidal or nematicidal composition which comprises an effective amount of a compound according to claim 1 and an inert carrier.

11. A method of combatting arthropods or nematodes which comprises applying an effective amount of a compound according to claim 1 to said arthropods or nematodes or to a habitat where they reside.

* * * * *